(12) United States Patent
Fujiwara et al.

(10) Patent No.: US 11,959,872 B2
(45) Date of Patent: Apr. 16, 2024

(54) METHOD FOR MEASURING AMOUNT OF BLOOD COMPONENT IN BLOOD

(71) Applicant: PHC Holdings Corporation, Tokyo (JP)

(72) Inventors: Masaki Fujiwara, Ehime (JP); Yoshifumi Takahara, Ehime (JP); Takaaki Fujii, Ehime (JP); Setsuko Yano, Ehime (JP); Fuminori Kutsuna, Ehime (JP)

(73) Assignee: PHC Holdings Corporation, Tokyo (JP)

(*) Notice: Subject to any disclaimer, the term of this patent is extended or adjusted under 35 U.S.C. 154(b) by 803 days.

(21) Appl. No.: 16/979,462

(22) PCT Filed: Mar. 1, 2019

(86) PCT No.: PCT/JP2019/008078
§ 371 (c)(1),
(2) Date: Sep. 9, 2020

(87) PCT Pub. No.: WO2019/181436
PCT Pub. Date: Sep. 26, 2019

(65) Prior Publication Data
US 2021/0010969 A1      Jan. 14, 2021

(30) Foreign Application Priority Data
Mar. 19, 2018   (JP) ................................. 2018-050934

(51) Int. Cl.
*G01N 27/327*   (2006.01)
*G01N 33/49*   (2006.01)

(52) U.S. Cl.
CPC ......... *G01N 27/3272* (2013.01); *G01N 33/49* (2013.01)

(58) Field of Classification Search
None
See application file for complete search history.

(56) References Cited

U.S. PATENT DOCUMENTS 6,287,451 B1   9/2001   Winarta et al.
6,875,327 B1   4/2005   Miyazaki et al.
(Continued)

FOREIGN PATENT DOCUMENTS

EP   1 691 192   8/2006
EP   2 076 168   7/2009
(Continued)

OTHER PUBLICATIONS

Office Action issued in corresponding Chinese Patent Application No. 201980020067.2, dated Aug. 3, 2022, 10 pages w/ translation.
(Continued)

*Primary Examiner* — J. Christopher Ball
(74) *Attorney, Agent, or Firm* — HSML P.C.

(57) ABSTRACT

The present invention provides a method for accurately measuring a blood component despite uneven distribution of blood introduced into a capillary. The measurement method according to the present invention is characterized in that a plurality of electrode systems for measuring the hematocrit are provided in a capillary of a biosensor to measure the hematocrit at different positions in the capillary. By measuring the hematocrit at the plurality of positions in the capillary as described above, the hematocrit can be measured mom accurately despite uneven distribution of blood introduced into the capillary.

14 Claims, 42 Drawing Sheets

(56) References Cited

U.S. PATENT DOCUMENTS

| | | | |
|---|---|---|---|
| 2007/0131565 A1 | 6/2007 | Fujiwara et al. | |
| 2007/0138026 A1 | 6/2007 | Fujiwara et al. | |
| 2010/0094110 A1* | 4/2010 | Heller ................ | A61B 5/4848 |
| | | | 600/345 |
| 2010/0243476 A1 | 9/2010 | Fujiwara et al. | |
| 2011/0198223 A1* | 8/2011 | Fujiwara ............ | G01N 27/3274 |
| | | | 204/403.14 |
| 2011/0203942 A1 | 8/2011 | Uchiyama | |
| 2015/0153301 A1 | 6/2015 | Yoshioka | |
| 2016/0273017 A1* | 9/2016 | Fujiwara ............ | G01N 27/307 |
| 2019/0293594 A1 | 9/2019 | Wu et al. | |

FOREIGN PATENT DOCUMENTS

| | | |
|---|---|---|
| EP | 2 860 518 | 4/2015 |
| JP | 9-105750 | 4/1997 |
| JP | 4060078 B | 12/2007 |
| JP | 2011-158483 | 8/2011 |
| WO | 01/36953 | 5/2001 |
| WO | 2008/047843 | 4/2004 |
| WO | 2005/103669 | 3/2005 |
| WO | 2008/030757 | 3/2008 |
| WO | 2018/011692 | 1/2018 |

OTHER PUBLICATIONS

Extended European Search Report issued in corresponding European Patent Application No. 19771986.7, dated Apr. 8, 2021, 9 pages.

International Search Report issued in International Application No. PCT/JP2019/008078, dated Apr. 2, 2019, 2 pages with a translation.

* cited by examiner (a)
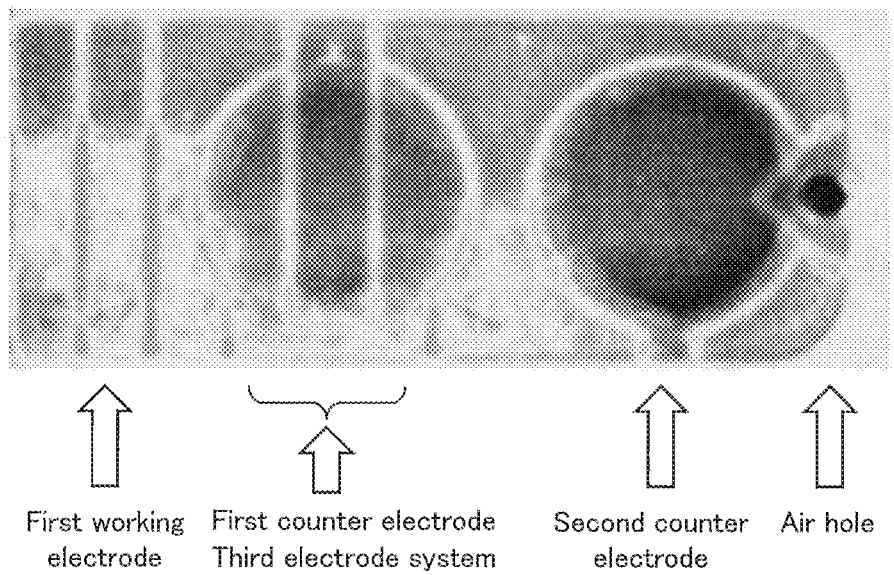
First working electrode | First counter electrode Third electrode system | Second counter electrode | Air hole
(b)
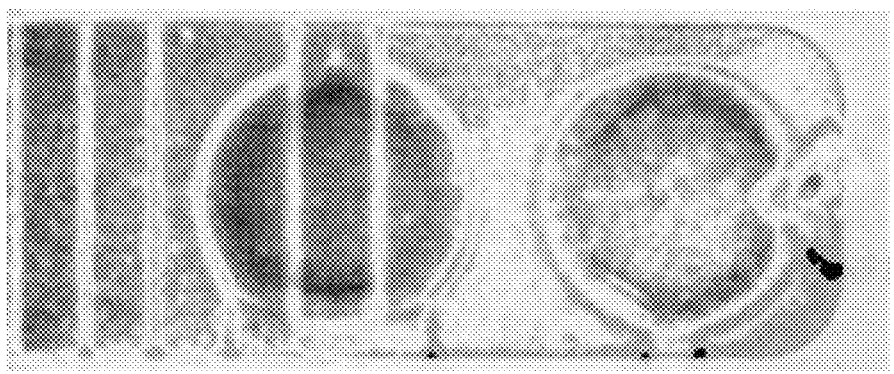
FIG. 1

| Step | | Working electrode | Counter electrode | Applied voltage (mV) | Application time (sec) | Non-application time (sec) | Accumulated time (sec) |
|---|---|---|---|---|---|---|---|
| Second step | Glu-2 | A | G | 500 | 0.2 | | 0.2 |
| | | | | | | 0.2 | 0.4 |
| Second step | Glu-2 | A | G | 300 | 0.2 | | 0.6 |
| First step | Glu-1 | C | E,D | 500 | 0.2 | | 0.8 |
| Second step | Glu-2 | A | G | 400 | 0.2 | | 1.0 |
| First step | Glu-1 | C | E,D | 500 | 0.2 | | 1.2 |
| | | | | | | 0.2 | 1.4 |
| Second step | Glu-2 | A | G | 500 | 0.2 | | 1.6 |
| First step | Glu-1 | C | E,D | 500 | 0.2 | | 1.8 |
| Second step | Glu-2 | A | G | 300 | 0.2 | | 2.0 |
| Second step | Glu-2 | A | G | 600 | 0.2 | | 2.2 |
| First step | Glu-1 | C | E,D | 500 | 0.2 | | 2.4 |
| Third step | Hct-3 | A | C | 2500 | 0.2 | | 2.6 |

FIG. 13

| | | | Working electrode | | Counter electrode | |
|---|---|---|---|---|---|---|
| First electrode system | Glu-1 | First | C | First | E,D |
| Second electrode system | Glu-2 | Second | A | Second | G |
| Third electrode system | Hct-3 | Third | A | Third | C |

FIG. 14

| Step | | Working electrode | Counter electrode | Applied voltage (mV) | Application time (sec) | Non-application time (sec) | Accumulated time (sec) |
|---|---|---|---|---|---|---|---|
| Second step | Glu-2 | A | G | 500 | 0.2 | | 0.2 |
| | | | | | | 0.2 | 0.4 |
| Second step | Glu-2 | A | G | 300 | 0.2 | | 0.6 |
| First step | Glu-1 | C | E,D | 500 | 0.2 | | 0.8 |
| Second step | Glu-2 | A | G | 400 | 0.2 | | 1.0 |
| First step | Glu-1 | C | E,D | 500 | 0.2 | | 1.2 |
| Third step | Het-3 | D | G | 2500 | 0.2 | | 1.4 |
| Second step | Glu-2 | A | G | 500 | 0.2 | | 1.6 |
| First step | Glu-1 | C | E,D | 500 | 0.2 | | 1.8 |
| Second step | Glu-2 | A | G | 300 | 0.2 | | 2.0 |
| Second step | Glu-2 | A | G | 600 | 0.2 | | 2.2 |
| First step | Glu-1 | C | E,D | 500 | 0.2 | | 2.4 |

FIG. 16

| | | Working electrode | | Counter electrode | |
|---|---|---|---|---|---|
| First electrode system | Glu-1 | First | C | First | E,D |
| Second electrode system | Glu-2 | Second | A | Second | G |
| Third electrode system | Het-3 | Third | D | Third | G |

FIG. 17

| Step | | Working electrode | Counter electrode | Applied voltage (mV) | Application time (sec) | Non-application time (sec) | Accumulated time (sec) |
|---|---|---|---|---|---|---|---|
| Second step | Glu-2 | A | G | 500 | 0.2 | | 0.2 |
| | | | | | | 0.2 | 0.4 |
| Second step | Glu-2 | A | G | 300 | 0.2 | | 0.6 |
| First step | Glu-1 | C | E,D | 500 | 0.2 | | 0.8 |
| Second step | Glu-2 | A | G | 400 | 0.2 | | 1.0 |
| First step | Glu-1 | C | E,D | 500 | 0.2 | | 1.2 |
| Third step | Het-3 | G | E | 2500 | 0.2 | | 1.4 |
| Second step | Glu-2 | A | G | 500 | 0.2 | | 1.6 |
| First step | Glu-1 | C | E,D | 500 | 0.2 | | 1.8 |
| Second step | Glu-2 | A | G | 300 | 0.2 | | 2.0 |
| Second step | Glu-2 | A | G | 600 | 0.2 | | 2.2 |
| First step | Glu-1 | C | E,D | 500 | 0.2 | | 2.4 |

FIG. 18

| | | Working electrode | | Counter electrode | |
|---|---|---|---|---|---|
| First electrode system | Glu-1 | First | C | First | E,D |
| Second electrode system | Glu-2 | Second | A | Second | G |
| Third electrode system | Het-3 | Third | G | Third | E |

FIG. 19

| Step | | Working electrode | Counter electrode | Applied voltage (mV) | Application time (sec) | Non-application time (sec) | Accumulated time (sec) |
|---|---|---|---|---|---|---|---|
| First step | Glu-1 | C | E,D | 400 | 0.5 | | 0.5 |
| | | | | | | 1.0 | 1.5 |
| First step | Glu-1 | C | E,D | 400 | 0.5 | | 2.0 |
| | | | | | | 0.4 | 2.4 |
| Fourth step | Het-4 | D | G | 2500 | 0.3 | | 2.7 |
| | | | | | | 0.3 | 3.0 |
| First step | Glu-1 | C | E,D | 400 | 0.5 | | 3.5 |
| | | | | | | 1.0 | 4.5 |
| First step | Glu-1 | C | E,D | 400 | 0.5 | | 5.0 |
| | | | | | | 1.0 | 6.0 |
| First step | Glu-1 | C | E,D | 400 | 0.5 | | 6.5 |
| | | | | | | 0.2 | 6.7 |
| Third step | Het-3 | A | C | 2500 | 0.3 | | 7.0 |

FIG. 21

| | | Working electrode | | Counter electrode | |
|---|---|---|---|---|---|
| First electrode system | Glu-1 | First | C | First | E,D |
| Fourth electrode system | Het-4 | Fourth | D | Fourth | G |
| Third electrode system | Het-3 | Third | A | Third | C |

FIG. 22

| Step | | Working electrode | Counter electrode | Applied voltage (mV) | Application time (sec) | Non-application time (sec) | Accumulated time (sec) |
|---|---|---|---|---|---|---|---|
| First step | Glu-1 | C | E, D | 500 | 0.5 | | 0.5 |
| | | | | | | 0.5 | 1.0 |
| Second step | Glu-2 | A | G | 500 | 0.4 | | 1.4 |
| First step | Glu-1 | C | E, D | 200 | 0.4 | | 1.8 |
| | | | | | | 0.4 | 2.2 |
| Second step | Glu-2 | A | G | 500 | 0.4 | | 2.6 |
| First step | Glu-1 | C | E, D | 300 | 0.4 | | 3.0 |
| | | | | | | 0.1 | 3.1 |
| Fourth step | Hct-4 | D | G | 2500 | 0.3 | | 3.4 |
| Second step | Glu-2 | A | G | 500 | 0.4 | | 3.8 |
| First step | Glu-1 | C | E, D | 400 | 0.4 | | 4.2 |
| | | | | | | 0.4 | 4.6 |
| Second step | Glu-2 | A | G | 500 | 0.9 | | 5.5 |
| First step | Glu-1 | C | E, D | 400 | 0.9 | | 6.4 |
| | | | | | | 0.3 | 6.7 |
| Third step | Hct-3 | A | C | 2500 | 0.3 | | 7.0 |

FIG. 24

| | | Working electrode | | Counter electrode | |
|---|---|---|---|---|---|
| First electrode system | Glu-1 | First | C | First | E, D |
| Second electrode system | Glu-2 | Second | A | Second | G |
| Fourth electrode system | Hct-4 | Fourth | D | Fourth | G |
| Third electrode system | Hct-3 | Third | A | Third | C |

FIG. 25

| Step | | Working electrode | Counter electrode | Applied voltage (mV) | Application time (sec) | Non-application time (sec) | Accumulated time (sec) |
|---|---|---|---|---|---|---|---|
| First step | Glu-1 | C | E,D | 400 | 0.5 | | 0.5 |
| | | | | | | 0.5 | 1.0 |
| Second step | Glu-2 | A | G | 400 | 0.4 | | 1.4 |
| First step | Glu-1 | C | E,D | 400 | 0.4 | | 1.8 |
| | | | | | | 0.4 | 2.2 |
| Second step | Glu-2 | A | G | 400 | 0.4 | | 2.6 |
| First step | Glu-1 | C | E,D | 400 | 0.4 | | 3.0 |
| | | | | | | 0.1 | 3.1 |
| Fourth step | Hct-4 | D | G | 2500 | 0.3 | | 3.4 |
| Second step | Glu-2 | A | G | 400 | 0.4 | | 3.8 |
| First step | Glu-1 | C | E,D | 400 | 0.4 | | 4.2 |
| | | | | | | 0.4 | 4.6 |
| Second step | Glu-2 | A | G | 400 | 0.9 | | 5.5 |
| First step | Glu-1 | C | E,D | 400 | 0.9 | | 6.4 |
| | | | | | | 0.3 | 6.7 |
| Third step | Hct-3 | A | C | 2500 | 0.3 | | 7.0 |

FIG. 27

| | | Working electrode | | Counter electrode | |
|---|---|---|---|---|---|
| First electrode system | Glu-1 | First | C | First | E,D |
| Second electrode system | Glu-2 | Second | A | Second | G |
| Fourth electrode system | Hct-4 | Fourth | D | Fourth | G |
| Third electrode system | Hct-3 | Third | A | Third | C |

FIG. 28

| Step | | Working electrode | Counter electrode | Applied voltage (mV) | Application time (sec) | Non-application time (sec) | Accumulated time (sec) |
|---|---|---|---|---|---|---|---|
| First step | Glu-1 | C | E,D | 500 | 0.5 | | 0.5 |
| Second step | Glu-2 | A | G | 500 | | | |
| | | | | | | 1.0 | 1.5 |
| First step | Glu-1 | C | E,D | 500 | 0.5 | | 2.0 |
| Second step | Glu-2 | A | G | 500 | | | |
| | | | | | | 0.4 | 2.4 |
| Fourth step | Hct-4 | D | G | 2500 | 0.3 | | 2.7 |
| | | | | | | 0.3 | 3.0 |
| First step | Glu-1 | C | E,D | 500 | 0.5 | | 3.5 |
| Second step | Glu-2 | A | G | 500 | | | |
| | | | | | | 1.0 | 4.5 |
| First step | Glu-1 | C | E,D | 500 | 0.5 | | 5.0 |
| Second step | Glu-2 | A | G | 500 | | | |
| | | | | | | 1.0 | 6.0 |
| First step | Glu-1 | C | E,D | 500 | 0.5 | | 6.5 |
| Second step | Glu-2 | A | G | 500 | | | |
| | | | | | | 0.2 | 6.7 |
| Third step | Hct-3 | A | C | 2500 | 0.3 | | 7.0 |

FIG. 30

| | | Working electrode | | Counter electrode | |
|---|---|---|---|---|---|
| First electrode system | Glu-1 | First | C | First | E,D |
| Second electrode system | Glu-2 | Second | A | Second | G |
| Fourth electrode system | Hct-4 | Fourth | D | Fourth | G |
| Third electrode system | Hct-3 | Third | A | Third | C |

FIG. 31

| Step | | Working electrode | Counter electrode | Applied voltage (mV) | Application time (sec) | Non-application time (sec) | Accumulated time (sec) |
|---|---|---|---|---|---|---|---|
| First step | Glu-1 | C | E,D | 500 | 0.5 | | 0.5 |
| Second step | Glu-2 | A | G | 500 | | | |
| | | | | | | 0.9 | 1.4 |
| Second step | Glu-2 | A | G | 500 | 0.3 | | 1.7 |
| First step | Glu-1 | C | E,D | 500 | 0.3 | | 2.0 |
| | | | | | | 0.4 | 2.4 |
| Fourth step | Het-4 | D | G | 2500 | 0.3 | | 2.7 |
| | | | | | | 0.3 | 3.0 |
| First step | Glu-1 | C | E,D | 500 | 0.5 | | 3.5 |
| Second step | Glu-2 | A | G | 500 | | | |
| | | | | | | 0.9 | 4.4 |
| Second step | Glu-2 | A | G | 500 | 0.3 | | 4.7 |
| First step | Glu-1 | C | E,D | 500 | 0.3 | | 5.0 |
| | | | | | | 1.0 | 6.0 |
| First step | Glu-1 | C | E,D | 500 | 0.5 | | 6.5 |
| Second step | Glu-2 | A | G | 500 | | | |
| | | | | | | 0.2 | 6.7 |
| Third step | Het-3 | A | C | 2500 | 0.3 | | 7.0 |

FIG. 33

| | | Working electrode | | Counter electrode | |
|---|---|---|---|---|---|
| First electrode system | Glu-1 | First | C | First | E,D |
| Second electrode system | Glu-2 | Second | A | Second | G |
| Fourth electrode system | Het-4 | Fourth | D | Fourth | G |
| Third electrode system | Het-3 | Third | A | Third | C |

FIG. 34

| Step | | Working electrode | Counter electrode | Applied voltage (mV) | Application time (sec) | Non-application time (sec) | Accumulated time (sec) |
|---|---|---|---|---|---|---|---|
| First step | Glu-1 | C | E,D | 400 | 0.4 | | 0.4 |
| | | | | | | 1.0 | 1.4 |
| First step | Glu-1 | C | E,D | 400 | 0.5 | | 1.9 |
| | | | | | | 1.0 | 2.9 |
| First step | Glu-1 | C | E,D | 400 | 0.5 | | 3.4 |
| | | | | | | 1.0 | 4.4 |
| First step | Glu-1 | C | E,D | 400 | 0.5 | | 4.9 |
| | | | | | | 1.0 | 5.9 |
| First step | Glu-1 | C | E,D | 400 | 0.5 | | 6.4 |
| Third step | Hct-3 | A | C | 2500 | 0.2 | | 6.6 |
| Fifth step | Hct-5 | F | A,G | 2500 | 0.2 | | 6.8 |
| Sixth step | Hct-6 | F | C,E,D | 2500 | 0.2 | | 7.0 |

FIG. 36

| | | Working electrode | | Counter electrode | |
|---|---|---|---|---|---|
| First electrode system | Glu-1 | First | C | First | E,D |
| Third electrode system | Hct-3 | Third | A | Third | C |
| Fifth electrode system | Hct-5 | Fifth | F | Fifth | A,G |
| Sixth electrode system | Hct-6 | Sixth | F | Sixth | C,E,D |

FIG. 37

| Step | | Working electrode | Counter electrode | Applied voltage (mV) | Application time (sec) | Non-application time (sec) | Accumulated time (sec) |
|---|---|---|---|---|---|---|---|
| First step | Glu-1 | C | E,D | 400 | 0.4 | | 0.4 |
| | | | | | | 0.9 | 1.3 |
| First step | Glu-1 | C | E,D | 400 | 0.5 | | 1.8 |
| Seventh step | Hct-7 | F | G | 2500 | 0.2 | | 2.0 |
| | | | | | | 0.9 | 2.9 |
| First step | Glu-1 | C | E,D | 400 | 0.5 | | 3.4 |
| | | | | | | 0.9 | 4.3 |
| First step | Glu-1 | C | E,D | 400 | 0.5 | | 4.8 |
| Seventh step | Hct-7 | F | G | 2500 | 0.2 | | 5.0 |
| | | | | | | 0.9 | 5.9 |
| First step | Glu-1 | C | E,D | 400 | 0.5 | | 6.4 |
| Third step | Hct-3 | A | C | 2500 | 0.2 | | 6.6 |
| Fifth step | Hct-5 | F | A,G | 2500 | 0.2 | | 6.8 |
| Sixth step | Hct-6 | F | C,E,D | 2500 | 0.2 | | 7.0 |

FIG. 39

| | | Working electrode | | Counter electrode | |
|---|---|---|---|---|---|
| First electrode system | Glu-1 | First | C | First | E,D |
| Seventh electrode system | Hct-7 | Seventh | F | Seventh | G |
| Third electrode system | Hct-3 | Third | A | Third | C |
| Fifth electrode system | Hct-5 | Fifth | F | Fifth | A,G |
| Sixth electrode system | Hct-6 | Sixth | F | Sixth | C,E,D |

FIG. 40

| Step | | Working electrode | Counter electrode | Applied voltage (mV) | Application time (sec) | Non-application time (sec) | Accumulated time (sec) |
|---|---|---|---|---|---|---|---|
| First step | Glu-1 | C | E,D | 500 | 0.5 | | 0.5 |
| | | | | | | 0.5 | 1.0 |
| Second step | Glu-2 | A | G | 500 | 0.4 | | 1.4 |
| First step | Glu-1 | C | E,D | 200 | 0.4 | | 1.8 |
| | | | | | | 0.4 | 2.2 |
| Second step | Glu-2 | A | G | 500 | 0.4 | | 2.6 |
| First step | Glu-1 | C | E,D | 300 | 0.4 | | 3.0 |
| | | | | | | 0.4 | 3.4 |
| Second step | Glu-2 | A | G | 500 | 0.4 | | 3.8 |
| First step | Glu-1 | C | E,D | 400 | 0.4 | | 4.2 |
| | | | | | | 0.4 | 4.6 |
| Second step | Glu-2 | A | G | 500 | 0.9 | | 5.5 |
| First step | Glu-1 | C | E,D | 400 | 0.9 | | 6.4 |
| Third step | Hct-3 | A | C | 2500 | 0.2 | | 6.6 |
| Fifth step | Hct-5 | F | A,G | 2500 | 0.2 | | 6.8 |
| Sixth step | Hct-6 | F | C,E,D | 2500 | 0.2 | | 7.0 |

FIG. 42

| | | Working electrode | | Counter electrode | |
|---|---|---|---|---|---|
| First electrode system | Glu-1 | First | C | First | E,D |
| Second electrode system | Glu-2 | Second | A | Second | G |
| Third electrode system | Hct-3 | Third | A | Third | C |
| Fifth electrode system | Hct-5 | Fifth | F | Fifth | A,G |
| Sixth electrode system | Hct-6 | Sixth | F | Sixth | C,E,D |

FIG. 43

| Step | | Working electrode | Counter electrode | Applied voltage (mV) | Application time (sec) | Non-application time (sec) | Accumulated time (sec) |
|---|---|---|---|---|---|---|---|
| First step | Glu-1 | C | E,D | 400 | 0.5 | | 0.5 |
| | | | | | | 0.5 | 1.0 |
| Second step | Glu-2 | A | G | 400 | 0.4 | | 1.4 |
| First step | Glu-1 | C | E,D | 400 | 0.4 | | 1.8 |
| | | | | | | 0.4 | 2.2 |
| Second step | Glu-2 | A | G | 400 | 0.4 | | 2.6 |
| First step | Glu-1 | C | E,D | 400 | 0.4 | | 3.0 |
| | | | | | | 0.4 | 3.4 |
| Second step | Glu-2 | A | G | 400 | 0.4 | | 3.8 |
| First step | Glu-1 | C | E,D | 400 | 0.4 | | 4.2 |
| | | | | | | 0.4 | 4.6 |
| Second step | Glu-2 | A | G | 400 | 0.9 | | 5.5 |
| First step | Glu-1 | C | E,D | 400 | 0.9 | | 6.4 |
| Third step | Hct-3 | A | C | 2500 | 0.2 | | 6.6 |
| Fifth step | Hct-5 | F | A,G | 2500 | 0.2 | | 6.8 |
| Sixth step | Hct-6 | F | C,E,D | 2500 | 0.2 | | 7.0 |

FIG. 45

| | | | Working electrode | | Counter electrode | |
|---|---|---|---|---|---|---|
| First electrode system | Glu-1 | First | C | First | E,D |
| Second electrode system | Glu-2 | Second | A | Second | G |
| Third electrode system | Hct-3 | Third | A | Third | C |
| Fifth electrode system | Hct-5 | Fifth | F | Fifth | A,G |
| Sixth electrode system | Hct-6 | Sixth | F | Sixth | C,E,D |

FIG. 46

| Step | | Working electrode | Counter electrode | Applied voltage (mV) | Application time (sec) | Non-application time (sec) | Accumulated time (sec) |
|---|---|---|---|---|---|---|---|
| First step | Glu-1 | C | E,D | 500 | 0.4 | | 0.4 |
| Second step | Glu-2 | A | G | 500 | | | |
| | | | | | | 1.0 | 1.4 |
| First step | Glu-1 | C | E,D | 500 | 0.5 | | 1.9 |
| Second step | Glu-2 | A | G | 500 | | | |
| | | | | | | 1.0 | 2.9 |
| First step | Glu-1 | C | E,D | 500 | 0.5 | | 3.4 |
| Second step | Glu-2 | A | G | 500 | | | |
| | | | | | | 1.0 | 4.4 |
| First step | Glu-1 | C | E,D | 500 | 0.5 | | 4.9 |
| Second step | Glu-2 | A | G | 500 | | | |
| | | | | | | 1.0 | 5.9 |
| First step | Glu-1 | C | E,D | 500 | 0.5 | | 6.4 |
| Second step | Glu-2 | A | G | 500 | | | |
| Third step | Hct-3 | A | C | 2500 | 0.2 | | 6.6 |
| Fifth step | Hct-5 | F | A,G | 2500 | 0.2 | | 6.8 |
| Sixth step | Hct-6 | F | C,E,D | 2500 | 0.2 | | 7.0 |

FIG. 48

| | | Working electrode | | Counter electrode | |
|---|---|---|---|---|---|
| First electrode system | Glu-1 | First | C | First | E,D |
| Second electrode system | Glu-2 | Second | A | Second | G |
| Third electrode system | Hct-3 | Third | A | Third | C |
| Fifth electrode system | Hct-5 | Fifth | F | Fifth | A,G |
| Sixth electrode system | Hct-6 | Sixth | F | Sixth | C,E,D |

FIG. 49

| Step | | Working electrode | Counter electrode | Applied voltage (mV) | Application time (sec) | Non-application time (sec) | Accumulated time (sec) |
|---|---|---|---|---|---|---|---|
| First step | Glu-1 | C | E,D | 500 | 0.4 | | 0.4 |
| Second step | Glu-2 | A | G | 500 | | | |
| | | | | | | 0.9 | 1.3 |
| Second step | Glu-2 | A | G | 500 | 0.3 | | 1.6 |
| First step | Glu-1 | C | E,D | 500 | 0.3 | | 1.9 |
| | | | | | | 1.0 | 2.9 |
| First step | Glu-1 | C | E,D | 500 | 0.5 | | 3.4 |
| Second step | Glu-2 | A | G | 500 | | | |
| | | | | | | 0.9 | 4.3 |
| Second step | Glu-2 | A | G | 500 | 0.3 | | 4.6 |
| First step | Glu-1 | C | E,D | 500 | 0.3 | | 4.9 |
| | | | | | | 1.0 | 5.9 |
| First step | Glu-1 | C | E,D | 500 | 0.5 | | 6.4 |
| Second step | Glu-2 | A | G | 500 | | | |
| Third step | Hct-3 | A | C | 2500 | 0.2 | | 6.6 |
| Fifth step | Hct-5 | F | A,G | 2500 | 0.2 | | 6.8 |
| Sixth step | Hct-6 | F | C,E,D | 2500 | 0.2 | | 7.0 |

FIG. 51

| | | | Working electrode | | Counter electrode | |
|---|---|---|---|---|---|---|
| First electrode system | Glu-1 | First | C | First | E,D |
| Second electrode system | Glu-2 | Second | A | Second | G |
| Third electrode system | Hct-3 | Third | A | Third | C |
| Fifth electrode system | Hct-5 | Fifth | F | Fifth | A,G |
| Sixth electrode system | Hct-6 | Sixth | F | Sixth | C,E,D |

FIG. 52

| Step | | Working electrode | Counter electrode | Applied voltage (mV) | Application time (sec) | Non-application time (sec) | Accumulated time (sec) |
|---|---|---|---|---|---|---|---|
| First step | Glu-1 | C | E,D | 500 | 0.5 | | 0.5 |
| Seventh step | Hct-7 | F | G | 2500 | 0.2 | | 0.7 |
| | | | | | | 0.3 | 1.0 |
| Second step | Glu-2 | A | G | 500 | 0.4 | | 1.4 |
| First step | Glu-1 | C | E,D | 200 | 0.4 | | 1.8 |
| | | | | | | 0.4 | 2.2 |
| Second step | Glu-2 | A | G | 500 | 0.4 | | 2.6 |
| First step | Glu-1 | C | E,D | 300 | 0.4 | | 3.0 |
| Seventh step | Hct-7 | F | G | 2500 | 0.2 | | 3.2 |
| | | | | | | 0.2 | 3.4 |
| Second step | Glu-2 | A | G | 500 | 0.4 | | 3.8 |
| First step | Glu-1 | C | E,D | 400 | 0.4 | | 4.2 |
| | | | | | | 0.4 | 4.6 |
| Second step | Glu-2 | A | G | 500 | 0.9 | | 5.5 |
| First step | Glu-1 | C | E,D | 400 | 0.9 | | 6.4 |
| Third step | Hct-3 | A | C | 2500 | 0.2 | | 6.6 |
| Fifth step | Hct-5 | F | A,G | 2500 | 0.2 | | 6.8 |
| Sixth step | Hct-6 | F | C,E,D | 2500 | 0.2 | | 7.0 |

FIG. 54

| | | Working electrode | | Counter electrode | |
|---|---|---|---|---|---|
| First electrode system | Glu-1 | First | C | First | E,D |
| Second electrode system | Glu-2 | Second | A | Second | G |
| Seventh electrode system | Hct-7 | Seventh | F | Seventh | G |
| Third electrode system | Hct-3 | Third | A | Third | C |
| Fifth electrode system | Hct-5 | Fifth | F | Fifth | A,G |
| Sixth electrode system | Hct-6 | Sixth | F | Sixth | C,E,D |

FIG. 55

| Step | | Working electrode | Counter electrode | Applied voltage (mV) | Application time (sec) | Non-application time (sec) | Accumulated time (sec) |
|---|---|---|---|---|---|---|---|
| First step | Glu-1 | C | E,D | 400 | 0.5 | | 0.5 |
| Seventh step | Hct-7 | F | G | 2500 | 0.2 | | 0.7 |
| | | | | | | 0.3 | 1.0 |
| Second step | Glu-2 | A | G | 400 | 0.4 | | 1.4 |
| First step | Glu-1 | C | E,D | 400 | 0.4 | | 1.8 |
| | | | | | | 0.4 | 2.2 |
| Second step | Glu-2 | A | G | 400 | 0.4 | | 2.6 |
| First step | Glu-1 | C | E,D | 400 | 0.4 | | 3.0 |
| Seventh step | Hct-7 | F | G | 2500 | 0.2 | | 3.2 |
| | | | | | | 0.2 | 3.4 |
| Second step | Glu-2 | A | G | 400 | 0.4 | | 3.8 |
| First step | Glu-1 | C | E,D | 400 | 0.4 | | 4.2 |
| | | | | | | 0.4 | 4.6 |
| Second step | Glu-2 | A | G | 400 | 0.9 | | 5.5 |
| First step | Glu-1 | C | E,D | 400 | 0.9 | | 6.4 |
| Third step | Hct-3 | A | C | 2500 | 0.2 | | 6.6 |
| Fifth step | Hct-5 | F | A,G | 2500 | 0.2 | | 6.8 |
| Sixth step | Hct-6 | F | C,E,D | 2500 | 0.2 | | 7.0 |

FIG. 57

| | | Working electrode | | Counter electrode | |
|---|---|---|---|---|---|
| First electrode system | Glu-1 | First | C | First | E,D |
| Second electrode system | Glu-2 | Second | A | Second | G |
| Seventh electrode system | Hct-7 | Seventh | F | Seventh | G |
| Third electrode system | Hct-3 | Third | A | Third | C |
| Fifth electrode system | Hct-5 | Fifth | F | Fifth | A,G |
| Sixth electrode system | Hct-6 | Sixth | F | Sixth | C,E,D |

FIG. 58

| Step | | Working electrode | Counter electrode | Applied voltage (mV) | Application time (sec) | Non-application time (sec) | Accumulated time (sec) |
|---|---|---|---|---|---|---|---|
| Second step | Glu-2 | A | G | 500 | 0.2 | | 0.2 |
| Seventh step | Hct-7 | F | G | 2500 | 0.2 | | 0.4 |
| Second step | Glu-2 | A | G | 300 | 0.2 | | 0.6 |
| First step | Glu-1 | C | E,D | 500 | 0.2 | | 0.8 |
| Second step | Glu-2 | A | G | 400 | 0.2 | | 1.0 |
| First step | Glu-1 | C | E,D | 500 | 0.2 | | 1.2 |
| Seventh step | Hct-7 | F | G | 2500 | 0.2 | | 1.4 |
| Second step | Glu-2 | A | G | 500 | 0.2 | | 1.6 |
| First step | Glu-1 | C | E,D | 500 | 0.2 | | 1.8 |
| Second step | Glu-2 | A | G | 300 | 0.2 | | 2.0 |
| Second step | Glu-2 | A | G | 600 | 0.2 | | 2.2 |
| First step | Glu-1 | C | E,D | 500 | 0.2 | | 2.4 |
| Third step | Hct-3 | A | C | 2500 | 0.2 | | 2.6 |
| Fifth step | Hct-5 | F | A,G | 2500 | 0.2 | | 2.8 |
| Sixth step | Hct-6 | F | C,E,D | 2500 | 0.2 | | 3.0 |

FIG. 60

| | | | Working electrode | | Counter electrode | |
|---|---|---|---|---|---|---|
| First electrode system | Glu-1 | | First | C | First | E,D |
| Second electrode system | Glu-2 | | Second | A | Second | G |
| Seventh electrode system | Hct-7 | | Seventh | F | Seventh | G |
| Third electrode system | Hct-3 | | Third | A | Third | C |
| Fifth electrode system | Hct-5 | | Fifth | F | Fifth | A,G |
| Sixth electrode system | Hct-6 | | Sixth | F | Sixth | C,E,D |

FIG. 61

METHOD FOR MEASURING AMOUNT OF BLOOD COMPONENT IN BLOOD

TECHNICAL FIELD

The present invention relates to a method for measuring the amount of a blood component in blood.

BACKGROUND ART

Sensors for measuring a component of a biological sample have been used conventionally in, for example, clinical examinations and self-measurement of blood glucose levels of diabetic patients. Such sensors have a configuration in which, for example, a cover is disposed on an insulating substrate, which has a working electrode and a counter electrode formed on its surface, via a spacer. A reagent containing an oxidoreductase, a mediator (electron mediator), and the like is placed on the working electrode and the counter electrode, and this portion serves as an analysis portion. One end of a channel for introducing blood is in communication with the analysis portion, and the other end of the channel is open to the outside to serve as a blood supply port. Analysis of a component (e.g., blood glucose level) of a biological sample (e.g., blood) using such a sensor is performed in the following manner, for example. First, the sensor is set in a dedicated measuring device (meter). Then, a fingertip or the like is pricked with a lancet to cause bleeding, and the blood supply port of the sensor is brought into contact therewith. The blood is drawn into the channel of the sensor by capillary action, introduced into the analysis portion through the channel, and then comes into contact with the reagent in the analysis portion. Then, the component in the blood reacts with the oxidoreductase to cause an oxidation-reduction reaction, thereby causing a current to flow through the mediator. This current is detected, and based on the thus-obtained current value, the measuring device calculates the amount of the blood component and displays it.

To address growing demands for health monitoring, demand for highly accurate sensors for measuring a component of a biological sample has increased year by year. For example, ISO 15197 (In vitro diagnostic test systems—Requirements for blood-glucose monitoring systems for self-testing in managing diabetes mellitus) that came into effect in May 2013 provides standards that are stricter than those in ISO 15197 that came into effect in 2003.

TABLE 1

| ISO 15197 (2013) | ISO 15197 (2003) |
|---|---|
| 95% of results displayed by a blood glucose meter have to be within the following range: ±15 mg/dl at glucose concentrations of less than 100 mg/dl, and within ±15% at glucose concentrations of 100 mg/dl or more | 95% of results displayed by a blood glucose meter have to be within the following range: ±15 mg/dl at glucose concentrations of less than 75 mg/dl, and within ±20% at glucose concentrations of 75 mg/dl or more |

As an example of a biosensor for performing highly accurate measurement, a biosensor was reported in which a reagent layer 39 is disposed on an electrode system including a working electrode 32 and a counter electrode 36 and another reagent layer 40 is disposed on an electrode system including a working electrode 33 and a counter electrode 35 (Patent Document 1). Another electrode 37 is an electrode for measuring the hematocrit, and the reagent layers 39 and 40 are not in contact with the electrode 37. The reagent layer 39 contains an oxidoreductase and a mediator, and the reagent layer 40 contains a mediator. The hematocrit can be measured by applying a voltage to the above-described electrode 37 and any one of the working electrode 32, the counter electrode 36, the working electrode 33, and the counter electrode 35.

Also, a biosensor in which a reagent is disposed on three electrodes (working electrodes W1 and W2 and a reference electrode R) has been reported (Patent Document 2). An oxidized redox mediator is disposed on the working electrode W1 and the reference electrode R, and an oxidized redox mediator and an enzyme are disposed on the working electrode W2. By applying a voltage between the above-described working electrode W1 and reference electrode R, the resistance value (r value) is measured, and the hematocrit can be calculated using the r value.

CITATION LIST

Patent Documents

Patent Document 1: WO 2005/103669
Patent Document 2: JP 4060078 B2

DISCLOSURE OF INVENTION

Problem to be Solved by the Invention

Heretofore, in order to achieve highly accurate measurement of a blood component, the hematocrit (Hct) of blood introduced into a capillary of a biosensor is measured, and the amount of the blood component is corrected based on this value.

However, according to conventional techniques, blood introduced into a capillary is distributed unevenly, and this makes it difficult to measure a blood component accurately using conventional measurement methods using such a biosensor.

Means for Solving Problem

The inventors of the present invention conducted in-depth studies on uneven distribution of blood introduced into a capillary, and made the findings illustrated with reference to FIG. 1. FIG. 1 shows images for illustrating uneven distribution of blood in a biosensor after the blood is introduced into the biosensor, which has two reagent portions. In FIGS. 1(a) and 1(b), the left side as viewed is the side on which blood is applied as a spot, and the right side as viewed is the side on which an air hole is provided. Blood moves from left to right as viewed in these images. In FIG. 1, portions where a large number of erythrocytes are present are colored black, and portions where a small number of erythrocytes are present are colored gray. In FIG. 1(a), a reagent portion on the side on which blood is applied as a spot is colored gray, and it can be seen that the proportion of plasma components is large and the proportion of erythrocytes is small in this reagent portion. On the other hand, in FIG. 1(b), a reagent portion on the side provided with the air hole is colored gray, and it can be seen that the proportion of plasma components is large and the proportion of erythrocytes is small in this reagent portion. As described above, there is a problem in that, owing to uneven distribution of erythrocytes in the reagent portions of the biosensor, the hematocrit of the entire capillary cannot be measured appropriately. In light of the above-described problem, the inventors of the present invention have developed a method, which includes specific measuring steps, for measuring the amount of a blood component in blood with high accuracy using a biosensor with a specific configuration.

In conventional measurement methods, an electrode system for measuring the hematocrit is provided in a capillary of a biosensor, and the hematocrit is measured using the electrode system. The measurement method according to the present invention is characterized in that a plurality of electrode systems for measuring the hematocrit are provided in a capillary of a biosensor to measure the hematocrit at different positions in the capillary of the biosensor. By measuring the hematocrit at a plurality of positions in the capillary as described above, the hematocrit can be measured more accurately despite uneven distribution of the blood introduced into the capillary.

The present invention provides a method (the method may also be referred to as a "blood component amount measurement method 1" in the present specification) for measuring the amount of a blood component in blood using a biosensor,
the biosensor including:
a first electrode system for measuring a blood component amount-dependent current value, the first electrode system including a first working electrode and a first counter electrode;
a second electrode system for measuring a blood component amount-dependent current value, the second electrode system including a second working electrode and a second counter electrode; and
a third electrode system for measuring a hematocrit-dependent current value, the third electrode system including a third working electrode and a third counter electrode,
wherein a first reagent layer is disposed on the first electrode system,
a second reagent layer is disposed on the second electrode system,
the first reagent layer and the second reagent layer are disposed spaced apart from each other,
the first reagent layer and the second reagent layer each contain a reagent for measuring the amount of the blood component in the blood,
at least one of the first counter electrode, the second working electrode, and the second counter electrode is used as the third working electrode, and
at least one of the first working electrode, the first counter electrode, and the second counter electrode is used as the third counter electrode,
the method including:
a first step of applying a first voltage to the first electrode system and detecting a first blood component amount-dependent current value;
a second step of applying a second voltage to the second electrode system and detecting a second blood component amount-dependent current value;
a third step of applying a third voltage to the third electrode system and detecting a third hematocrit-dependent current value; and
a step of calculating the amount of the blood component using the first blood component amount-dependent current value, the second blood component amount-dependent current value, and the third hematocrit-dependent current value.

The present invention also provides a method (the method may also be referred to as a "blood component amount measurement method 2" in the present specification) for measuring the amount of a blood component in blood using a biosensor,
the biosensor including:
a first electrode system for measuring a blood component amount-dependent current value, the first electrode system including a first working electrode and a first counter electrode;
a third electrode system for measuring a hematocrit-dependent current value, the third electrode system including a third working electrode and a third counter electrode; and
a fourth electrode system for measuring a hematocrit-dependent current value, the fourth electrode system including a fourth working electrode and a fourth counter electrode,
wherein a first reagent layer is disposed on the first electrode system,
a second reagent layer is disposed on the fourth counter electrode and the third working electrode,
the first reagent layer and the second reagent layer are disposed spaced apart from each other,
the first reagent layer and the second reagent layer each contain a reagent for measuring the amount of the blood component in the blood,
the first counter electrode is used as the fourth working electrode, and
the first working electrode is used as the third counter electrode,
the method including:
a first step of applying a first voltage to the first electrode system and detecting a first blood component amount-dependent current value;
a third step of applying a third voltage to the third electrode system and detecting a third hematocrit-dependent current value;
a fourth step of applying a fourth voltage to the fourth electrode system and detecting a fourth hematocrit-dependent current value; and
a step of calculating the amount of the blood component using the first blood component amount-dependent current value, the third hematocrit-dependent current value, and the fourth hematocrit-dependent current value.

The present invention also provides a method according to the blood component amount measurement method 1 (the method may also be referred to as a "blood component amount measurement method 3" in the present specification),
wherein the biosensor further includes a fourth electrode system for measuring a hematocrit-dependent current value, the fourth electrode system including a fourth working electrode and a fourth counter electrode,
the first counter electrode is used as the fourth working electrode, and
the second counter electrode is used as the fourth counter electrode,
the method further includes a fourth step of applying a fourth voltage to the fourth electrode system and detecting a fourth hematocrit-dependent current value, and
the step of calculating the amount of the blood component includes a step of calculating the amount of the blood component using the first blood component amount-dependent current value, the second blood component amount-dependent current value, the third hematocrit-dependent current value, and the fourth hematocrit-dependent current value.

The present invention also provides a method (the method may also be referred to as a "blood component amount measurement method 4" in the present specification) for measuring the amount of a blood component in blood using a biosensor, the biosensor including:
a first electrode system for measuring a blood component amount-dependent current value, the first electrode system including a first working electrode and a first counter electrode;
a third electrode system for measuring a hematocrit-dependent current value, the third electrode system including a third working electrode and a third counter electrode;
a fifth electrode system for measuring a hematocrit-dependent current value, the fifth electrode system including a fifth working electrode and a fifth counter electrode; and
a sixth electrode system for measuring a hematocrit-dependent current value, the sixth electrode system including a sixth working electrode and a sixth counter electrode,
wherein a first reagent layer is disposed on the first electrode system,
a second reagent layer is disposed on the fifth counter electrode of the fifth electrode system,
the first reagent layer and the second reagent layer are disposed spaced apart from each other,
the reagent layers are not disposed on the fifth working electrode of the fifth electrode system and the sixth working electrode of the sixth electrode system,
the first reagent layer and the second reagent layer each contain a reagent for measuring the amount of the blood component in the blood,
the fifth counter electrode is used as the third working electrode,
the first working electrode is used as the third counter electrode, and
one of the first working electrode and the first counter electrode is used as the sixth counter electrode,
the method including:
a first step of applying a first voltage to the first electrode system and detecting a first blood component amount-dependent current value;
a third step of applying a third voltage to the third electrode system and detecting a third hematocrit-dependent current value;
a fifth step of applying a fifth voltage to the fifth electrode system and detecting a fifth hematocrit-dependent current value;
a sixth step of applying a sixth voltage to the sixth electrode system and detecting a sixth hematocrit-dependent current value; and
a step of calculating the amount of the blood component using the first blood component amount-dependent current value, the third hematocrit-dependent current value, the fifth hematocrit-dependent current value, and the sixth hematocrit-dependent current value.

The present invention also provides a method according to the blood component amount measurement method 4 (the method may also be referred to as a "blood component amount measurement method 5" in the present specification), wherein the biosensor further includes a seventh electrode system for measuring a hematocrit-dependent current value, the seventh electrode system including a seventh working electrode and a seventh counter electrode,
one of the fifth working electrode and the sixth working electrode is used as the seventh working electrode,
the fifth counter electrode is used as the seventh counter electrode,
the method further includes a seventh step of applying a seventh voltage to the seventh electrode system and detecting a seventh hematocrit-dependent current value, and
the step of calculating the amount of the blood component includes a step of calculating the amount of the blood component using the first blood component amount-dependent current value, the third hematocrit-dependent current value, the fifth hematocrit-dependent current value, the sixth hematocrit-dependent current value, and the seventh hematocrit-dependent current value.

The present invention also provides a method according to the blood component amount measurement method 4 (the method may also be referred to as a "blood component amount measurement method 6" in the present specification), wherein the biosensor further includes a second electrode system for measuring a blood component amount-dependent current value, the second electrode system including a second working electrode and a second counter electrode,
the second reagent layer is also disposed on the second electrode system,
the method further includes a step of applying a second voltage to the second electrode system and detecting a second blood component amount-dependent current value, and
the step of calculating the amount of the blood component includes a step of calculating the amount of the blood component using the first blood component amount-dependent current value, the second blood component amount-dependent current value, the third hematocrit-dependent current value, the fifth hematocrit-dependent current value, and the sixth hematocrit-dependent current value.

The present invention also provides a method according to the blood component amount measurement method 6 (the method may also be referred to as a "blood component amount measurement method 7" in the present specification), wherein the biosensor further includes a seventh electrode system for measuring a hematocrit-dependent current value, the seventh electrode system including a seventh working electrode and a seventh counter electrode,
one of the fifth working electrode and the sixth working electrode is used as the seventh working electrode,
the fifth counter electrode is used as the seventh counter electrode,
the method further includes a seventh step of applying a seventh voltage to the seventh electrode system and detecting a seventh hematocrit-dependent current value, and
the step of calculating the amount of the blood component includes a step of calculating the amount of the blood component using the first blood component amount-dependent current value, the second blood component amount-dependent current value, the third hematocrit-dependent current value, the fifth hematocrit-dependent current value, the sixth hematocrit-dependent current value, and the seventh hematocrit-dependent current value.

Effects of the Invention

As described above, in the method for measuring a blood component according to the present invention, the reagent portions and the electrodes are configured so as to solve the problem of uneven distribution of blood in a biosensor. Accordingly, by applying voltages to the plurality of electrode systems, measurement can be performed in consideration of uneven distribution of blood. Therefore, the measurement method according to the present invention improves the measurement accuracy even if the blood distribution in a biosensor is uneven.

In the present specification, when a "method for measuring a blood component" is simply referred to, it refers to all of the above-described "blood component amount measurement method 1", "blood component amount measurement method 2", "blood component amount measurement method 3", "blood component amount measurement method 4", "blood component amount measurement method 5", "blood component amount measurement method 6", and "blood component amount measurement method 7".

BRIEF DESCRIPTION OF DRAWINGS

FIG. 1 shows images for illustrating uneven distribution of blood in a capillary of a biosensor having an electrode configuration according to the present invention.

FIG. 13 is a table showing electrodes, the applied voltage, the timing of voltage application, and the application time in the voltage application pattern in Embodiment 1A.

FIG. 14 is a table showing electrodes find electrode systems in a biosensor used in Embodiment 1A.

FIG. 16 is a table showing electrodes, the applied voltage, the timing of voltage application, and the application time in the voltage application pattern in Embodiment 1B.

FIG. 17 is a table showing electrodes and electrode systems in a biosensor used in Embodiment 1B.

FIG. 18 is a table showing electrodes, the applied voltage, the timing of voltage application, and the application time in a voltage application pattern in Embodiment 1C.

FIG. 19 is a table showing electrodes and electrode systems in a biosensor used in Embodiment 1C.

FIG. 21 is a table showing electrodes, the applied voltage, the timing of voltage application, and the application time in the voltage application pattern in Embodiment 2.

FIG. 22 is a table showing electrodes and electrode systems in a biosensor used in Embodiment 2.

FIG. 24 is a table allowing electrodes, the applied voltage, the timing of voltage application, and the application time in the voltage application pattern in Embodiment 3A.

FIG. 25 is a table showing electrodes and electrode systems in a biosensor used in Embodiment 3A.

FIG. 27 is a table showing electrodes, the applied voltage, the timing of voltage application, and the application time in the voltage application pattern in Embodiment 3B.

FIG. 28 is a table showing electrodes and electrode systems in a biosensor used in Embodiment 3B.

FIG. 30 is a table showing electrodes, the applied voltage, the timing of voltage application, and the application time in the voltage application pattern in Embodiment 3C.

FIG. 31 is a table showing electrodes and electrode systems in a biosensor used in Embodiment 3C.

FIG. 33 is a table showing electrodes, the applied voltage, the timing of voltage application, and the application time in the voltage application pattern in Embodiment 3D.

FIG. 34 is a table showing electrodes and electrode systems in a biosensor used in Embodiment 3D.

FIG. 36 is a table showing electrodes, the applied voltage, the timing of voltage application, and the application time in the voltage application pattern in Embodiment 4.

FIG. 37 is a table showing electrodes and electrode systems in a biosensor used in Embodiment 4.

FIG. 39 is a table showing electrodes, the applied voltage, the timing of voltage application, and the application time in the voltage application pattern in Embodiment 5.

FIG. 40 is a table showing electrodes and electrode systems in a biosensor used in Embodiment 5.

FIG. 42 is a table showing electrodes, the applied voltage, the timing of voltage application, and the application time in the voltage application pattern in Embodiment 6A.

FIG. 43 is a table showing electrodes and electrode systems in a biosensor used in Embodiment 6A.

FIG. 45 is a table showing electrodes, the applied voltage, the timing of voltage application, and the application time in the voltage application pattern in Embodiment 6B.

FIG. 46 is a table showing electrodes and electrode systems in a biosensor used in Embodiment 6B.

FIG. 48 is a table showing electrodes, the applied voltage, the timing of voltage application, and the application time in the voltage application pattern in Embodiment 6C.

FIG. 49 is a table showing electrodes and electrode systems in a biosensor used in Embodiment 6C.

FIG. 51 is a table showing electrodes, the applied voltage, the timing of voltage application, and the application time in the voltage application pattern in Embodiment 6D.

FIG. 52 is a table showing electrodes and electrode systems in a biosensor used in Embodiment 6D.

FIG. 54 is a table showing electrodes, the applied voltage, the timing of voltage application, and the application time in the voltage application pattern in Embodiment 7A.

FIG. 55 is a table showing electrodes and electrode systems in a biosensor used in Embodiment 7A.

FIG. 57 is a table showing electrodes, the applied voltage, the timing of voltage application, and the application time in the voltage application pattern in Embodiment 7B.

FIG. 58 is a table showing electrodes and electrode systems in a biosensor used in Embodiment 7B.

FIG. 60 is a table showing electrodes, the applied voltage, the timing of voltage application, mid the application time in the voltage application pattern in Embodiment 7C.

FIG. 61 is a table showing electrodes and electrode systems in a biosensor used in Embodiment 7C.

DESCRIPTION OF THE INVENTION

Figure 2:
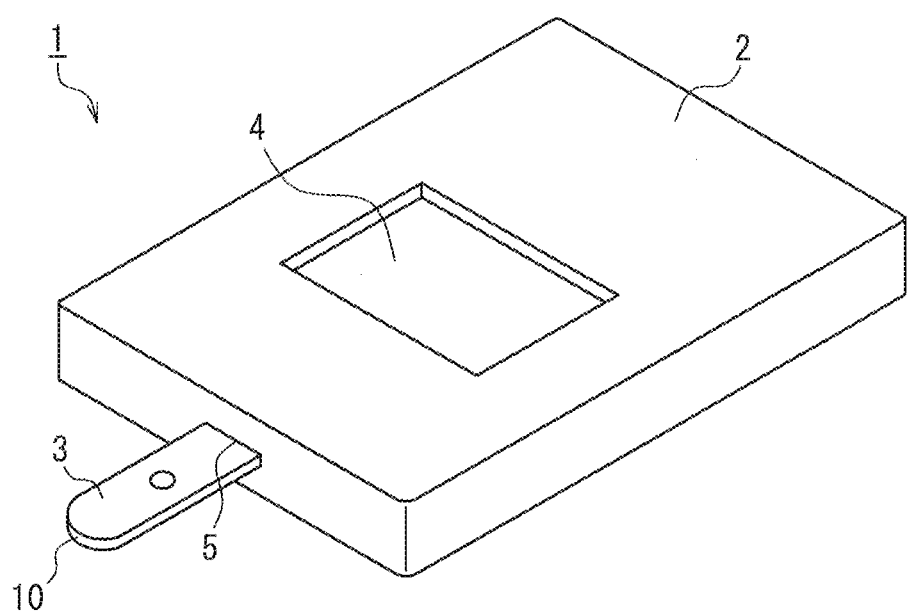
FIG. 2 is a perspective view showing an example of a measuring device used in a measurement method of the present invention.

Next, the present invention will be described in detail.

In the blood component amount measurement methods 1 to 7 of the present invention, examples of a component to be measured include glucose, ketone, HbA1c, lactic acid, uric acid, bilirubin, and cholesterol. In the biosensor used in the measurement method of the present invention, an enzyme to be contained in the reagent portions is selected as appropriate according to a component to be measured in a biological sample.

It should be noted that the blood component amount measurement methods 1 to 7 of the present invention constitute portions of a configuration and a measurement method for improving the measurement accuracy by determining the behavior of blood in the entire capillary, and there is no limitation thereto.

First Embodiment: Blood Component Amount Measurement Method 1

The present invention provides a method (blood component amount measurement method 1) for measuring the amount of a blood component in blood using a biosensor, the biosensor including:
  a first electrode system for measuring a blood component amount-dependent current value, the first electrode system including a first working electrode and a first counter electrode;
  a second electrode system for measuring a blood component amount-dependent current value, the second electrode system including a second working electrode and a second counter electrode; and
  a third electrode system for measuring a hematocrit-dependent current value, the third electrode system including a third working electrode and a third counter electrode,
  wherein a first reagent layer is disposed on the first electrode system,
  a second reagent layer is disposed on the second electrode system,
  the first reagent layer and the second reagent layer are disposed spaced apart from each other,
  the first reagent layer and the second reagent layer each contain a reagent for measuring the amount of the blood component in the blood,
  at least one of the first counter electrode, the second working electrode, and the second counter electrode is used as the third working electrode, and
  at least one of the first working electrode, the first counter electrode, and the second counter electrode is used as the third counter electrode,
  the method including:
  a first step of applying a first voltage to the first electrode system and detecting a first blood component amount-dependent current value;
  a second step of applying a second voltage to the second electrode system and detecting a second blood component amount-dependent current value;
  a third step of applying a third voltage to the third electrode system and detecting a third hematocrit-dependent current value; and
  a step of calculating the amount of the blood component using the first blood component amount-dependent current value, the second blood component amount-dependent current value, and the third hematocrit-dependent current value.

In the blood component amount measurement method 1, it is preferable that the third step is performed after the first step and the second step. The reason for this is that, since the step of detecting the blood component amount-dependent current value is complete, any of the working electrodes and the counter electrodes in the first electrode system and the second electrode system used in the step of detecting the first blood component amount-dependent current value or the second blood component amount-dependent current value can be used as the counter electrode in the electrode system to be used when detecting the third hematocrit-dependent current value.

In the blood component amount measurement method 1, the first step may be performed at least twice, and two or more first blood component amount-dependent current values obtained may be used as the first blood component amount-dependent current values in the step of calculating the amount of the blood component. At this time, the first voltages may be different from each other. Alternatively, at this time, the first voltages may be equal to each other.

In the blood component amount measurement method 1, the second step may be performed at least twice, and two or more second blood component amount-dependent current values obtained may be used as the second blood component amount-dependent current values in the step of calculating the amount of the blood component. At this time, the second voltages may be different from each other. Alternatively, at this time, the second voltages may be equal to each other.

In the blood component amount measurement method 1, the first step may be performed at least twice, the second step may be performed at least twice, and all of the first steps and the second steps may be performed simultaneously. At this time, the first voltages may be different from each other. Alternatively, at this time, the first voltages may be equal to each other. Also, at this time, the second voltages may be different from each other. Alternatively, at this time, the second voltages may be equal to each other. When the first voltages are equal to each other and the second voltages are equal to each other, the first voltage and the second voltage may be equal to each other. Alternatively, when the first voltages are equal to each other and the second voltages are equal to each other, the first voltage and the second voltage may be different from each other.

In the blood component amount measurement method 1, the first step may be performed at least twice, the second step may be performed at least twice, and portions of the first steps and the second steps may be performed simultaneously. At this time, the first voltages may be different from each other. Alternatively, at this time, the first voltages may be equal to each other. Also, at this time, the second voltages may be different from each other. Alternatively, at this time, the second voltages may be equal to each other. When the first voltages are equal to each other and the second voltages are equal to each other, the first voltage and the second voltage may be equal to each other. Alternatively, when the first voltages are equal to each other and the second voltages are equal to each other, the first voltage and the second voltage may be different from each other.

In the blood component amount measurement method 1, the third step may be performed after the first step is performed at least once. Also, in the third step, the second step may be performed at least once. Also, the third step may be performed after the first step is performed at least once and the second step is performed at least once. In the blood component amount measurement method 1, the third step may be performed at least twice.

In the blood component amount measurement methods 1 to 7 of the present invention, it is preferable that the first reagent layer and the second reagent layer each contain a mediator. The mediator is not particularly limited, and may be, for example, a ferricyanide, p-benzoquinone, a p-benzoquinone derivative, phenazine methosulfate, methylene blue, ferrocene, or a ferrocene derivative. Of these, phenanthrenequinone (9,10-phenanthrenequinone), 3-phenylimino-3H-phenothiazine, or a ferricyanide (potassium ferricyanide) is preferable. The amount of mediator to be mixed is not particularly limited, and is, for example, 0.1 to 1000 mM, preferably 1 to 500 mM, and more preferably 10 to 300 mM per measurement or per biosensor. For example, when a glucose level (blood component) in blood (biological sample) is to be measured, in the case of a biosensor in which glucose dehydrogenase (oxidoreductase) is used as an enzyme and potassium ferricyanide is used as a mediator, a Glu-dependent current value is obtained in the following manner, for example. In the biosensor, the blood comes into contact with the oxidoreductase and the mediator, and the oxidoreductase and the mediator are dissolved in the blood. Then, an enzyme reaction proceeds between Glu, which is a substrate in the blood, and the oxidoreductase, whereby the mediator is reduced to produce a ferrocyanide. Upon completion of this reaction, the reduced mediator is electrochemically oxidized, and from the current obtained at this time, a current value that depends on Glu in the blood is obtained.

In the blood component amount measurement methods 1 to 7 of the present invention, it is preferable that the second reagent layer further contains an oxidoreductase. The oxidoreductase is selected as appropriate according to the blood component to be measured. Examples of the oxidoreductase include glucose oxidase, lactate oxidase, cholesterol oxidase, bilirubin oxidase, glucose dehydrogenase, and lactate dehydrogenase. When the blood component to be measured is glucose, glucose oxidase and glucose dehydrogenase are preferable as the oxidoreductase. The amount of the oxidoreductase is, for example, 0.01 to 100 U, preferably 0.05 to 10 U, and more preferably 0.1 to 5 U per biosensor or per measurement.

In the blood component amount measurement method 1, the first voltage is, for example, 0.1 V to 1.0 V, preferably 0.2 V to 0.8 V, and more preferably 0.3 V to 0.6 V. The application time of the first voltage is, for example, 0.05 to 2 seconds, preferably 0.1 to 1 second, and more preferably 0.1 to 0.3 seconds. When the first step is performed at least twice, the first voltages may be equal to or different from each other and the application times of the first voltage may be equal to or different from each other between the first steps.

In the blood component amount measurement method 1, the second voltage is, for example, 0.1 V to 1.0 V, preferably 0.2 V to 0.8 V, and more preferably 0.3 V to 0.6 V. The application time of the second voltage is, for example, 0.05 to 2 seconds, preferably 0.1 to 1 second, and more preferably 0.1 to 0.3 seconds. When the second step is performed at least twice, the second voltages may be equal to or different from each other and the application times of the second voltage may be equal to or different from each other between the second steps.

In the blood component amount measurement method 1, the third voltage is, for example, 1.0 V to 5.0 V, preferably 1.5 to 4.5 V, and more preferably 2.0 to 4.0 V. The application time of the third voltage is, for example, 0.05 to 1 second, preferably 0.1 to 0.5 seconds, and more preferably 0.1 to 0.3 seconds. When the third step is performed at least twice, the third voltages may be equal to or different from each other and the application times of the third voltage may be equal to or different from each other between the third steps.

In the blood component amount measurement method 1, the first voltage and the third voltage preferably satisfy the following relationship: the third voltage>the first voltage.

The second voltage and the third voltage may satisfy the following relationship: the third voltage>the second voltage.

In the blood component amount measurement method 1, the first voltage and the second voltage preferably satisfy the following relationship: the first voltage≥the second voltage. In addition, in the blood component amount measurement method 1, the following relationship may be satisfied: the application time of the first voltage≤the application time of the second voltage.

In the blood component amount measurement method 1, the first voltage is, for example, 0.1 V to 1.0 V, preferably 0.2 V to 0.8 V, and more preferably 0.3 V to 0.6 V, the second voltage is, for example, 0.1 V to 1.0 V, preferably 0.2 V to 0.8 V, and more preferably 0.3 V to 0.6 V, and the third voltage is, for example, 1.0 V to 5.0 V, preferably 1.5 V to 4.5 V, and more preferably 2.0 V to 4.0 V. The following relationships are satisfied: the third voltage>the first voltage, for example, and the third voltage>the second voltage, for example. The application time of the first voltage is, for example, 0.05 to 2 seconds, preferably 0.1 to 1 second, and more preferably 0.1 to 0.3 seconds, the application time of the second voltage is, for example, 0.05 to 2 seconds, preferably 0.1 to 1 second, and more preferably 0.1 to 0.3 seconds, and the application time at the third voltage is, for example, 0.05 to 1 second, preferably 0.1 to 0.5 seconds, and more preferably 0.1 to 0.3 seconds.

Second Embodiment: Blood Component Amount Measurement Method 2

The present invention provides a method (blood component amount measurement method 2) for measuring the amount of a blood component in blood using a biosensor, the biosensor including:
- a first electrode system for measuring a blood component amount-dependent current value, the first electrode system including a first working electrode and a first counter electrode;
- a third electrode system for measuring a hematocrit-dependent current value, the third electrode system including a third working electrode and a third counter electrode; and
- a fourth electrode system for measuring a hematocrit-dependent current value, the fourth electrode system including a fourth working electrode and a fourth counter electrode,
- wherein a first reagent layer is disposed on the first electrode system,
- a second reagent layer is disposed on the fourth counter electrode and the third working electrode,
- the first reagent layer and the second reagent layer are disposed spaced apart from each other,
- the first reagent layer and the second reagent layer each contain a reagent for measuring the amount of the blood component in the blood,
- the first counter electrode is used as the fourth working electrode, and
- the first working electrode is used as the third counter electrode,
- the method including:
- a first step of applying a first voltage to the first electrode system and detecting a first blood component amount-dependent current value;
- a third step of applying a third voltage to the third electrode system and detecting a third hematocrit-dependent current value;
- a fourth step of applying a fourth voltage to the fourth electrode system and detecting a fourth hematocrit-dependent current value; and
- a step of calculating the amount of the blood component using the first blood component amount-dependent current value, the third hematocrit-dependent current value, and the fourth hematocrit-dependent current value.

In the blood component amount measurement method 2, the first step may be performed at least twice, and two or more first blood component amount-dependent current values obtained may be used as the first blood component amount-dependent current values in the step of calculating the amount of the blood component. At this time, the first voltages may be different from each other. Alternatively, at this time, the first voltages may be equal to each other.

In the blood component amount measurement method 2, the third step may be performed after the first step is performed at least once. In this case, the first step may be further performed at least once after the third step. In the blood component amount measurement method 2, the third step may be performed at least twice.

In the blood component amount measurement method 2, the fourth step may be performed after the first step is performed at least once. The fourth step may be performed after the first step and the third step. In the blood component amount measurement method 2, the fourth step may be performed at least twice.

In the blood component amount measurement method 2, it is preferable that the first reagent layer and the second reagent layer each contain a mediator. The mediator is as described in the blood component amount measurement method 1.

In the blood component amount measurement method 2, it is preferable that the first reagent layer and the second reagent layer further contain an oxidoreductase. The oxidoreductase is as described in the blood component amount measurement method 1.

In the blood component amount measurement method 2, the first voltage is, for example, 0.1 V to 1.0 V, preferably 0.2 V to 0.8 V, and more preferably 0.3 V to 0.6 V. The application time of the first voltage is, for example, 0.05 to 2 seconds, preferably 0.1 to 1 second, and more preferably 0.1 to 0.3 seconds. When the first step is performed at least twice, the first voltages may be equal to or different from each other anti the application times of the first voltage may be equal to or different from each other between the first steps.

In the blood component amount measurement method 2, the third voltage is, for example, 1.0 V to 5.0 V, preferably 1.5 to 4.5 V, and more preferably 2.0 to 4.0 V. The application time of the third voltage is, for example, 0.05 to 1 second, preferably 0.1 to 0.5 seconds, and more preferably 0.1 to 0.3 seconds. When the third step is performed at least twice, the third voltages may be equal to or different from each other and the application times of the third voltage may be equal to or different from each other between the third steps.

In the blood component amount measurement method 2, the fourth voltage is, for example, 1.0 V to 5.0 V, preferably 1.5 to 4.5 V, and more preferably 2.0 to 4.0 V. The application time of the fourth voltage is, for example, 0.05 to 1 second, preferably 0.1 to 0.5 seconds, and more preferably 0.1 to 0.3 seconds. When the fourth step is performed at least twice, the fourth voltages may be equal to or different from each other and the application times of the fourth voltage may be equal to or different from each other between the fourth steps.

In the blood component amount measurement method 2, the first voltage and the third voltage preferably satisfy the following relationship: the third voltage>the first voltage. The first voltage and the fourth voltage may satisfy the following relationship: the fourth voltage>the first voltage.

In the blood component amount measurement method 2, the first voltage is, for example, 0.1 V to 1.0 V, preferably 0.2 V to 0.8 V, and more preferably 0.3 V to 0.6 V, the third voltage is, for example, 1.0 V to 5.0 V, preferably 1.5 to 4.5 V, and more preferably 2.0 to 4.0 V, and the fourth voltage is, for example, 1.0 V to 5.0 V, preferably 1.5 to 4.5 V, and more preferably 2.0 to 4.0 V. The following relationships are satisfied: the third voltage>the first voltage, for example, and the fourth voltage>the first voltage, for example. The application time of the first voltage is, for example, 0.05 to 2 seconds, preferably 0.1 to 1 second, and more preferably 0.1 to 0.3 seconds, the application time of the third voltage is, for example, 0.05 to 1 second, preferably 0.1 to 0.5 seconds, and more preferably 0.1 to 0.3 seconds, and the application time of the fourth voltage is, for example, 0.05 to 1 second, preferably 0.1 to 0.5 seconds, and more preferably 0.1 to 0.3 seconds.

Third Embodiment: Blood Component Amount Measurement Method 3

The present invention provides a method (blood component amount measurement method 3) according to the blood component amount measurement method 1,
  wherein the biosensor further includes a fourth electrode system for measuring a hematocrit-dependent current value, the fourth electrode system including a fourth working electrode and a fourth counter electrode,
  the first counter electrode is used as the fourth working electrode, and
  the second counter electrode is used as the fourth counter electrode,
  the method further includes a fourth step of applying a fourth voltage to the fourth electrode system and detecting a fourth hematocrit-dependent current value, and
  the step of calculating the amount of the blood component includes a step of calculating the amount of the blood component using the first blood component amount-dependent current value, the second blood component amount-dependent current value, the third hematocrit-dependent current value, and the fourth hematocrit-dependent current value.

In the blood component amount measurement method 3, the first step may be performed at least twice, and two or more first blood component amount-dependent current values obtained may be used as the first blood component amount-dependent current values in the step of calculating the amount of the blood component. At this time, the first voltages may be different from each other. Alternatively, at this time, the first voltages may be equal to each other.

In the blood component amount measurement method 3, the second step may be performed at least twice, and two or move second blood component amount-dependent current values obtained may be used as the second blood component amount-dependent current values in the step of calculating the amount of the blood component. At this time, the second voltages may be different from each other. Alternatively, at this time, the second voltages may be equal to each other.

In the blood component amount measurement method 3, the first step may be performed at least twice, the second step may be performed at least twice, and all of the first steps and the second steps may be performed simultaneously. At this time, the first voltages may be different from each other. Alternatively, at this time, the first voltages may be equal to each other. Also, at this time, the second voltages may be different from each other. Alternatively, at this time, the second voltages may be equal to each other.

In the blood component amount measurement method 3, the first step may be performed at least twice, the second step may be performed at least twice, and portions of the first steps and the second steps may be performed simultaneously. At this time, the first voltages may be different from each other. Alternatively, at this time, the first voltages may be equal to each other. Also, at this time, the second voltages may be different from each other. Alternatively, at this time, the second voltages may be equal to each other.

In the blood component amount measurement method 3, the third step may be performed after the first step is performed at least once. In this case, the first step may be further performed at least once after the third step. Also, in the blood component amount measurement method 3, the third step may be performed after the second step is performed at least once. In this case, the second step may be further performed at least once after the third step. In the blood component amount measurement method 3, the third step may be performed at least twice.

In the blood component amount measurement method 3, the fourth step may be performed after the first step is performed at least once and the second step is performed at least once. The fourth step may be performed after the first step, the second step, and the third step. In the blood component amount measurement method 3, the fourth step may be performed at least twice.

In the blood component amount measurement method 3, it is preferable that the first reagent layer and the second reagent layer each contain a mediator. The mediator is as described in the blood component amount measurement method 1.

In the blood component amount measurement method 3, it is preferable that the first reagent layer and the second reagent layer further contain an oxidoreductase. The oxidoreductase is as described in the blood component amount measurement method 1.

In the blood component amount measurement method 3, the first voltage is, for example, 0.1 V to 1.0 V, preferably 0.2 V to 0.8 V, and more preferably 0.3 V to 0.6 V. The application time of the first voltage is, for example, 0.05 to 2 seconds, preferably 0.1 to 1 second, and more preferably 0.1 to 0.3 seconds. When the first step is performed at least twice, the first voltages may be equal to or different from each other and the application times of the first voltage may be equal to or different from each other between the first steps.

In the blood component amount measurement method 3, the second voltage is, for example, 0.1 V to 1.0 V, preferably 0.2 V to 0.8 V, and more preferably 0.3 V to 0.6 V. The application time of the second voltage is, for example, 0.05 to 2 seconds, preferably 0.1 to 1 second, and more preferably 0.1 to 0.3 seconds. When the second step is performed at least twice, the second voltages may be equal to or different from each other and the application times of the second voltage may be equal to or different from each other between the second steps.

In the blood component amount measurement method 3, the third voltage is, for example, 1.0 V to 5.0 V, preferably 1.5 to 4.5 V, and more preferably 2.0 to 4.0 V. The application time of the third voltage is, for example, 0.05 to 1 second, preferably 0.1 to 0.5 seconds, and more preferably 0.1 to 0.3 seconds. When the third step is performed at least twice, the third voltages may be equal to or different from each other and the application times of the third voltage may be equal to or different from each other between the third steps.

In the blood component amount measurement method 3, the fourth voltage is, for example, 1.0 V to 5.0 V, preferably 1.5 to 4.5 V, and more preferably 2.0 to 4.0 V. The application time of the fourth voltage is, for example, 0.05 to 1 second, preferably 0.1 to 0.5 seconds, and more preferably 0.1 to 0.3 seconds. When the fourth step is performed at least twice, the fourth voltages may be equal to or different from each other and the application times of the fourth voltage may be equal to or different from each other between the fourth steps.

In the blood component amount measurement method 3, the first voltage and the third voltage preferably satisfy the following relationship: the third voltage>the first voltage. The first voltage and the fourth voltage may satisfy the following relationship: the fourth voltage>the first voltage.

In the blood component amount measurement method 3, the second voltage and the third voltage preferably satisfy the following relationship: the third voltage>the second voltage. The second voltage and the fourth voltage may satisfy the following relationship: the fourth voltage>the second voltage.

In the blood component amount measurement method 3, the first voltage and the second voltage preferably satisfy the following relationship: the first voltage≥the second voltage. In addition, in the blood component amount measurement method 3, the following relationship may be satisfied: the application time of the first voltage≤the application time of the second voltage.

In the blood component amount measurement method 3, the first voltage is, for example, 0.1 V to 1.0 V, preferably 0.2 V to 0.8 V, and more preferably 0.3 V to 0.6 V, the second voltage is, for example, 0.1 V to 1.0 V, preferably 0.2 V to 0.8 V, and more preferably 0.3 V to 0.6 V, the third voltage is, for example, 1.0 V to 5.0 V, preferably 1.5 to 4.5 V, and more preferably 2.0 to 4.0 V, and the fourth voltage is, for example, 1.0 V to 5.0 V, preferably 1.5 to 4.5 V, and more preferably 2.0 to 4.0 V. The following relationships are satisfied, for example: the third voltage>the first voltage and the third voltage>the second voltage. The application time of the first voltage is, for example, 0.05 to 2 seconds, preferably 0.1 to 1 second, and more preferably 0.1 to 0.3 seconds, the application time of the second voltage is, for example, 0.05 to 2 seconds, preferably 0.1 to 1 second, and more preferably 0.1 to 0.3 seconds, the application time of the third voltage is, for example, 0.05 to 1 second, preferably 0.1 to 0.5 seconds, and more preferably 0.1 to 0.3 seconds, and the application time of the fourth voltage is, for example, 0.05 to 1 second, preferably 0.1 to 0.5 seconds, and more preferably 0.1 to 0.3 seconds.

Fourth Embodiment: Blood Component Amount Measurement Method 4

The present invention provides a method (blood component amount measurement method 4) for measuring the amount of a blood component in blood using a biosensor, the biosensor including:
a first electrode system for measuring a blood component amount-dependent current value, the first electrode system including a first working electrode and a first counter electrode;
a third electrode system for measuring a hematocrit-dependent current value, the third electrode system including a third working electrode and a third counter electrode;
a fifth electrode system for measuring a hematocrit-dependent current value, the fifth electrode system including a fifth working electrode and a fifth counter electrode; and
a sixth electrode system for measuring a hematocrit-dependent current value, the sixth electrode system including a sixth working electrode and a sixth counter electrode,
wherein a first reagent layer is disposed on the first electrode system,
a second reagent layer is disposed on the fifth counter electrode of the fifth electrode system,
the first reagent layer and the second reagent layer are disposed spaced apart from each other,
the reagent layers are not disposed on the fifth working electrode of the fifth electrode system and the sixth working electrode of the sixth electrode system,
the first reagent layer and the second reagent layer each contain a reagent for measuring the amount of the blood component in the blood,
the fifth counter electrode is used as the third working electrode,
the first working electrode is used as the third counter electrode, and
one of the first working electrode and the first counter electrode is used as the sixth counter electrode,
the method including:
a first step of applying a first voltage to the first electrode system and detecting a first blood component amount-dependent current value;
a third step of applying a third voltage to the third electrode system and detecting a third hematocrit-dependent current value;
a fifth step of applying a fifth voltage to the fifth electrode system and detecting a fifth hematocrit-dependent current value;
a sixth step of applying a sixth voltage to the sixth electrode system and defecting a sixth hematocrit-dependent current value; and
a step of calculating the amount of the blood component using the first blood component amount-dependent current value, the third hematocrit-dependent current value, the fifth hematocrit-dependent current value, and the sixth hematocrit-dependent current value.

In the blood component amount measurement method 4, the first step may be performed at least twice, and two or more first blood component amount-dependent current values obtained may be used as the first blood component amount-dependent current values in the step of calculating the amount of the blood component. At this time, the first voltages may be different from each other. Alternatively, at this time, the first voltages may be equal to each other.

In the blood component amount measurement method 4, it is preferable that the third step, the fifth step, and the sixth step are performed after the first step.

In the blood component amount measurement method 4, the third step may be performed after the first step is performed at least once. In the fifth step, the first step may be performed at least once. The sixth step may be performed after the first step is performed at least once. In the blood component amount measurement method 1, the third step, the fifth step, and the sixth step each may be performed at least twice.

In the blood component amount measurement method 4, it is preferable that the first reagent layer and the second reagent layer each contain a mediator. The mediator is as described in the blood component amount measurement method 1.

In the blood component amount measurement method 4, it is preferable that the first reagent layer and the second reagent layer further contain an oxidoreductase. The oxidoreductase is as described in the blood component amount measurement method 1.

In the blood component amount measurement method 4, the first voltage is, for example, 0.1 V to 1.0 V, preferably 0.2 V to 0.8 V, and more preferably 0.3 V to 0.6 V. The application time of the first voltage is, for example, 0.05 to 2 seconds, preferably 0.1 to 1 second, and more preferably 0.1 to 0.3 seconds. When the first step is performed at least twice, the first voltages may be equal to or different from each other and the application times of the first voltage may be equal to or different from each other between the first steps.

In the blood component amount measurement method 4, the third voltage is, for example, 1.0 V to 5.0 V, preferably 1.5 to 4.5 V, and more preferably 2.0 to 4.0 V. The application time of the third voltage is, for example, 0.05 to 1 second, preferably 0.1 to 0.5 seconds, and more preferably 0.1 to 0.3 seconds. When the third step is performed at least twice, the third voltages may be equal to or different from each other and the application times of the third voltage may be equal to or different from each other between the third steps.

In the blood component amount measurement method 4, the fifth voltage is, for example, 1.0 V to 5.0 V, preferably 1.5 to 4.5 V, and more preferably 2.0 to 4.0 V. The application time of the fifth voltage is, for example, 0.05 to 1 second, preferably 0.1 to 0.5 seconds, and more preferably 0.1 to 0.3 seconds. When the fifth step is performed at least twice, the fifth voltages may be equal to or different from each other and the application times of the fifth voltage may be equal to or different from each other between the fifth steps.

In the blood component amount measurement method 4, the sixth voltage is, for example, 1.0 V to 5.0 V, preferably 1.5 to 4.5 V, and more preferably 2.0 to 4.0 V. The application time of the sixth voltage is, for example, 0.05 to 1 second, preferably 0.1 to 0.5 seconds, and more preferably 0.1 to 0.3 seconds. When the sixth step is performed at least twice, the sixth voltages may be equal to or different from each other and the application times of the sixth voltage may be equal to or different from each other between the sixth steps.

In the blood component amount measurement method 4, the first voltage and the third voltage preferably satisfy the following relationship: the third voltage>the first voltage. The first voltage and the fifth voltage preferably satisfy the following relationship: the fifth voltage>the first voltage. The first voltage and the sixth voltage preferably satisfy the following relationship: the sixth voltage>the first voltage.

In the blood component amount measurement method 4, the first voltage is, for example, 0.1 V to 1.0 V, preferably 0.2 V to 0.8 V, and more preferably 0.3 V to 0.6 V, the third voltage is, for example, 1.0 V to 5.0 V, preferably 1.5 to 4.5 V, and more preferably 2.0 to 4.0 V, the fifth voltage is, for example, 1.0 V to 5.0 V, preferably 1.5 to 4.5 V, and more preferably 2.0 to 4.0 V, and the sixth voltage is, for example, 1.0 V to 5.0 V, preferably 1.5 to 4.5 V, and more preferably 2.0 to 4.0 V. The following relationships are satisfied, for example: the third voltage>the first voltage, the fifth voltage>the first voltage, and the sixth voltage>the first voltage. The application time of the first voltage is, for example, 0.05 to 2 seconds, preferably 0.1 to 1 second, and more preferably 0.1 to 0.3 seconds, the application time of the third voltage is, for example, 0.05 to 1 second, preferably 0.1 to 0.5 seconds, and more preferably 0.1 to 0.3 seconds, the application time of the fifth voltage is, for example, 0.05 to 1 second, preferably 0.1 to 0.5 seconds, and more preferably 0.1 to 0.3 seconds, and the application time of the sixth voltage is, for example, 0.05 to 1 second, preferably 0.1 to 0.5 seconds, and more preferably 0.1 to 0.3 seconds.

Fifth Embodiment: Blood Component Amount Measurement Method 5

The present invention provides a method (blood component amount measurement method 5) according to the blood component amount measurement method 4,
wherein the biosensor further includes a seventh electrode system for measuring a hematocrit-dependent current value, the seventh electrode system including a seventh working electrode and a seventh counter electrode,
one of the fifth working electrode and the sixth working electrode is used as the seventh working electrode,
the fifth counter electrode is used as the seventh counter electrode,
the method further includes a seventh step of applying a seventh voltage to the seventh electrode system and detecting a seventh hematocrit-dependent current value, and
the step of calculating the amount of the blood component includes a step of calculating the amount of the blood component using the first blood component amount-dependent current value, the third hematocrit-dependent current value, the fifth hematocrit-dependent current value, the sixth hematocrit-dependent current value, and the seventh hematocrit-dependent current value.

In the blood component amount measurement method 5, the first step may be performed at least twice, and two or more first blood component amount-dependent current values obtained may be used as the first blood component amount-dependent current values in the step of calculating the amount of the blood component. At this time, the first voltages may be different from each other. Alternatively, at this time, the first voltages may be equal to each other.

In the blood component amount measurement method 5, it is preferable that the third step, the fifth step, and the sixth step are performed after the first step.

In the blood component amount measurement method 5, it is preferable that the seventh step is performed before the third step, the fifth step, and the sixth step.

In the blood component amount measurement method 5, it is preferable that the seventh step is performed after at least one of the first steps, and then the first step is further performed.

In the blood component amount measurement method 5, the third step may be performed after the first step is performed at least once. In the fifth step, the first step may be performed at least once. The sixth step may be performed after the first step is performed at least once. The seventh step may be performed after the first step is performed at least once. In the blood component amount measurement method 1, the third step, the fifth step, the sixth step, and the seventh step each may be performed at least twice.

In the blood component amount measurement method 5, it is preferable that the first reagent layer and the second reagent layer each contain a mediator. The mediator is as described in the blood component amount measurement method 1.

In the blood component amount measurement method 5, it is preferable that the first reagent layer and the second reagent layer further contain an oxidoreductase. The oxidoreductase is as described in the blood component amount measurement method 1.

In the blood component amount measurement method 5, the first voltage is, for example, 0.1 V to 1.0 V, preferably 0.2 V to 0.8 V, and more preferably 0.3 V to 0.6 V. The application time of the first voltage is, for example, 0.05 to 2 seconds, preferably 0.1 to 1 second, and more preferably 0.1 to 0.3 seconds. When the first step is performed at least twice, the first voltages may be equal to or different from each other and the application times of the first voltage may be equal to or different from each other between the first steps.

In the blood component amount measurement method 5, the third voltage is, for example, 1.0 V to 5.0 V, preferably 1.5 to 4.5 V, and more preferably 2.0 to 4.0 V. The application time of the third voltage is, for example, 0.05 to 1 second, preferably 0.1 to 0.5 seconds, and more preferably 0.1 to 0.3 seconds. When the third step is performed at least twice, the third voltages may be equal to or different from each other and the application times of the third voltage may be equal to or different from each other between the third steps.

In the blood component amount measurement method 5, the fifth voltage is, for example, 1.0 V to 5.0 V, preferably 1.5 to 4.5 V, and more preferably 2.0 to 4.0 V. The application time of the fifth voltage is, for example, 0.05 to 1 second, preferably 0.1 to 0.5 seconds, and more preferably 0.1 to 0.3 seconds. When the fifth step is performed at least twice, the fifth voltages may be equal to or different from each other and the application times of the fifth voltage may be equal to or different from each other between the fifth steps.

In the blood component amount measurement method 5, the sixth voltage is, for example, 1.0 V to 5.0 V, preferably 1.5 to 4.5 V, and more preferably 2.0 to 4.0 V. The application time of the sixth voltage is, for example, 0.05 to 1 second, preferably 0.1 to 0.5 seconds, and more preferably 0.1 to 0.3 seconds. When the sixth step is performed at least twice, the sixth voltages may be equal to or different from each other and the application times of the sixth voltage may be equal to or different from each other between the sixth steps.

In the blood component amount measurement method 5, the seventh voltage is, for example, 1.0 V to 5.0 V, preferably 1.5 to 4.5 V, and more preferably 2.0 to 4.0 V. The application time of the seventh voltage is, for example, 0.05 to 1 second, preferably 0.1 to 0.5 seconds, and more preferably 0.1 to 0.3 seconds. When the seventh step is performed at least twice, the seventh voltages may be equal to or different from each other and the application times of the seventh voltage may be equal to or different from each other between the seventh steps.

In the blood component amount measurement method 5, the first voltage and the third voltage preferably satisfy the following relationship: the third voltage>the first voltage. The first voltage and the fifth voltage may satisfy the following relationship: the fifth voltage>the first voltage. The first voltage and the sixth voltage may satisfy the following relationship: the sixth voltage>the first voltage. The first voltage and the seventh voltage may satisfy the following relationship: the seventh voltage>the first voltage.

In the blood component amount measurement method 5, the first voltage is, for example, 0.1 V to 1.0 V, preferably 0.2 V to 0.8 V, and more preferably 0.3 V to 0.6 V, the third voltage is, for example, 1.0 V to 5.0 V, preferably 1.5 to 4.5 V, and more preferably 2.0 to 4.0 V, the fifth voltage is, for example, 1.0 V to 5.0 V, preferably 1.5 to 4.5 V, and more preferably 2.0 to 4.0 V, the sixth voltage is, for example, 1.0 V to 5.0 V, preferably 1.5 to 4.5 V, and more preferably 2.0 to 4.0 V, and the seventh voltage is, for example, 1.0 V to 5.0 V, preferably 1.5 to 4.5 V, and more preferably 2.0 to 4.0 V. The following relationships are satisfied, for example: the third voltage>the first voltage, the fifth voltage>the first voltage, the sixth voltage>the first voltage, and the seventh voltage>the first voltage. The application time of the first voltage is, for example, 0.05 to 2 seconds, preferably 0.1 to 1 second, and more preferably 0.1 to 0.3 seconds, the application time of the third voltage is, for example, 0.05 to 1 second, preferably 0.1 to 0.5 seconds, and more preferably 0.1 to 0.3 seconds, the application time of the fifth voltage is, for example, 0.05 to 1 second, preferably 0.1 to 0.5 seconds, and more preferably 0.1 to 0.3 seconds, the application time of the sixth voltage is, for example, 0.05 to 1 second, preferably 0.1 to 0.5 seconds, and more preferably 0.1 to 0.3 seconds, and the application time of the seventh voltage is, for example, 0.05 to 1 second, preferably 0.1 to 0.6 seconds, and more preferably 0.1 to 0.3 seconds.

Sixth Embodiment: Blood Component Amount Measurement Method 6

The present invention provides a method (blood component amount measurement method 6) according to the blood component amount measurement method 4,
  wherein the biosensor further includes a second electrode system for measuring a blood component amount-dependent current value, the second electrode system including a second working electrode and a second counter electrode,
  the second reagent layer is also disposed on the second electrode system,
  the method further includes a second step of applying a second voltage to the second electrode system and detecting a second blood component amount-dependent current value, and
  the step of calculating the amount of the blood component includes a step of calculating the amount of the blood component using the first blood component amount-dependent current value, the second blood component amount-dependent current value, the third hematocrit-dependent current value, the fifth hematocrit-dependent current value, and the sixth hematocrit-dependent current value.

In the blood component amount measurement method 6, the first step may be performed at least twice, and two or more first blood component amount-dependent current values obtained may be used as the first blood component amount-dependent current values in the step of calculating the amount of the blood component. At this time, the first voltages may be different from each other. Alternatively, at this time, the first voltages may be equal to each other.

In the blood component amount measurement method 6, the second step may be performed at least twice, and two or more second blood component amount-dependent current values obtained may be used as the second blood component amount-dependent current values in the step of calculating the amount of the blood component. At this time, the first voltages may be different from each other. Alternatively, at this time, the first voltages may be equal to each other.

In the blood component amount measurement method 6, the first step may be performed at least twice, the second step may be performed at least twice, and all of the first steps and the second steps may be performed simultaneously. At this time, the first voltages may be different from each other. Alternatively, at this time, the first voltages may be equal to each other. At this time, the second voltages may be different from each other. Alternatively, at this time, the second voltages may be equal to oath other. When the first voltages are equal to each other and the second voltages are equal to each other, the first voltage and the second voltage may be equal to each other. Alternatively, when the first voltages are equal to each other and the second voltages are equal to each other, the first voltage and the second voltage may be different from each other.

In the blood component amount measurement method 6, the first step may be performed at least twice, the second step may be performed at least twice, and portions of the first steps and the second steps may be performed simultaneously. At this time, the first voltages may be different from each other. Alternatively, at this time, the first voltages may be equal to each other. At this time, the second voltages may be different from each other. Alternatively, at this time, the second voltages may be equal to each other. When the first voltages are equal to each other and the second voltages are equal to each other, the first voltage and the second voltage may be equal to each other. Alternatively, when the first voltages are equal to each other and the second voltages are equal to each other the first voltage and the second voltage may be different from each other.

In the blood component amount measurement method 6, it is preferable that the third step, the fifth step, and the sixth step are performed after the first step and the second step.

In the blood component amount measurement method 6, the third step may be performed after the first step is performed at least once. Also, in the fifth step, the first step may be performed at least once. Also, the sixth step may be performed after the first step is performed at least once.

In the blood component amount measurement method 6, the third step may be performed after the second step is performed at least once. Also, in the fifth step, the second step may be performed at least once. Also, the sixth step may be performed after the second step is performed at least once. In the blood component amount measurement method 6, the third step, the fifth step, and the sixth step each may be performed at least twice.

In the blood component amount measurement method 6, it is preferable that the first reagent layer and the second reagent layer each contain a mediator. The mediator is as described in the blood component amount measurement method 1.

In the blood component amount measurement method 6, it is preferable that the first reagent layer and the second reagent layer further contain an oxidoreductase. The oxidoreductase is as described in the blood component amount measurement method 1.

In the blood component amount measurement method 6, the first voltage is, for example, 0.1 V to 1.0 V, preferably 0.2 V to 0.8 V, and more preferably 0.3 V to 0.6 V. The application time of the first voltage is, for example, 0.05 to 2 seconds, preferably 0.1 to 1 second, and more preferably 0.1 to 0.3 seconds. When the first step is performed at least twice, the first voltages may be equal to or different from each other and the application times of the fast voltage may be equal to or different from each other between the first steps.

In the blood component amount measurement method 6, the second voltage is, for example, 0.1 V to 1.0 V, preferably 0.2 V to 0.8 V, and more preferably 0.3 V to 0.6 V. The application time of the second voltage is, for example, 0.05 to 2 seconds, preferably 0.1 to 1 second, and more preferably 0.1 to 0.3 seconds. When the second step is performed at least twice, the second voltages may be equal to or different from each other and the application times of the second voltage may be equal to or different from each other between the second steps.

In the blood component amount measurement method 6, the third voltage is, for example, 1.0 V to 5.0 V, preferably 1.5 to 4.5 V, and more preferably 2.0 to 4.0 V. The application time of the third voltage is, for example, 0.05 to 1 second, preferably 0.1 to 0.5 seconds, and more preferably 0.1 to 0.3 seconds. When the third step is performed at least twice, the third voltages may be equal to or different from each other and the application times of the third voltage may be equal to or different from each other between the third steps.

In the blood component amount measurement method 6, the fifth voltage is, for example, 1.0 V to 6.0 V, preferably 1.5 to 4.5 V, and more preferably 2.0 to 4.0 V. The application time of the fifth voltage is, for example, 0.05 to 1 second, preferably 0.1 to 0.5 seconds, and more preferably 0.1 to 0.3 seconds. When the fifth step is performed at least twice, the fifth voltages may be equal to or different from each other and the application times of the fifth voltage may be equal to or different from each other between the fifth steps.

In the blood component amount measurement method 6, the sixth voltage is, for example, 1.0 V to 5.0 V, preferably 1.5 to 4.5 V, and more preferably 2.0 to 4.0 V. The application time of the sixth voltage is, for example, 0.05 to 1 second, preferably 0.1 to 0.5 seconds, and more preferably 0.1 to 0.3 seconds. When the sixth step is performed at least twice, the sixth voltages may be equal to or different from each other and the application times of the sixth voltage may be equal to or different from each other between the sixth steps.

In the blood component amount measurement method 6, the first voltage and the third voltage preferably satisfy the following relationship: the third voltage>the first voltage. The first voltage and the fifth voltage preferably satisfy the following relationship: the fifth voltage>the first voltage. The first voltage and the sixth voltage preferably satisfy the following relationship: the sixth voltage>the first voltage.

In the blood component amount measurement method 6, the second voltage and the third voltage preferably satisfy the following relationship: the third voltage>the second voltage. The second voltage and the fifth voltage preferably satisfy the following relationship: the fifth voltage>the second voltage. The second voltage and the sixth voltage preferably satisfy the following relationship: the sixth voltage>the second voltage.

In the blood component amount measurement method 6, the first voltage is, for example, 0.1 V to 1.0 V, preferably 0.2 V to 0.8 V, and more preferably 0.3 V to 0.6 V, the second voltage is, for example, 0.1 V to 1.0 V, preferably 0.2 V to 0.8 V, and more preferably 0.3 V to 0.6 V, the third voltage is, for example, 1.0 V to 5.0 V, preferably 1.5 to 4.5 V, and more preferably 2.0 to 4.0 V, the fifth voltage is, for example, 1.0 V to 5.0 V, preferably 1.5 to 4.5 V, and more preferably 2.0 to 4.0 V, and the sixth voltage is, for example, 1.0 V to 5.0 V, preferably 1.5 to 4.5 V, and more preferably 2.0 to 4.0 V. The following relationships are satisfied, for example: the third voltage>the first voltage, the fifth voltage>the first voltage, the sixth voltage>the first voltage, the third voltage>the second voltage, the fifth voltage>the second voltage, and the sixth voltage>the second voltage. The application time of the first voltage is, for example, 0.05 to 2 seconds, preferably 0.1 to 1 second, and more preferably 0.1 to 0.3 seconds, the application time of the second voltage is, for example, 0.05 to 2 seconds, preferably 0.1 to 1 second, and more preferably 0.1 to 0.3 seconds, the application time of the third voltage is, for example, 0.05 to 1 second, preferably 0.1 to 0.5 seconds, and more preferably 0.1 to 0.3 seconds, the application time of the fifth voltage is, for example, 0.05 to 1 second, preferably 0.1 to 0.5 seconds, and more preferably 0.1 to 0.3 seconds, and the application time of the sixth voltage is, for example, 0.05 to 1 second, preferably 0.1 to 0.5 seconds, and more preferably 0.1 to 0.3 seconds.

Seventh Embodiment: Blood Component Amount Measurement Method 7

The present invention provides a method (blood component amount measurement method 7) affording to the blood component amount measurement method 6,
  wherein the biosensor further includes a seventh electrode system for measuring a hematocrit-dependent current value, the seventh electrode system including a seventh working electrode and a seventh counter electrode,
  one of the fifth working electrode and the sixth working electrode is used as the seventh working electrode,
  the fifth counter electrode is used as the seventh counter electrode,
  the method further includes a seventh step of applying a seventh voltage to the seventh electrode system and detecting a seventh hematocrit-dependent current value, and
  the step of calculating the amount of the blood component includes a step of calculating the amount of the blood component using the first blood component amount-dependent current value, the second blood component amount-dependent current value, the third hematocrit-dependent current value, the fifth hematocrit-dependent current value, the sixth hematocrit-dependent current value, and the seventh hematocrit-dependent current value.

In the blood component amount measurement method 7, it is preferable that the seventh step is performed before the third step, the fifth step, and the sixth step.

In the blood component amount measurement method 7, it is preferable that the seventh step is performed after the first step is performed at least once, and then the first step is further performed at least once.

In the blood component amount measurement method 7, the third step may be performed after the first step is performed at least once. In the fifth step, the first step may be performed at least once. The sixth step may be performed after the first step is performed at least once.

In the blood component amount measurement method 7, the third step may be performed after the second step is performed at least once. In the fifth step, the second step may be performed at least once. The sixth step may be performed after the second step is performed at least once.

In the blood component amount measurement method 7, the third step may be performed after the seventh step is performed at least once. In the fifth step, the seventh step may be performed at least once. The sixth step may be performed after the seventh step is performed at least once.

In the blood component amount measurement method 7, the third step, the fifth step, the sixth step, and the seventh step each may be performed at least twice.

In the blood component amount measurement method 7, it is preferable that the first reagent layer and the second reagent layer each contain a mediator. The mediator is as described in the blood component amount measurement method 1.

In the blood component amount measurement method 7, it is preferable that the first reagent layer and the second reagent layer further contain an oxidoreductase. The oxidoreductase is as described in the blood component amount measurement method 1.

In the blood component amount measurement method 7, the first voltage is, for example, 0.1 V to 1.0 V, preferably 0.2 V to 0.8 V, and more preferably 0.3 V to 0.6 V. The application time of the first voltage is, for example, 0.05 to 2 seconds, preferably 0.1 to 1 second, and more preferably 0.1 to 0.3 seconds. When the first step is performed at least twice, the first voltages may be equal to or different from each other and the application times of the first voltage may be equal to or different from each other between the first steps.

In the blood component amount measurement method 7, the second voltage is, for example, 0.1 V to 1.0 V, preferably 0.2 V to 0.8 V, and more preferably 0.3 V to 0.6 V. The application time of the second voltage is, for example, 0.05 to 2 seconds, preferably 0.1 to 1 second, and more preferably 0.1 to 0.3 seconds. When the second step is performed at least twice, the second voltages may be equal to or different from each other and the application times of the second voltage may be equal to or different from each other between the second steps.

In the blood component amount measurement method 7, the third voltage is, for example, 1.0 V to 5.0 V, preferably 1.5 to 4.5 V, and more preferably 2.0 to 4.0 V. The application time of the third voltage is, for example, 0.05 to 1 second, preferably 0.1 to 0.5 seconds, and more preferably 0.1 to 0.3 seconds. When the third step is performed at least twice, the third voltages may be equal to or different from each other and the application times of the third voltage may be equal to or different from each other between the third steps.

In the blood component amount measurement method 7, the fifth voltage is, for example, 1.0 V to 5.0 V, preferably 1.5 to 4.5 V, and more preferably 2.0 to 4.0 V. The application time of the fifth voltage is, for example, 0.05 to 1 second, preferably 0.1 to 0.5 seconds, and more preferably 0.1 to 0.3 seconds. When the fifth step is performed at least twice, the fifth voltages may be equal to or different from each other and the application times of the fifth voltage may be equal to or different from each other between the fifth steps.

In the blood component amount measurement method 7, the sixth voltage is, for example, 1.0 V to 5.0 V, preferably 1.5 to 4.5 V, and more preferably 2.0 to 4.0 V. The application time of the sixth voltage is, for example, 0.05 to 1 second, preferably 0.1 to 0.5 seconds, and more preferably 0.1 to 0.3 seconds. When the sixth step is performed at least twice, the sixth voltages may be equal to or different from each other and the application times of the sixth voltage may be equal to or different from each other between the sixth steps.

In the blood component amount measurement method 7, the seventh voltage is, for example, 1.0 V to 6.0 V, preferably 1.5 to 4.5 V, and more preferably 2.0 to 4.0 V. The application time of the sixth voltage is, for example, 0.05 to 1 second, preferably 0.1 to 0.5 seconds, and more preferably 0.1 to 0.3 seconds. When the seventh step is performed at least twice, the seventh voltages may be equal to or different from each other and the application times of the seventh voltage may be equal to or different from each other between the seventh steps.

In the blood component amount measurement method 7, the first voltage and the third voltage preferably satisfy the following relationship: the third voltage>the first voltage. The first voltage and the fifth voltage preferably satisfy the following relationship: the fifth voltage>the first voltage. The first voltage and the sixth voltage preferably satisfy the following relationship: the sixth voltage>the first voltage. The first voltage and the seventh voltage preferably satisfy the following relationship: the seventh voltage>the first voltage.

In the blood component amount measurement method 7, the second voltage and the third voltage preferably satisfy the following relationship: the third voltage>the second voltage. The second voltage and the fifth voltage preferably satisfy the following relationship: the fifth voltage>the second voltage. The second voltage and the sixth voltage preferably satisfy the following relationship: the sixth voltage>the second voltage. The second voltage and the seventh voltage preferably satisfy the following relationship: the seventh voltage>the second voltage.

In the blood component amount measurement method 7, the application time of the first voltage may be longer than the application time of the third voltage. The application time of the first voltage may be longer than the application time of the fourth voltage. The application time of the first voltage may be longer than the application time of the sixth voltage. The application time of the first voltage may be longer than the application time of the seventh voltage.

In the blood component amount measurement method 7, the application time of the second voltage may be longer than the application time of the third voltage. The application time of the second voltage may be longer than the application time of the fourth voltage. The application time of the second voltage may be longer than the application time of the sixth voltage. The application time of the second voltage may be longer than the application time of the seventh voltage.

In the blood component amount measurement method 7, the first voltage is, for example, 0.1 V to 1.0 V, preferably 0.2 V to 0.8 V, and more preferably 0.3 V to 0.6 V, the second voltage is, for example, 0.1 V to 1.0 V, preferably 0.2 V to 0.8 V, and more preferably 0.3 V to 0.6 V, the third voltage is, for example, 1.0 V to 5.0 V, preferably 1.5 to 4.5 V, and more preferably 2.0 to 4.0 V, the fifth voltage is, for example, 1.0 V to 5.0 V, preferably 1.5 to 4.5 V, and more preferably 2.0 to 4.0 V, the sixth voltage is, for example, 1.0 V to 5.0 V, preferably 1.5 to 4.5 V, and more preferably 2.0 to 4.0 V, and the seventh voltage is, for example, 1.0 V to 5.0 V, preferably 1.5 to 4.5 V, and more preferably 2.0 to 4.0 V. The following relationships are satisfied, for example: the third voltage>the first voltage, the fifth voltage>the first voltage, the sixth voltage>the first voltage, the seventh voltage>the first voltage, the third voltage>the second voltage, the fifth voltage>the second voltage, and the sixth voltage>the second voltage, and the seventh voltage>the second voltage. The application time of the first voltage is, for example, 0.05 to 2 seconds, preferably 0.1 to 1 second, and more preferably 0.1 to 0.3 seconds, the application time of the second voltage is, for example, 0.05 to 2 seconds, preferably 0.1 to 1 second, and more preferably 0.1 to 0.3 seconds, the application time of the third voltage is, for example, 0.05 to 1 second, preferably 0.1 to 0.5 seconds, and more preferably 0.1 to 0.3 seconds, the application time of the fifth voltage is, for example, 0.05 to 1 second, preferably 0.1 to 0.5 seconds, and more preferably 0.1 to 0.3 seconds, the application time of the sixth voltage is, for example, 0.05 to 1 second, preferably 0.1 to 0.5 seconds, and more preferably 0.1 to 0.3 seconds, and the application time of the seventh voltage is, for example, 0.05 to 1 second, preferably 0.1 to 0.5 seconds, and more preferably 0.1 to 0.3 seconds.

The biosensor used in the method for measuring a blood component of the present invention includes predetermined electrode systems as described above. Preferably, this biosensor further includes an insulating substrate on which the respective electrode systems and a channel for introducing blood into the respective electrode systems are formed, and one end of the channel is open to the outside of the biosensor to serve as a blood supply port. In thus case, the biosensor may be configured such that it has one blood supply port, the channel is branched at intermediate positions, and ends of the respective branched portions of the channel are in communication with respective analysis portions. Also, the biosensor may be configured such that the electrode systems are positioned at intermediate positions of the channel, and another electrode system is positioned rearward of these electrode systems.

The biosensor used in the method for measuring a blood component of the present invention is preferably configured such that it further includes a spacer and a cover, and the cover is disposed on the insulating substrate via the spacer.

In the biosensor used in the method for measuring a blood component of the present invention, when the reagent portions contain a mediator or contain a mediator and an oxidoreductase, it is preferable that the reagent portions further contain an enzyme stabilizer and/or a crystal homogenizing agent.

Examples of the enzyme stabilizer include sugar alcohols. Examples of the sugar alcohols include chain polyhydric alcohols and cyclic sugar alcohols, such as sorbitol, maltitol, xylitol, mannitol, lactitol, reduced palatinose, arabinitol, glycerol, ribitol, galactitol, sedoheptitol, perseitol, volemitol, styracitol, polygalitol, iditol, talitol, allitol, isylitol, saccharified reduced starch, and isylitol. Furthermore, stereoisomers, substitution products, or derivatives of these sugar alcohols may be used. These sugar alcohols may be used individually or two or more of them may be used together. Of these, maltitol is preferable. The amount of the enzyme stabilizer to be mixed is, for example, in the range from 0.1 to 500 mM, preferably in the range from 0.5 to 100 mM, and more preferably in the range from 1 to 50 mM per measurement or per sensor.

The crystal homogenizing agent is used to homogenize the crystal state in the reagent portions, and examples thereof include amino acids. Examples of the amino acids include glycine, alanine, valine, leucine, isoleucine, serine, threonine, methionine, asparagine, glutamine, arginine, lysine, histidine, phenylalanine, tryptophan, proline, sarcosine, betaine, and taurine, as well as salts, substitution products, and derivatives thereof. They may be used individually or two or more of them may be used together. Of these, glycine, serine, proline, threonine, lysine, and taurine are preferable, and taurine is more preferable. The amount of the crystal homogenizing agent to be mixed is, for example, 0.1 to 1000 mM, preferably 10 to 500 mM, and more preferably 20 to 200 mM per measurement or per sensor.

The biosensor used in the method for measuring a blood component of the present invention is preferably configured such that it further includes a blood detection electrode, the blood detection electrode is positioned rearward of at least one of the respective electrode systems from the blood supply port, and introduction of blood into at least one of the respective electrode systems can be reliably detected by the blood detection electrode. More preferably, the blood detection electrode is positioned rearward of all of the electrode systems. The blood detection electrode may be used as one of the electrode systems.

FIG. 2 is a perspective view showing an example of a measuring device with a biosensor used in the measurement method of the present invention being inserted thereinto. As shewn in FIG. 2, this measuring device 2 has an insertion port 5 for a sensor at one end thereof, and a sensor 3 is inserted thereinto and held therein. Reference numeral 10 denotes a blood supply port of the sensor 3. The measuring device 2 has a display portion 4 approximately at the center thereof, and a measurement result is displayed in the display portion 4.

Figure 62:
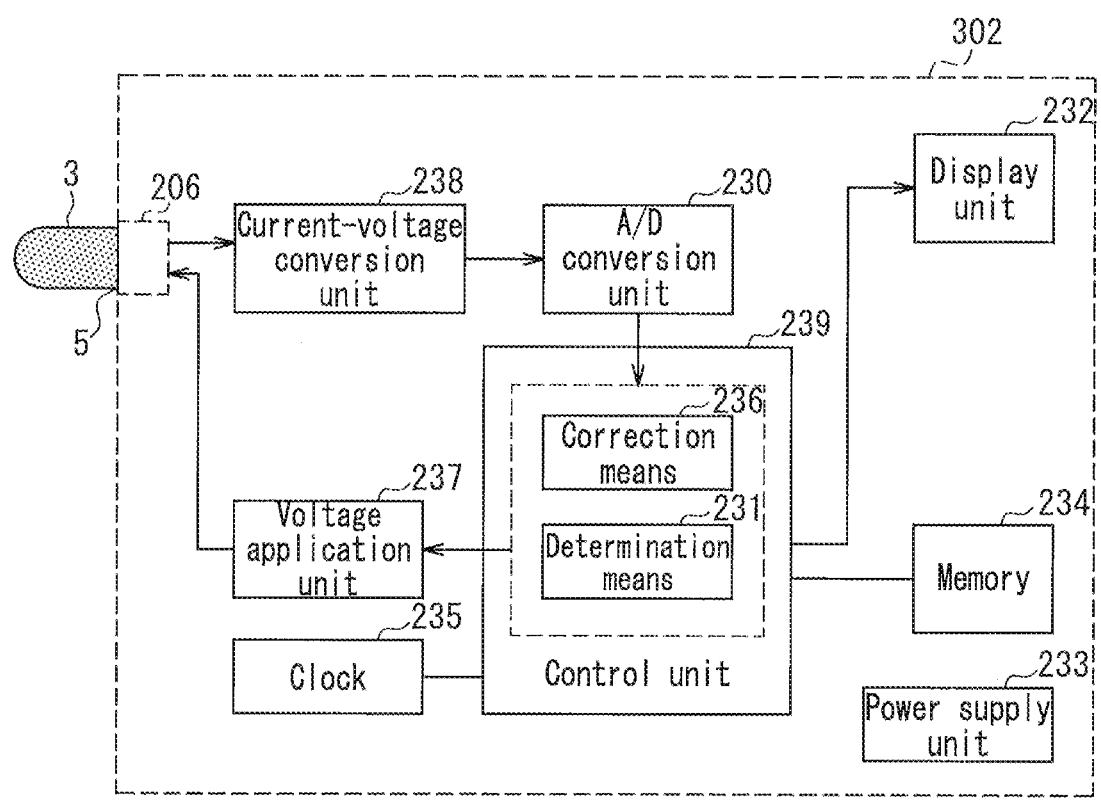
FIG. 62 is an electrical block diagram of a blood component measuring device with the biosensor used in the measurement method of the present invention being inserted thereinto.

FIG. 62 shows an example of an electrical block diagram of the measuring device 302 with the biosensor used in the measurement method of the present invention being inserted thereinto. In the measuring device of the present invention, a voltage application unit 237 for applying a voltage and a current-voltage conversion unit 238 are connected to an input terminal portion 206 of the measuring device according to an embodiment of the present invention. A voltage is applied to the voltage application unit 237 from a control unit 239, and this voltage is applied to desired electrodes selected from electrodes of respective electrode systems and a blood component introduction detection electrode of the biosensor 3 for a predetermined period of time through the input terminal portion 206. The current that flows between the electrodes in the biosensor 3 due to this voltage application is converted into a voltage by the current-voltage conversion unit 238. Thereafter, the voltage is subjected to digital conversion by an A/D conversion unit 230, and this digitized voltage is compared with a threshold value by a determination means 231.

A display unit 232 connected to the control unit 239 is configured to display the amount of a blood component detected by the biosensor 3 and the result of determination made by the determination means 231. In FIG. 62, reference numeral 233 denotes a power supply unit for supplying electric power to the above-described reactive units. Reference numeral 204 denotes a memory that is provided with a table including applied voltages, application times, etc. used when measuring the hematocrit and the blood component and a calibration curve and calibration table that are prepared beforehand based on environmental temperatures.

A dock 235 is connected to the control unit 239, and the control unit 239 is configured to execute various control operations utilizing the time indicated and the time measured by the clock 235. Furthermore, a correction means 236 is provided in the control unit 239. The correction means 236 corrects the measured amount of the blood component using the hematocrit, thereby improving the measurement accuracy of the amount of the blood component.

Next, examples of the method for measuring the amount of a blood component according to the present invention will be described with reference to the drawings.

Embodiment 1A

Embodiment 1A is an example of the blood component amount measurement method 1 of the present invention.

Figure 3:
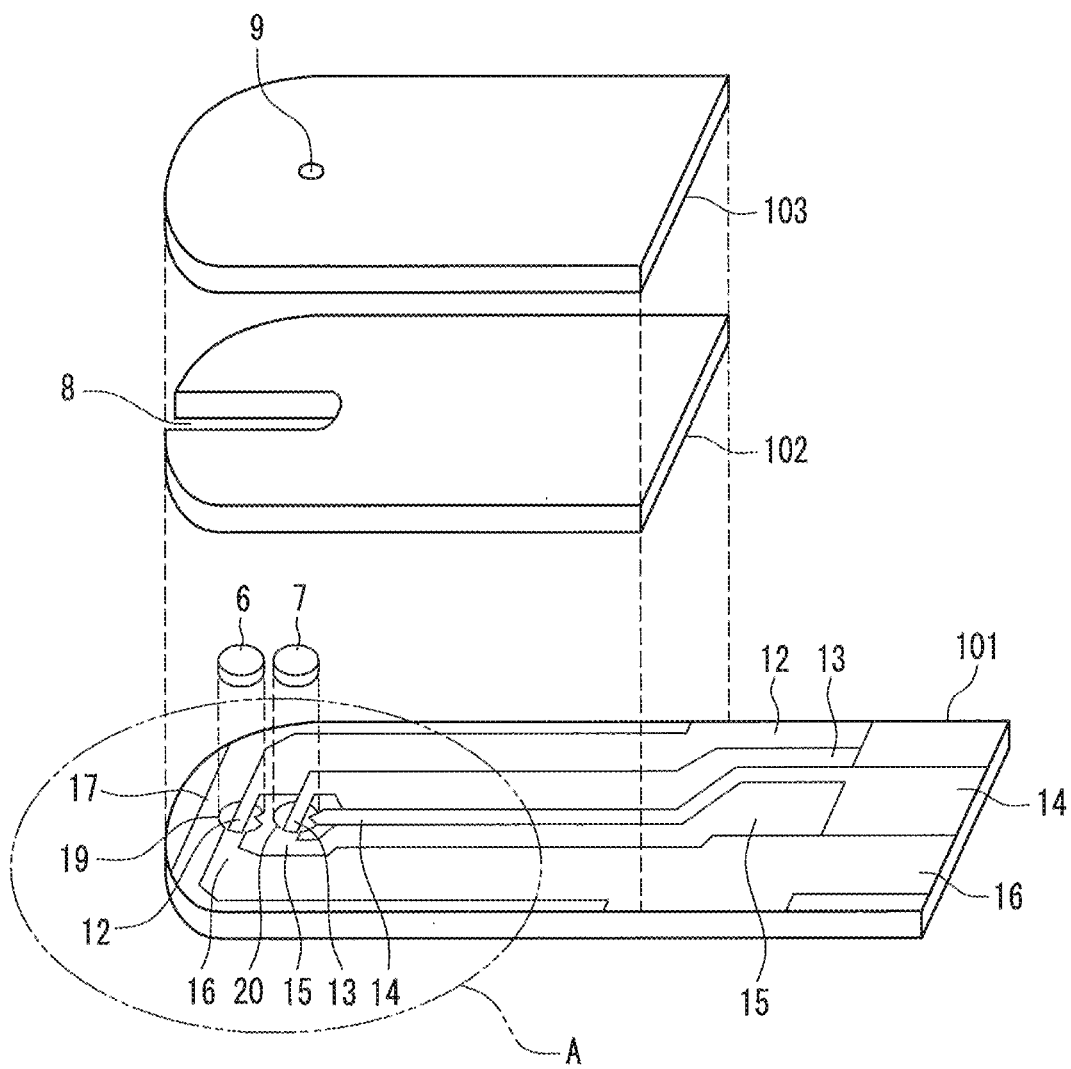
FIG. 3 is an exploded perspective view showing an example of a biosensor used in the measurement method of the present invention.
Figure 4:
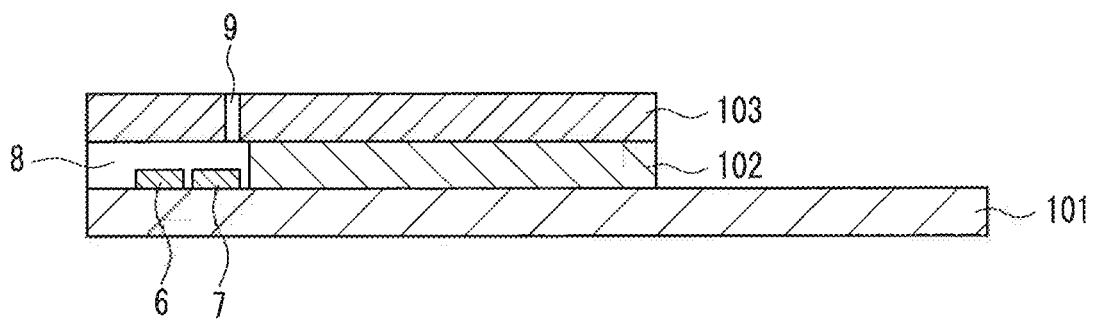
FIG. 4 is a cross-sectional view of the biosensor shown in FIG. 3.
Figure 5A:
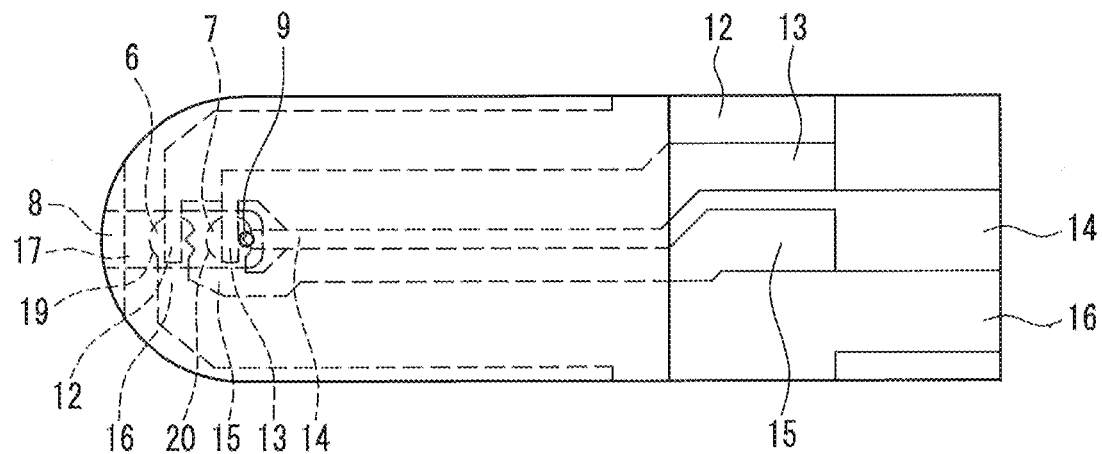
FIG. 5A is a plan view of the biosensor shown in FIG. 3.
Figure 5B:
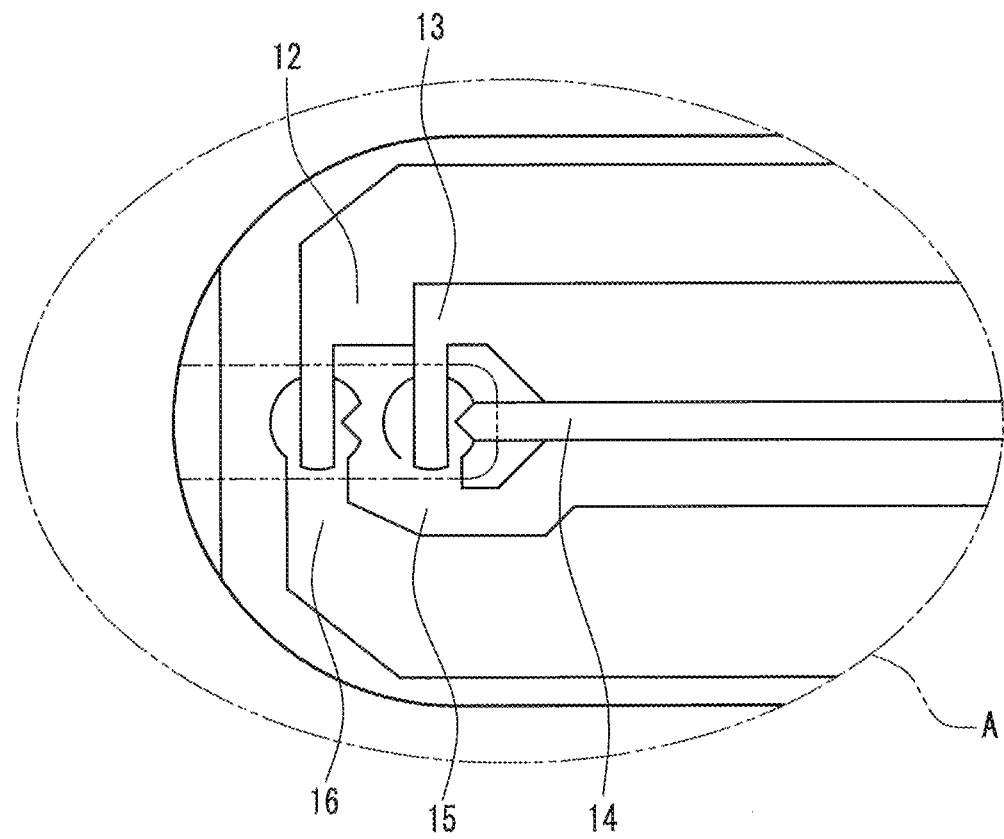
FIG. 5B is an enlarged view of a portion A shown in FIG. 3.

FIGS. 3, 4, 5A and 6B show an example of a biosensor (also referred to as "first biosensor" hereinafter) used in the measurement method of the present invention. FIG. 3 is an exploded perspective view of the first biosensor, FIG. 4 is a cross-sectional view of the biosensor shown in FIG. 3, FIG. 5A is a plan view of the biosensor shown in FIG. 3, and FIG. 5B is an enlarged view of a portion A shown in FIG. 3. In the above-described four drawings, the same components and portions are given the same reference numerals. As an illustrative example, this first biosensor is a sensor for measuring glucose as a blood component.

As shown in the drawings, in this first biosensor, six electrodes 12, 13, 14, 15, 16, and 17 are formed on an insulating substrate 101. These electrodes are each switchable between a working electrode and a counter electrode. The surface of the electrode 17 is coated with a polymer material such as CMC. A first reagent layer 6 is disposed so as to cover portions of the electrodes 12 and 16, and a second reagent layer 7 is disposed so as to cover portions of the electrodes 13, 14, and 15. The first reagent layer 6 and the second reagent layer 7 are disposed spaced apart from each other. The second reagent layer 7 contains a reagent for measuring the amount of a blood component in blood, preferably an oxidoreductase (e.g., glucose dehydrogenase), and more preferably an oxidoreductase and a mediator (e.g., potassium ferricyanide), and optionally contains an enzyme stabilizer, a crystal homogenizing agent, and/or the like. The first reagent layer preferably contains a mediator, and optionally contains an enzyme stabilizer, a crystal homogenizing agent, and the like.

A cover 103 is disposed on the insulating substrate 101 via a spacer 102 with one end of the insulating substrate 101 (the right end in the drawings) being left uncovered. In this first biosensor, in order to introduce blood to the respective electrodes (12, 13, 14, 15, 16, and 17), a channel 8 is formed by the insulating substrate 101, the spacer 102, and the cover 103. The leading end of this channel 8 extends to the other end of the first biosensor (the left end in the drawings) and is open to the outside to serve as a blood supply port 10. The six electrodes (12, 13, 14, 15, 16, and 17) are connected to leads, respectively, and these leads extend toward the above-described one end (the right end in the drawings), and leading ends of the leads are exposed without being covered by the cover. The cover 103 has an air hole 9 formed in a portion (on the second reagent layer 7 or on the electrode 14) corresponding to the right end of the channel 8. Furthermore, the electrode 17, the first reagent layer 6 and the second reagent layer 7 are disposed spaced apart from each other in the channel 8 at the location of the first reagent 19 and the location of the second reagent 20, respectively.

In the present invention, the material of the insulating substrate is not particularly limited. Examples of the material that can be used include polyethylene terephthalate (PET), polycarbonate (PC), polyimide (PI), polyethylene (PE), polypropylene (PP), polystyrene (PS), polyvinyl chloride (PVC), polyoxymethylene (POM), monomer-cast nylon (MC), polybutylene terephthalate (PBT), methacrylic resins (PMMA), ABS resin (ABS), and glass. Of these, polyethylene terephthalate (PET), polycarbonate (PC), and polyimide (PI) are preferable, and polyethylene terephthalate (PET) is more preferable. The size of the insulating substrate is not particularly limited, and the insulating substrate has, for example, an overall length of 5 to 100 mm, a width of 2 to 50 mm, and a thickness of 0.05 to 2 mm, preferably an overall length of 7 to 50 mm, a width of 3 to 20 mm, and a thickness of 0.1 to 1 mm, and more preferably an overall length of 10 to 30 mm, a width of 3 to 10 mm, and a thickness of 0.1 to 0.6 mm. The same applies to the material and the size of an insulating substrate in embodiments to be described below.

The electrodes and the leads on the insulating substrate can be formed by, for example, forming a conductive layer through sputtering or vapor deposition using a material such as gold, platinum, or palladium, and working the conductive layer into a specific electrode pattern using a laser. As the laser, a YAG laser, a $CO_2$ laser, an excimer laser, or the like can be used, for example. This also applies to the embodiments to be described below.

The second reagent layer 7 is formed in the following manner. For example, an aqueous solution containing 0.1 to 5 U/sensor of an oxidoreductase (e.g., glucose dehydrogenase), 10 to 200 mM of a mediator (e.g., potassium ferricyanide), 1 to 50 mM of an enzyme stabilizer (e.g., maltitol), and 20 to 200 mM of a crystal homogenizing agent (e.g., taurine) is applied dropwise to a circular slit portion and is then dried. The presence of this slit portion can suppress the spread of the aqueous solution applied dropwise, and this allows more accurate positioning of the reagent layer 7. Thus, the reagent layer 7 is formed so as to cover portions of the electrodes 13, 14, and 15. The drying may be, for example, natural drying or forced drying using warm air.

The first reagent layer 6 is formed in the following manner. For example, an aqueous solution containing 10 to 200 mM of a mediator (e.g., potassium ferricyanide) and 20 to 200 mM of a crystal homogenizing agent (e.g., taurine) is applied dropwise to a circular slit portion and is then dried. The presence of this slit portion can suppress the spread of the aqueous solution applied dropwise, and this allows more accurate positioning of the reagent layer 6. Thus, the reagent layer 6 is formed so as to cover portions of the electrodes 12 and 16. The drying may be, for example, natural drying or forced drying rising warm air.

In the present invention, the material of the spacer 102 is not particularly limited, and examples thereof include those given above as examples of the material of the insulating substrate. Furthermore, the size of the spacer is not particularly limited, and the spacer has, for example, an overall length of 5 to 100 mm, a width of 2 to 50 mm, and a thickness of 0.01 to 1 mm, preferably an overall length of 7 to 50 mm, a width of 3 to 20 mm, and a thickness of 0.05 to 0.5 mm, and more preferably an overall length of 10 to 30 mm, a width of 3 to 10 mm, and a thickness of 0.05 to 0.25 mm. The spacer of this example has an I-shaped cutout portion that forms the channel for blood introduction. The I-shaped cutout portion has, for example, an overall length of 0.5 to 8 mm and a width of 0.1 to 5 mm, preferably an overall length of 1 to 10 mm and a width of 0.2 to 3 mm, and more preferably an overall length of 1 to 5 mm and a width of 0.5 to 2 mm. This cutout portion may be formed through, for example, cutting with a laser, a drill, or the like, or forming the spacer using a mold with which the cutout portion can be formed. The same applies to the material and the size of a spacer and to a cutout portion in the embodiments to be described below.

In the present invention, the material of the cover 103 is not particularly limited. Examples of the material of the cover 103 include those given above as examples of the material of the insulating substrate. It is more preferable that a portion of the cover that forms the ceiling of the channel for blood introduction is subjected to hydrophilic treatment. The hydrophilic treatment may be performed using a method such as, for example, applying a surfactant or introducing a hydrophilic functional group such as a hydroxyl group, a carbonyl group, or a carboxyl group to the surface of the cover through plasma treatment or the like. Furthermore, a layer composed of a surfactant such as lecithin may be formed on the reagent layers. The size of the cover is not particularly limited. The cover has, for example, an overall length of 5 to 100 mm, a width of 3 to 50 mm, and a thickness of 0.01 to 0.5 mm, preferably an overall length of 10 to 50 mm, a width of 3 to 20 mm, and a thickness of 0.05 to 0.25 mm, and more preferably an overall length of 15 to 30 mm, a width of 5 to 10 mm, and a thickness of 0.05 to 0.1 mm. The cover preferably has the air hole 9 formed therein, and the shape of the air hole 9 is, for example, circular, oval, polygonal, or the like. The air hole 9 has, for example, a maximum diameter of 0.01 to 10 mm, preferably a maximum diameter of 0.05 to 5 mm, and more preferably a maximum diameter of 0.1 to 2 mm. The air hole may be formed by, for example, perforating the cover using a laser, a drill, or the like, or forming the cover using a mold with which an air vent portion can be formed. The same applies to the material and the size of a cover and to an air hole in the embodiments to be described below.

Moreover, this first biosensor can be produced by stocking the insulating substrate 101, the spacer 102, and the raver 103 in this order and integrating them. The above-described three members are integrated by attaching them together using an adhesive or through thermal fusion landing or the like. Examples of the adhesive that can be used include epoxy adhesives, acrylic adhesives, polyurethane adhesives, thermosetting adhesives (hot melt adhesives and the like), and UV curable adhesives. This also applies to the embodiments to be described below.

Measurement of the amount of a blood component, e.g., measurement of the blood glucose level using this first biosensor is carried out in the following manner. First, a fingertip or the like is pricked with a dedicated lancet to cause bleeding. Meanwhile, the first biosensor is set in a dedicated measuring device (meter). The blood supply port of the first biosensor set in the measuring device is brought into contact with the blood at the bleeding site, and the blood is introduced into the first biosensor through capillary action. The analysis using this first biosensor is carried out as per the following steps.

In Embodiment 1A, the electrode 12, the electrode 13, the electrode 14, the electrode 15, the electrode 16, and the electrode 17 of the first biosensor are used as an electrode A, an electrode C, an electrode D, an electrode E, an electrode G, and an electrode F, respectively. FIG. 14 shows which of the electrodes is used as the counter electrode and the working electrode of each of a first electrode system, a second electrode system, and a third electrode system.

Step A: Detection of Sample (Blood)

A voltage is applied between the electrode D and the electrode E, and the introduction of blood is detected based on a change in the current value accompanying the introduction of blood. After the introduction of the blood is detected, subsequent steps are started. The voltage applied in Step A is, for example, 0.05 to 1 V, and preferably 0.7 V. Then, glucose in the blood is allowed to react with glucose oxidoreductase for a certain period of time. It should be noted that Step A is optional.

Step B: Step of Measuring Blood Component Amount-Dependent Current Values

Figure 12:
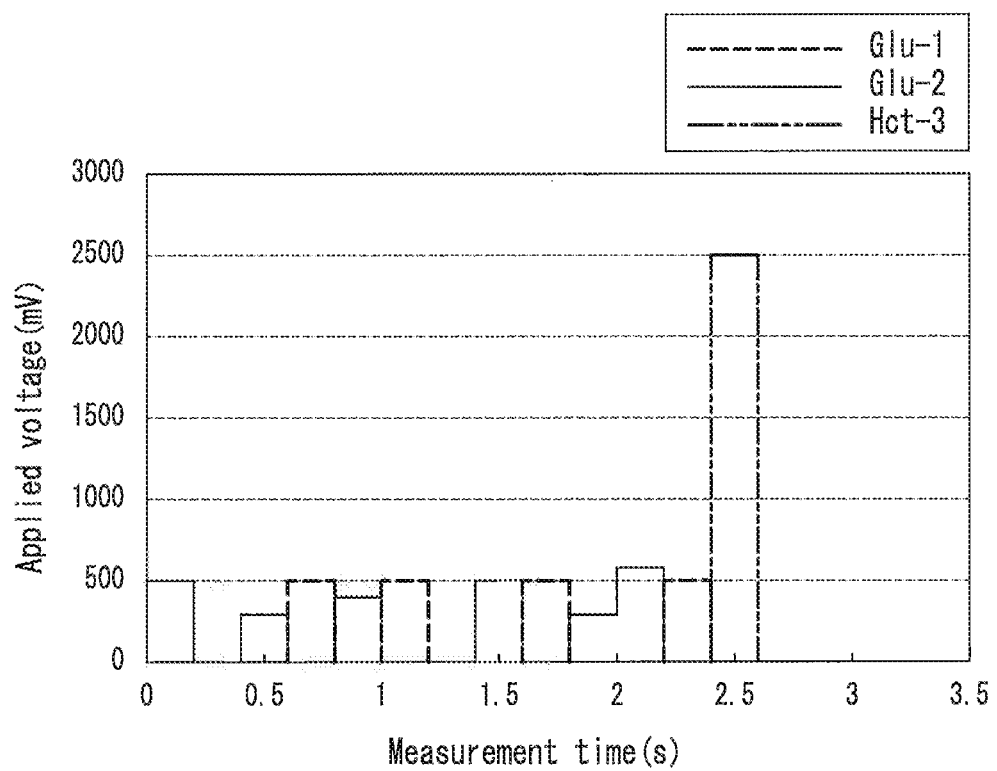
FIG. 12 is a diagram showing a change in voltage value over time in a voltage application pattern in Embodiment 1A.

As shown in FIG. 12, after the glucose in the blood has been reacted with the glucose oxidoreductase for a certain period of time, the measuring device 2 applies a voltage to the second electrode system while controlling the voltage value and the application time of a second voltage (second step). The measuring device 2 starts to measure the current when a detection electrode system (the electrode D and the electrode E) detects the blood to be measured after the blood has been introduced into the first biosensor 3.

At this time, the measuring device 2 changes the electrodes to be subjected to voltage application, the applied voltage, the application time, and the timing of voltage application as shown in FIG. 13. The second voltage is applied between the electrodes in the second electrode system (including the electrode A serving as the working electrode and the electrode G serving as the counter electrode). In FIG. 13, voltage application indicated with "Glu-2" corresponds to the voltage application in this second step. The second voltage is 300 mV to 500 mV. The second step of applying the second voltage to the second electrode system and detecting a second blood component amount-dependent current value is performed a plurality of times, e.g., six times.

In the case where the second step is performed at least twice, the second voltages may be different from each other. This is because the effects of interfering substances that react at different voltages can be observed.

In this Step B, after the second step, a voltage is applied to the first electrode system (including the electrode C serving as the working electrode and the electrodes D and E serving as the counter electrodes) while controlling the voltage value and the application time of a first voltage (first step). In FIG. 13, voltage application indicated with "Glu-1" corresponds to the voltage application in this first step. The first voltage is 500 mV. The first step of applying the first voltage to the first electrode system and detecting a first blood component amount-dependent current value is performed a plurality of times, e.g., four times. The first steps and the second steps are performed in turn as follows, for example: the second step, the second step, the first step, the second step, and so on. In the case where the first step is performed at least twice, the first voltages may be equal to each other. This is because, for example, transition of the response value (current value) on the time axis can be observed.

In this Step B, the first step may be performed at least twice, the second step may be performed at least twice, and the second steps and the first steps may be performed alternately.

In this Step B, the order of performing the first step and the second step may be changed. That is, although the second step is performed first in the example illustrated in FIG. 12, the first step may be performed first.

The first blood component amount-dependent current values obtained by applying the first voltage to the first electrode system and the second blood component amount-dependent current values obtained by applying the second voltage to the second electrode system are used in a step of calculating the amount of the blood component to be described below.

Step C: Step of Measuring Hct

As shown in FIG. 12, after performing the steps of measuring the blood component amount-dependent current values (the first step and the second step), the measuring device 2 applies a voltage to the third electrode system while controlling the voltage value and the application time of a third voltage (third step). Although Step B is performed first and then Step C is performed in this example, Step C may be performed first and then Step B may be performed.

At this time, the measuring device 2 changes the electrodes to be subjected to voltage application, the applied voltage, the application time, and the timing of voltage application as shown in FIG. 13. The third voltage is applied between the electrodes in the third electrode system (including the electrode A serving as the working electrode and the electrode C serving as the counter electrode). In FIG. 13, voltage application indicated with "Hct-3" corresponds to the voltage application in this step. The third voltage is 2500 mV. A third hematocrit-dependent current value obtained by applying the third voltage to the third electrode system is used in the step of calculating the amount of the blood component to be described below.

It should be noted that, in this embodiment, the electrode F that is coated with a polymer such as CMC only and on which the second reagent layer and the third reagent layer are not disposed, that is, a bare electrode, is not used.

Step D: Step of Calculating Amount of Blood Component

The plurality of, e.g., the plurality of blood component amount-dependent current values obtained are processed as follows before they are used as the blood component amount-dependent current values.

A plurality of parameters (x1, x2, x3, . . . , x10) are calculated based on, for example, the extracted current values measured at the plurality of predetermined time points and the extracted temperature information of the biological information measuring device ("calculate predetermined parameters"), a correction amount is calculated using a multiple regression equation (e.g., Formula 1 below), and then a blood component amount-dependent current value is calculated.

$$y = ax1 + bx2 + cx3 \ldots + kx10 + l \qquad \text{(Formula 1)}$$

(y denotes the correction amount, x1, x2, x3 . . . , and x10 denote parameters, and a, b, c, . . . and l denote coefficients.)

The amount of the blood component is obtained using the third Hct-dependent current value obtained in Step C and the blood component-dependent current values (the first and second blood component-dependent current values) obtained in Step B. Preferably, this is performed based on a calibration curve (including a calibration table) prepared beforehand. The thus-obtained amount of the blood component is displayed or stored in the measuring device.

After the amount of the blood component has been calculated, the first biosensor is discarded and the display unit and the like are turned off. Thereafter, the measuring device is also turned off to complete the measurement of the component of the biological sample.

According to this Embodiment 1A, by applying different voltages to the first and second electrode systems for measuring a blood component, the effects of interfering substances that react at different voltages can be reflected in the amount of the blood component to be finally obtained.

Embodiment 1B

Embodiment 1B is an example of the blood component amount measurement method 1 of the present invention.

The biosensor used in this method is the same as the first biosensor used in Embodiment 1A. In Embodiment 1B, the electrode 12, the electrode 13, the electrode 14, the electrode 15, the electrode 16, and the electrode 17 of the first biosensor are used as an electrode A, an electrode C, an electrode D, an electrode E, an electrode G, and an electrode F, respectively. FIG. 17 shows which of the electrodes is used as the counter electrode and the working electrode of each of a first electrode system, a second electrode system, and a third electrode system.

Figure 15:
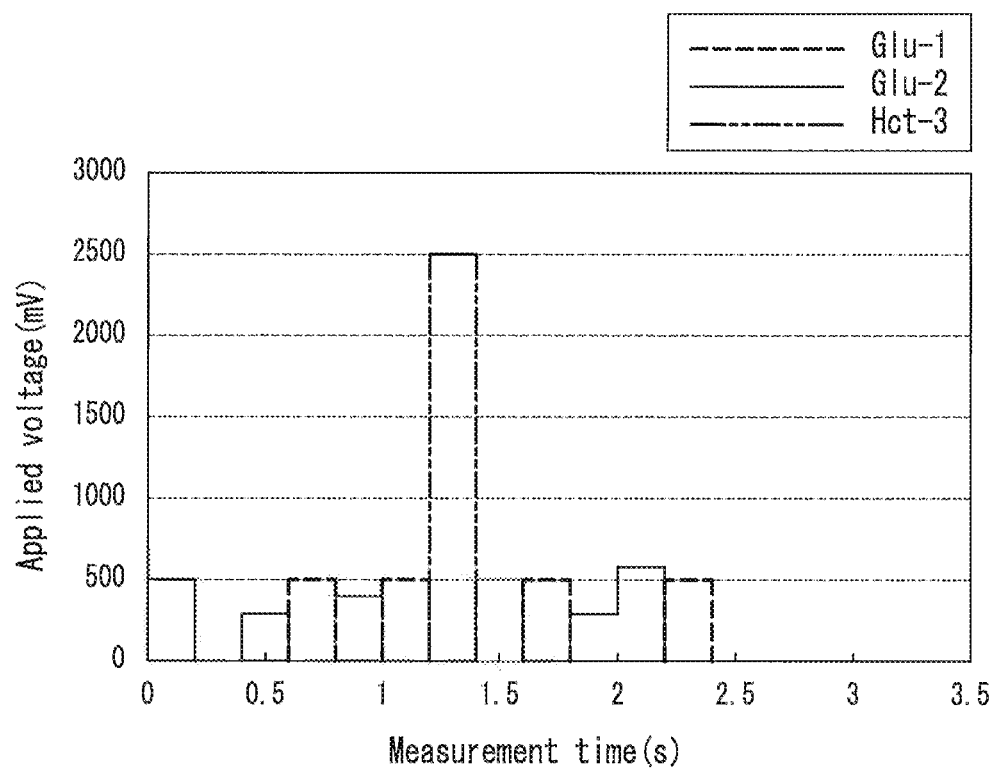
FIG. 15 is a diagram showing a change in voltage value over time in a voltage application pattern in Embodiment 1B.

In Embodiment 1B, the measuring device 2 changes the electrodes to be subjected to voltage application, the applied voltage, the application time, and the timing of voltage application as shown in FIG. 15. A second voltage is applied between the electrodes in the second electrode system (including the electrode A serving as the working electrode and the electrode G serving as the counter electrode). In FIG. 16, voltage application indicated with "Glu-2" corresponds to the voltage application in this second step. The second voltage is 500 mV. The second step of applying the second voltage to the second electrode system and detecting a second blood component amount-dependent current value is performed a plurality of times, e.g., six times. In this Step B, at the same time as the second step, a voltage is applied to the first electrode system while controlling the voltage value and the application time of a first voltage (first step). In FIG. 16, voltage application indicated with "Glu-1" corresponds to the voltage application in this first step. The first voltage is 300 to 600 mV. The first step of applying the first voltage to the first electrode system and detecting a first blood component amount-dependent current value is performed a plurality of times, e.g., four times.

As shown in FIG. 16, after performing the steps of measuring the blood component amount-dependent current values (the first step and the second step), the measuring device 2 applies a voltage to the third electrode system while controlling the voltage value and the application time of a third voltage (third step). Embodiment 1B is the same as Embodiment 1A, except that the steps of measuring the blood component amount-dependent current values (the first step and the second step) are also performed after the third step.

In this Embodiment 1B, a hematocrit-dependent current value can be detected using, as the working electrode and the counter electrode in the third electrode system (Hct-3), the electrodes used as the counter electrodes in the first electrode system (Glu-1) and the second electrode system (Glu-2) shown in FIG. 17. Although, in FIG. 17, the electrode D and the electrode G are used as the working electrode and the counter electrode in the third electrode system (Hct-3), respectively, the electrode E, which is one of the counter electrodes in the first electrode system, may also be used as the working electrode or the counter electrode in the third electrode system. Since the electrodes used as the counter electrodes in the first electrode system (Glu-1) and the second electrode system (Glu-2) are used as the working electrode and the counter electrode in the third electrode system (Hct-3), there is little effect of the glucose measurement. Accordingly, the third step of detecting the third hematocrit-dependent current value can be performed while the first step of detecting the first blood component amount-dependent current value and the second step of detecting the second blood component amount-dependent current value are being performed.

Embodiment 1C

Embodiment 1C is an example of the blood component amount measurement method 1 of the present invention.

Figure 6:
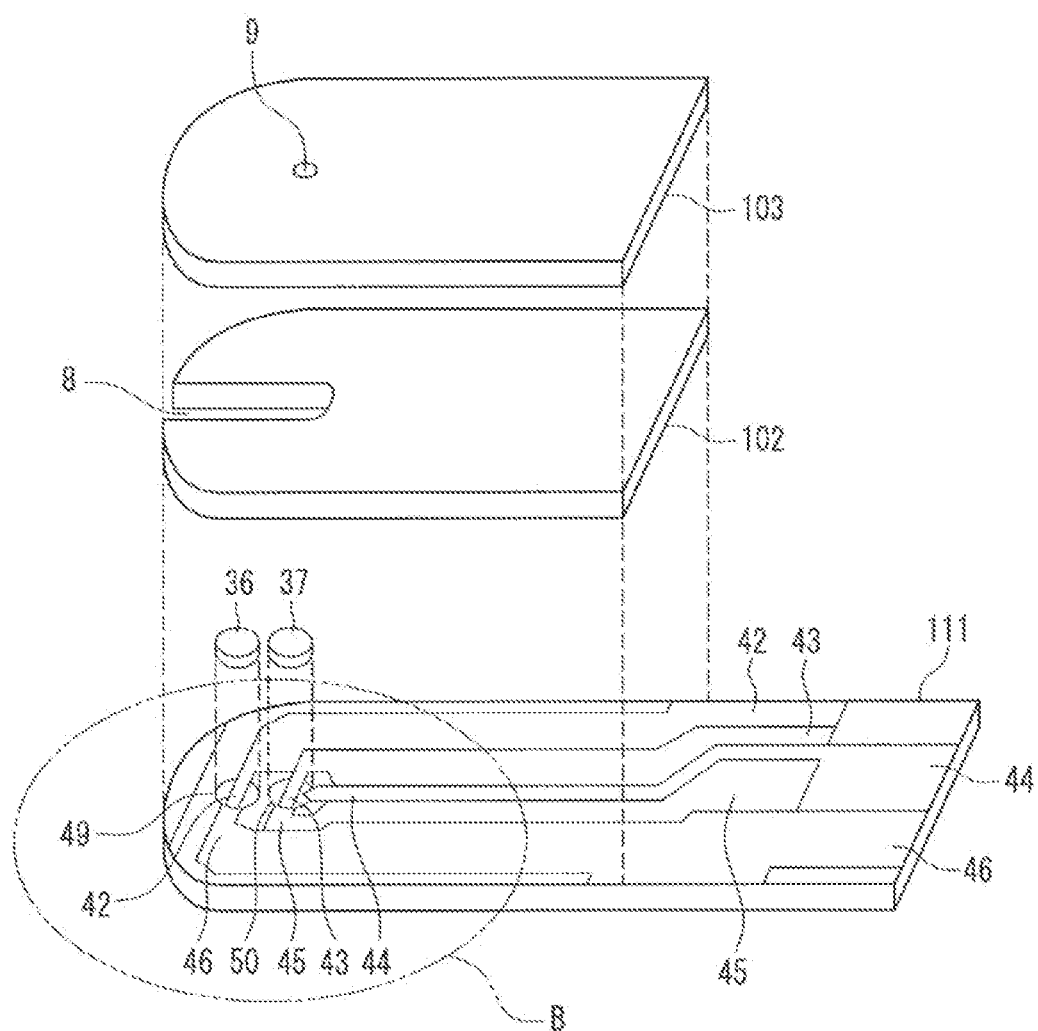
FIG. 6 is an exploded perspective view showing another example of the biosensor used in the measurement method of the present invention.
Figure 7:
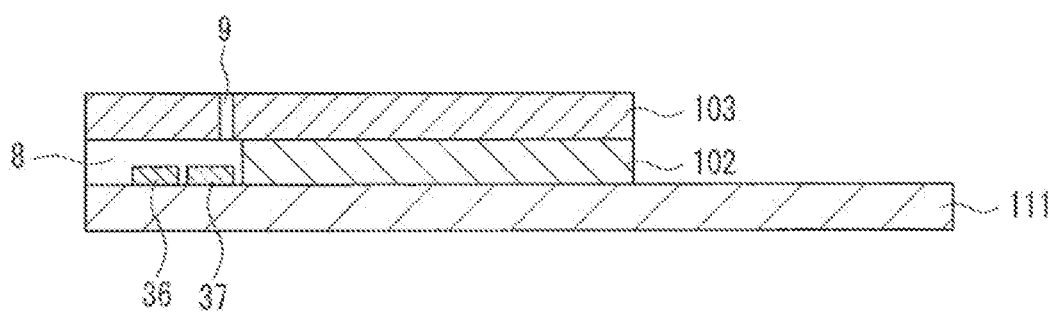
FIG. 7 is a cross-sectional view of the biosensor shown in FIG. 6.
Figure 8A:
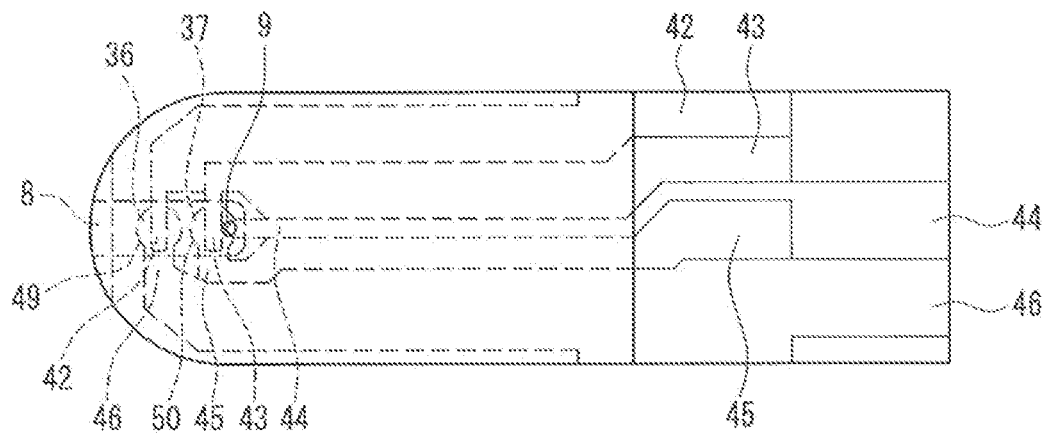
FIG. 8A is a plan view of the biosensor shown in FIG. 6.
Figure 8B:
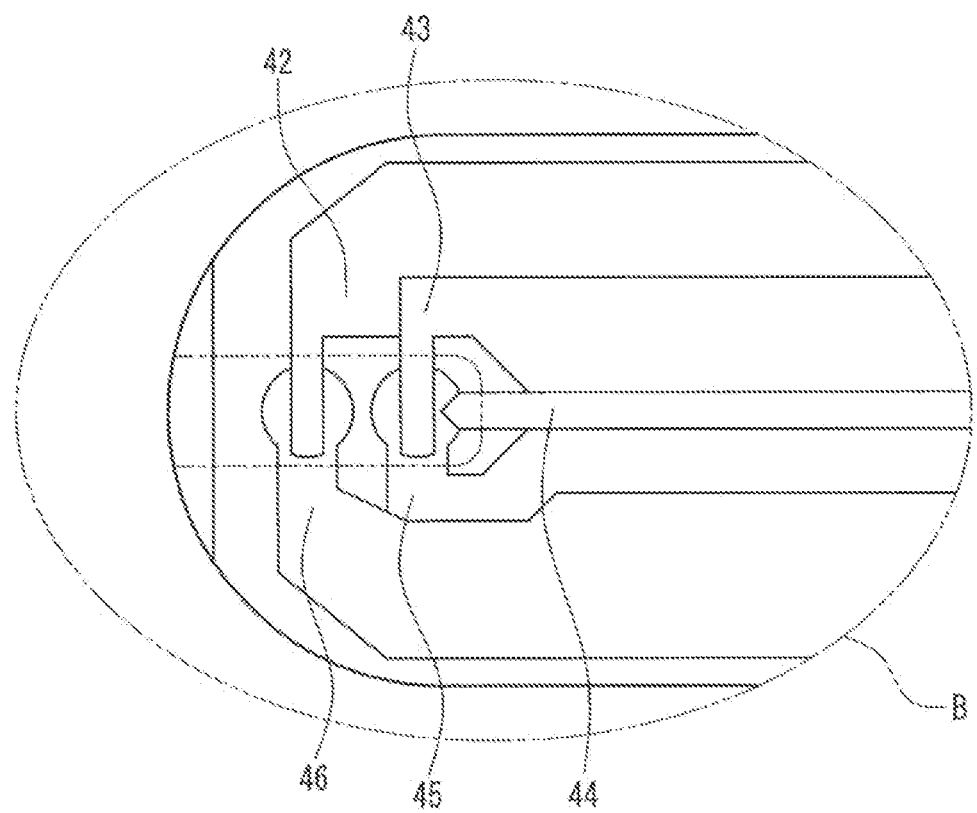
FIG. 8B is an enlarged view of a portion B shown in FIG. 6.

FIGS. 6, 7, 8A and 8B show another example of the biosensor (also referred to as "second biosensor" hereinafter) used in the measurement method of the present invention. FIG. 6 is an exploded perspective view of the second biosensor, FIG. 7 is a cross-sectional view of the biosensor shown in FIG. 6, FIG. 8A is a plan view of the biosensor shown in FIG. 6, and FIG. 8B is an enlarged view of a portion B shown in FIG. 6. In the above-described four drawings, the same components and portions are given the same reference numerals. As an illustrative example, this second biosensor is a sensor for measuring glucose as a blood component.

As shown in the drawings, in this second biosensor, five electrodes 42, 43, 44, 45, and 46 are formed on an insulating substrate 111. These electrodes are each switchable between a working electrode and a counter electrode. The surfaces of the electrodes 42, 43, 44, 45, and 46 are coated with a polymer material such as CMC. A first reagent layer 36 is disposed so as to cover portions of the electrodes 42 and 46 at the location of the first reagent 49, and a second reagent layer 37 is disposed so as to cover portions of the electrodes 43, 44, and 45 at the location of the second reagent 50. The first reagent layer 36 and the second reagent layer 37 are disposed spaced apart from each other. The first reagent layer contains a reagent for measuring the amount of a blood component in blood, preferably an oxidoreductase (e.g., glucose dehydrogenase), and more preferably an oxidoreductase and a mediator (e.g., potassium ferricyanide), and optionally contains an enzyme stabilizer, a crystal homogenizing agent, and/or the like. The second reagent layer contains a reagent for measuring the amount of a blood component in blood, preferably an oxidoreductase (e.g., glucose dehydrogenase), and more preferably an oxidoreductase and a mediator (e.g., potassium ferricyanide), and optionally contains an enzyme stabilizer, a crystal homogenizing agent, and/or the like.

A cover 103 is disposed on the insulating substrate 111 via a spacer 102 with one end of the insulating substrate 111 (the right end in the drawings) being left uncovered. In this second biosensor, in order to introduce blood to the respective electrodes (42, 43, 44, 45, and 46), a channel 8 is formed by the insulating substrate 111, the spacer 102, and the cover 103. The leading end of this channel 8 extends to the other end of the second biosensor (the left end in the drawings) and is open to the outside to serve as a blood supply port 10. The five electrodes (42, 43, 44, 45, and 46) are connected to leads, respectively, and these leads extend toward the above-described one end (the right end in the drawings), and leading ends of the leads are exposed without being covered by the cover. The cover 103 has an air hole 9 formed in a portion (on the second reagent layer 37 or on the electrode 44) corresponding to the right end of the channel 8. Furthermore, the first reagent layer 36 and the second reagent layer 37 are disposed spaced apart from each other in the channel 8 at the location of the first reagent 49 and the location of the second reagent 50, respectively.

In the present invention, the material of the insulating substrate is not particularly limited. Examples of the material that can be used include polyethylene terephthalate (PET), polycarbonate (PC), polyimide (PI), polyethylene (PE), polypropylene (PP), polystyrene (PS), polyvinyl chloride (PVC), polyoxymethylene (POM), monomer-cast nylon (MC), polybutylene terephthalate (PBT), methacrylic resins (PMMA), ABS resin (ABS), and glass. Of these, polyethylene terephthalate (PET), polycarbonate (PC), and polyimide (PI) are preferable, and polyethylene terephthalate (PET) is more preferable. The size of the insulating substrate is not particularly limited, and the insulating substrate has, for example, an overall length of 5 to 100 mm, a width of 2 to 50 mm, and a thickness of 0.05 to 2 mm, preferably an overall length of 7 to 50 mm, a width of 3 to 20 mm, and a thickness of 0.1 to 1 mm, and more preferably an overall length of 10 to 30 mm, a width of 3 to 10 mm, and a thickness of 0.1 to 0.6 mm. The same applies to the material and the size of an insulating substrate in embodiments to be described below.

The electrodes and the leads on the insulating substrate can be formed by, for example, forming a conductive layer through sputtering or vapor deposition using a material such as gold, platinum, or palladium, and working the conductive layer into a specific electrode pattern using a laser. As the laser, a YAG laser, a $CO_2$ laser, an excimer laser, or the like can be used, for example. This also applies to the embodiments to be described below.

The second reagent layer 37 is formed in the following manner. For example, an aqueous solution containing 0.1 to 5 U/sensor of an oxidoreductase (e.g., glucose dehydrogenase), 10 to 200 mM of a mediator (e.g., potassium ferricyanide), 1 to 50 mM of an enzyme stabilizer (e.g., maltitol), and 20 to 200 mM of a crystal homogenizing agent (e.g., taurine) is applied dropwise to a circular slit portion and is then dried. The presence of this slit portion can suppress the spread of the aqueous solution applied dropwise, and this allows more accurate positioning of the reagent layer 37. Thus, the reagent layer 37 is formed so as to cover portions of the electrodes 43, 44, and 45. The drying may be, for example, natural drying or forced drying using warm air.

The first reagent layer 36 is formed in the following manner. For example, an aqueous solution containing 10 to 200 mM of a mediator (e.g., potassium ferricyanide) and 20 to 200 mM of a crystal homogenizing agent (e.g., taurine) is applied dropwise to a circular slit portion and is then dried. The presence of this slit portion can suppress the spread of the aqueous solution applied dropwise, and this allows more accurate positioning of the reagent layer 36. Thus, the reagent layer 36 is formed so as to cover portions of the electrodes 42 and 46. The drying may be, for example, natural drying or forced drying using warm air.

In the present invention, the material of the spacer 102 is not particularly limited, and examples thereof include those given above as examples of the material of the insulating substrate. Furthermore, the size of the spacer is not particularly limited, and the spacer has, for example, an overall length of 5 to 100 mm, a width of 2 to 50 mm, and a thickness of 0.01 to 1 mm, preferably an overall length of 7 to 50 mm, a width of 3 to 20 mm, and a thickness of 0.05 to 0.5 mm, and more preferably an overall length of 10 to 30 mm, a width of 3 to 10 mm, and a thickness of 0.05 to 0.25 mm. The spacer of this example has an I-shaped cutout portion that forms the channel for blood introduction. The I-shaped cutout portion has, for example, an overall length of 0.5 to 8 mm and a width of 0.1 to 5 mm, preferably an overall length of 1 to 10 mm and a width of 0.2 to 3 mm, and more preferably an overall length of 1 to 5 mm and a width of 0.5 to 2 mm. This cutout portion may be formed through, for example, cutting with a laser, a drill, or the like, or forming the spacer using a mold with which the cutout portion can be formed. The same applies to the material and the size of a spacer and to a cutout portion in the embodiments to be described below.

In the present invention, the material of the cover 103 is not particularly limited. Examples of the material of the cover 103 include those given above as examples of the material of the insulating substrate. It is more preferable that a portion of the cover that forms the ceiling of the channel for blood introduction is subjected to hydrophilic treatment. The hydrophilic treatment may be performed using a method such as, for example, applying a surfactant or introducing a hydrophilic functional group such as a hydroxyl group, a carbonyl group, or a carboxyl group to the surface of the cover through plasma treatment or the like. Furthermore, a layer composed of a surfactant such as lecithin may be formed on the reagent layers. The size of the cover is not particularly limited. The cover has, for example, an overall length of 5 to 100 mm, a width of 3 to 50 mm, and a thickness of 0.01 to 0.5 mm, preferably an overall length of 10 to 50 mm, a width of 3 to 20 mm, and a thickness of 0.05 to 0.25 mm, and more preferably an overall length of 15 to 30 mm, a width of 5 to 10 mm, and a thickness of 0.05 to 0.1 mm. The cover preferably has the air hole 9 formed therein, and the shape of the air hole 9 is, for example, circular, oval, polygonal, or the like. The air hole 9 has, for example, a maximum diameter of 0.01 to 10 mm, preferably a maximum diameter of 0.05 to 5 mm, and more preferably a maximum diameter of 0.1 to 2 mm. The air hole nay be formed by, for example, perforating the cover using a laser, a drill, or the like, or forming tho cover using a mold with which an air vent portion can be formed. The same applies to the material and the size of a cover and to an air hole in the embodiments to be described below.

Moreover, this second biosensor can be produced by stacking the insulating substrate 111, the spacer 102, and the cover 103 in this order and integrating them. The above-described three members are integrated by attaching them together using an adhesive or through thermal fusion binding or the like. Examples of the adhesive that can be used include epoxy adhesives, acrylic adhesives, polyurethane adhesives, thermosetting adhesives (hot melt adhesives and the like), and UV curable adhesives. This also applies to the embodiments to be described below.

Measurement of the amount of a blood component, e.g., measurement of the blood glucose level using this second biosensor is carried out in the following manner. First, a fingertip or the like is pricked with a dedicated lancet to cause bleeding. Meanwhile, the second biosensor is set in a dedicated measuring device (meter). The blood supply port of the second biosensor set in the measuring device is brought into contact with the blood at the bleeding site, and the blood is introduced into the sensor through capillary action. The analysis using this second biosensor is carried out as per the following steps.

In Embodiment 1C, the electrode 42, the electrode 43, the electrode 44, the electrode 45, and the electrode 46 of the second biosensor are used as an electrode A, an electrode C, an electrode D, an electrode E, and an electrode G, respectively. FIG. 19 shows which of the electrodes is used as the counter electrode and the working electrode of each of a first electrode system, a second electrode system, and a third electrode system. It should be noted that FIG. 18 is a table showing electrodes, the applied voltage, the timing of voltage application, and the application time in the voltage application pattern in Embodiment 1C.

Embodiment 1C is the same as Embodiment 1B, except that the second biosensor is used instead of the first biosensor, and the electrode G and the electrode E are used as the working electrode and the counter electrode in the third electrode system.

In this Embodiment 1C, a hematocrit-dependent current value can be detected using, as the working electrode and the counter electrode in the third electrode system (Hct-3), the electrodes used as the counter electrodes in the first electrode system (Glu-1) and the second electrode system (Glu-2) shown in FIG. 19. Although, in FIG. 19, the electrode G and the electrode E are used as the working electrode and the counter electrode in the third electrode system (Hct-3), respectively, the electrode D, which is one of the counter electrodes in the first electrode system, may also be used as the working electrode or the counter electrode in the third electrode system. Since the electrodes used as the counter electrodes in the first electrode system (Glu-1) and the second electrode system (Glu-2) are used as the working electrode and the counter electrode in the third electrode system (Hct-3), there is little effect of the glucose measurement. Accordingly, the third step of detecting the third hematocrit-dependent current value can be performed while the first step of detecting the first blood component amount-dependent current value and the second step of detecting the second blood component amount-dependent current value are being performed.

Embodiment 2

Embodiment 2 is an example of the blood component amount measurement method 2 of the present invention.

The biosensor used in this method is the same as the first biosensor used in Embodiment 1A. In Embodiment 2, the electrode 12, the electrode 13, the electrode 14, the electrode 15, the electrode 16, and the electrode 17 of the first biosensor are used as an electrode A, an electrode C, an electrode D, electrode E, an electrode G, and an electrode F, respectively. FIG. 22 shows which of the electrodes is used as the counter electrode and the working electrode of each of a first electrode system, a fourth electrode system, and a third electrode system.

Step A: Detection of Sample (Blood)

A voltage is applied between the electrode D and the electrode E, and the introduction of blood is detected based on a change in the current value accompanying the introduction of blood. After the introduction of the blood is detected, subsequent steps are started. The voltage applied in Step A is, for example, 0.05 to 1 V, and preferably 0.7 V. Then, glucose in the blood is allowed to react with glucose oxidoreductase for a certain period of time. It should be noted that Step A is optional.

Step B: Step of Measuring Blood Component Amount-Dependent Current Values

Figure 20:
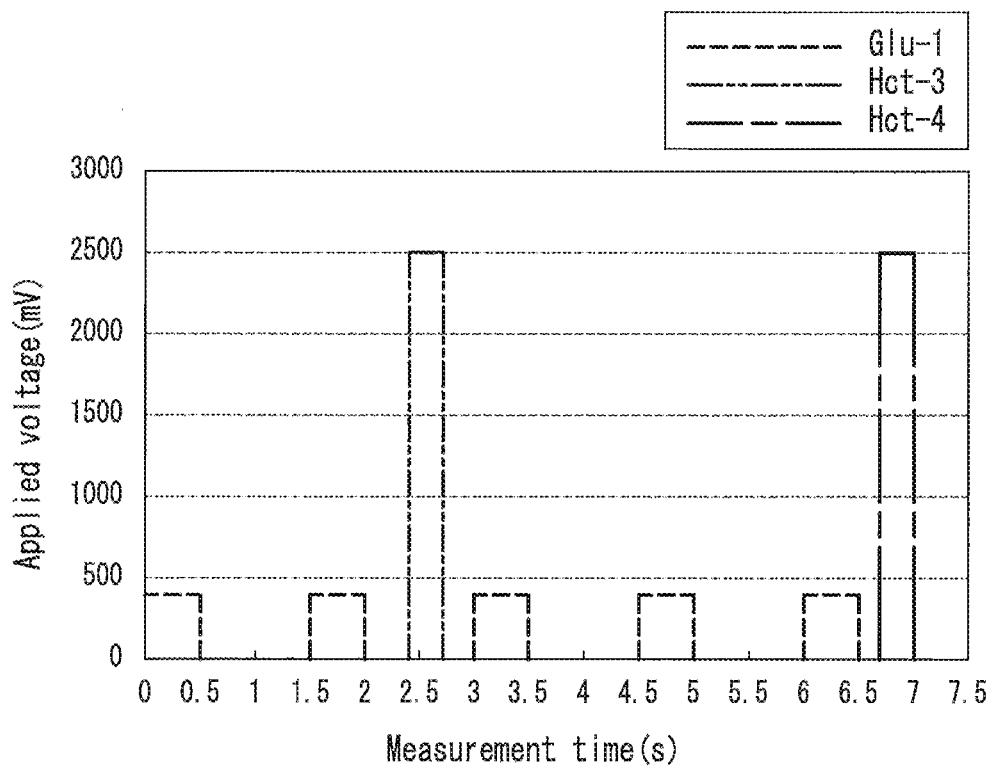
FIG. 20 is a diagram showing a change in voltage value over time in a voltage application pattern in Embodiment 2.

As shown in FIG. 20, after the glucose in the blood has been reacted with the glucose oxidoreductase for a certain period of time, the measuring device 2 applies a voltage to the first electrode system while controlling the voltage value and the application time of a first voltage (first step). The measuring device 2 starts to measure the current when a detection electrode system (the electrode D and the electrode E) detects the blood to be measured after the blood has been introduced into the biosensor 3.

At this time, the measuring device 2 changes the electrodes to be subjected to voltage application, the applied voltage, the application time, and the timing of voltage application as shown in FIG. 21. A first voltage is applied between the electrodes in the first electrode system (including the electrode C serving as the working electrode and the electrodes D and E serving as the counter electrodes). In FIG. 21, voltage application indicated with "Glu-1" corresponds to the voltage application in this first step. The first step of applying the first voltage to the first electrode system and detecting a first blood component amount-dependent current value is performed a plurality of times, e.g., five times.

The blood component amount-dependent current values obtained by applying the first voltage to the first electrode system are used in a step of calculating the amount of the blood component to be described below.

Step C: Step of Measuring Hct

As shown in FIG. 20, after performing the steps of measuring the blood component amount-dependent current value (the first step), the measuring device 2 applies a voltage to the third electrode system (including the electrode A serving as the working electrode and the electrode C serving as the counter electrode) while controlling the voltage value and the application time of a third voltage (third step). Although Step B is performed first and then Step C is performed in this example, Step C may be performed first and then Step B may be performed.

At this time, the measuring device 2 changes the electrodes to be subjected to voltage application, the applied voltage, the application time, and the timing of voltage application as shown in FIG. 21. The third voltage is applied between the electrodes in the third electrode system. In FIG. 21, voltage application indicated with "Hct-3" corresponds to the voltage application in this step. The third voltage is 2500 mV. A third hematocrit-dependent current value obtained by applying the third voltage to the third electrode system is used in the step of calculating the amount of the blood component to be described below.

In this Step C, in addition to performing the third step, a voltage is applied to the fourth electrode system (including the electrode D serving as the working electrode and the electrode G serving as the counter electrode) while controlling the voltage value and the application time of a fourth voltage (fourth step). In FIG. 21, voltage application indicated with "Hct-4" corresponds to the voltage application in this fourth step. The fourth voltage is 2500 mV. A fourth hematocrit-dependent current value obtained by applying the fourth voltage to the fourth electrode system is used in the step of calculating the amount of the blood component to be described below.

It should be noted that, in this embodiment, the electrode F that is coated with a polymer such as CMC only and on which the second reagent layer and the third reagent layer are not disposed, that is, a bare electrode, is not used.

Step D: Step of Calculating Amount of Blood Component

The plurality of, e.g., the plurality of blood component amount-dependent current values obtained are processed as follows before they are used as the blood component amount-dependent current values.

A plurality of parameters (x1, x2, x3, . . . x10) are calculated based on, for example, the extracted current values measured at the plurality of predetermined time points and the extracted temperature information of the biological information measuring device ("calculate predetermined parameters"), a correction amount is calculated using a multiple regression equation (e.g., Formula 1 below), and then a blood component amount-dependent current value is calculated.

$$y = ax1 + bx2 + cx3 \ldots + kx10 + l \quad \text{(Formula 1)}$$

(y denotes the correction amount, x1, x2, x3 . . . , and x10 denote parameters, and a, b, c, . . . and l denote coefficients.)

The amount of the blood component is obtained using the third Hct-dependent current value and the fourth Hct-dependent current value obtained in Step C, and the first blood component-dependent current values obtained in Step B. Preferably, this is performed based on a calibration curve (including a calibration table) prepared beforehand. The thus-obtained amount of the blood component is displayed or stored in the measuring device.

After the amount of the blood component has been calculated, the biosensor is discarded and the display unit and the like are turned off. Thereafter, the measuring device is also turned off to complete the measurement of the component of the biological sample.

Embodiment 3A

Embodiment 3A is an example of the blood component amount measurement method 3 of the present invention.

The biosensor used in this method is the same as the first biosensor used in Embodiment 1A. In Embodiment 3A, the electrode 12, the electrode 13, the electrode 14, the electrode 15, the electrode 16, and the electrode 17 of the first biosensor are used as an electrode A, an electrode C, an electrode D, an electrode E, an electrode G, and an electrode F, respectively. FIG. 25 shows which of the electrodes is used as the counter electrode and the working electrode of each of a first electrode system, a second electrode system, a fourth electrode system, and a third electrode system.

Step A: Detection of Sample (Blood)

A voltage is applied between the electrode D and the electrode E, and the introduction of blood is detected based on a change in the current value accompanying the introduction of blood. After the introduction of the blood is detected, subsequent steps are started. The voltage applied in Step A is, for example, 0.05 to 1 V, and preferably 0.7 V. Then, glucose in the blood is allowed to react with glucose oxidoreductase for a certain period of time. It should be noted that Step A is optional.

Step B: Step of Measuring Blood Component Amount-Dependent Current Values

Figure 23:
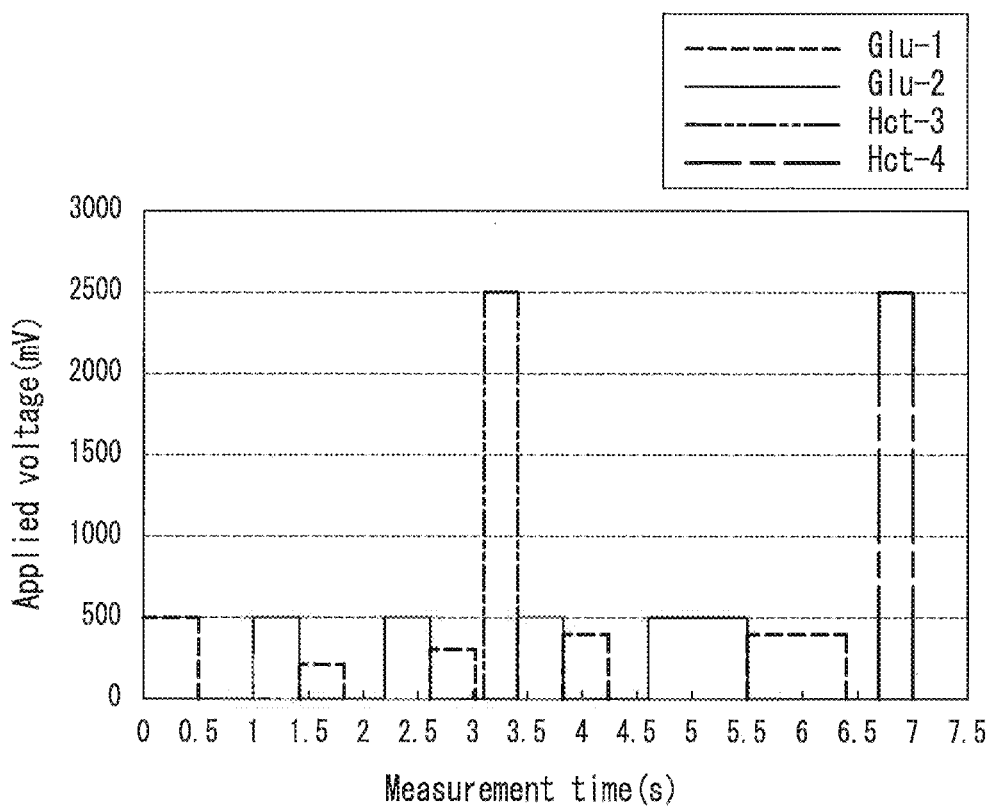
FIG. 23 is a diagram showing a change in voltage value over time in a voltage application pattern in Embodiment 3A.

As shown in FIG. 23, after the glucose in the blood has been reacted with the glucose oxidoreductase for a certain period of time, the measuring device 2 applies a voltage to the first electrode system while controlling the voltage value and the application time of a first voltage (first step). The measuring device 2 starts to measure the current when a detection electrode system (the electrode D and the electrode E) detects the blood to be measured after the blood has been introduced into the biosensor 3.

At this time, the measuring device 2 changes the electrodes to be subjected to voltage application, the applied voltage, the application time, and the timing of voltage application as shown in FIG. 24. The first voltage is applied between the electrodes in the first electrode system (including the electrode C serving as the working electrode and the electrodes D and E serving as the counter electrodes). In FIG. 24, voltage application indicated with "Glu-1" corresponds to the voltage application in this first step. The first voltage is 200 mV to 500 mV. The first step of applying the first voltage to the first electrode system and detecting a first blood component amount-dependent current value is performed a plurality of times, e.g., five times.

In the case where the first step is performed at least twice, the first voltages may be different from each other. This is because the effects of interfering substances that react at different voltages can be observed.

In this Step B, in addition to performing the first step, a voltage is applied to the second electrode system while controlling the voltage value and the application time of a second voltage (second step). In FIG. 24, voltage application indicated with "Glu-2" corresponds to the voltage application in this second step. The second voltage is 500 mV. The second step of applying the second voltage to the second electrode system and detecting a blood component amount-dependent current value is performed a plurality of times, e.g., four times. The first steps and the second steps are performed in turn as follows, for example: the first step, the second step, the first step, the second step, and so on. In the case where the second step is performed at least twice, the second voltages may be equal to each other. This is because, for example, transition of the response value (current value) on the time axis can be observed.

In this Step B, the first step may be performed at least twice, the second step may be performed at least twice, and the second steps and the first steps may be performed alternately.

In this Step B, the order of performing the first step and the second step may be changed. That is, although the first step is performed first in the example illustrated in FIG. 24, the second step may be performed first.

The first blood component amount-dependent current values obtained by applying the first voltage to the first electrode system and the second blood component amount-dependent current values obtained by applying the second voltage to the second electrode system are used in a step of calculating the amount of the blood component to be described below.

Step C: Step of Measuring Hct

As shown in FIG. 23, after performing the step of measuring the first blood component amount-dependent current value (the first step) and the step of measuring the second blood component amount-dependent current value (the second step), the measuring device 2 applies a voltage to the third electrode system while controlling the voltage value and the application time of a third voltage (third step). Although Step B is performed first and then Step C is performed in this example, Step C may be performed first and then Step B may be performed.

At this time, the measuring device 2 changes the electrodes to be subjected to voltage application, the applied voltage, the application time, and the timing of voltage application as shown in FIG. 24. The third voltage is applied between the electrodes in the third electrode system (including the electrode A serving as the working electrode and the electrode C serving as the counter electrode). In FIG. 24, voltage application indicated with "Hct-3" corresponds to the voltage application in this step. The third voltage is 2500 mV. A third hematocrit-dependent current value obtained by applying the third voltage to the third electrode system is used in the step of calculating the amount of the blood component to be described below.

In this Step C, in addition to performing the third step, a voltage is applied to the fourth electrode system while controlling the voltage value and the application time of a fourth voltage (fourth step). In FIG. 24, voltage application indicated with "Hct-2" corresponds to the voltage application in this fourth step. The fourth voltage is 2500 mV. A fourth hematocrit-dependent current value obtained by applying the fourth voltage to the fourth electrode system is used in the step of calculating the amount of the blood component to be described below.

It should be noted that, in this embodiment, the electrode F that is coated with a polymer such as CMC only and on which the second reagent layer and the third reagent layer are not disposed, that is, a bare electrode, is not used.

Step D: Step of Calculating Amount of Blood Component

The plurality of, e.g., the plurality of blood component amount-dependent current values obtained are processed as follows before they are used as the blood component amount-dependent current values.

A plurality of parameters (x1, x2, x3, . . . x10) are calculated based on, for example, the extracted current values measured at the plurality of predetermined time points and the extracted temperature information of the biological information measuring device ("calculate predetermined parameters"), a correction amount is calculated vising a multiple regression equation (e.g., Formula 1 below), and then a blood component amount-dependent current value is calculated.

$$y=ax1+bx2+cx3\ldots+kx10+l \quad \text{(Formula 1)}$$

(y denotes the correction amount, x1, x2, x3 . . . , and x10 denote parameters, and a, b, c, . . . and l denote coefficients.)

The amount of the blood component is obtained using the third Hct-dependent current value and the fourth Hct-dependent current value obtained in Step C, and the first blood component-dependent current values and the second blood component-dependent current values obtained in Step B. Preferably, this is performed based on a calibration curve (including a calibration table) prepared beforehand. The thus-obtained amount of the blood component is displayed or stored in the measuring device.

After the amount of the blood component has been calculated, the biosensor is discarded and the display unit and the like are turned off. Thereafter, the measuring device is also turned off to complete the measurement of the component of the biological sample.

Embodiment 3B

Embodiment 3B is an example of the blood component amount measurement method 3 of the present invention.

Figure 29:
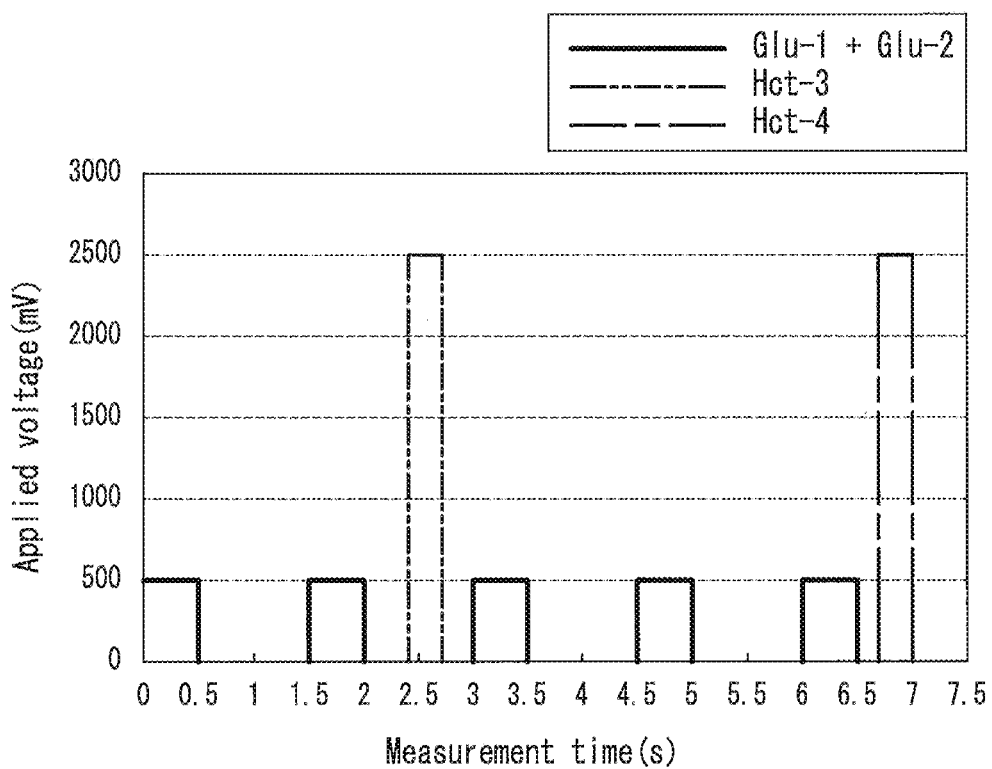
FIG. 29 is a diagram showing a change in voltage value over time in a voltage application pattern in Embodiment 3C.

The biosensor used in this method is the same as the first biosensor used in Embodiment 1A. In Embodiment 3B, the electrode 12, the electrode 13, the electrode 14, the electrode 15, the electrode 16, and the electrode 17 of the first biosensor are used as an electrode A, an electrode C, an electrode D, an electrode E, an electrode G, and an electrode F, respectively. FIG. 29 shows which of the electrodes is used as the counter electrode and the working electrode of each of a first electrode system, a second electrode system, a third electrode system, and a fourth electrode system.

Figure 26:
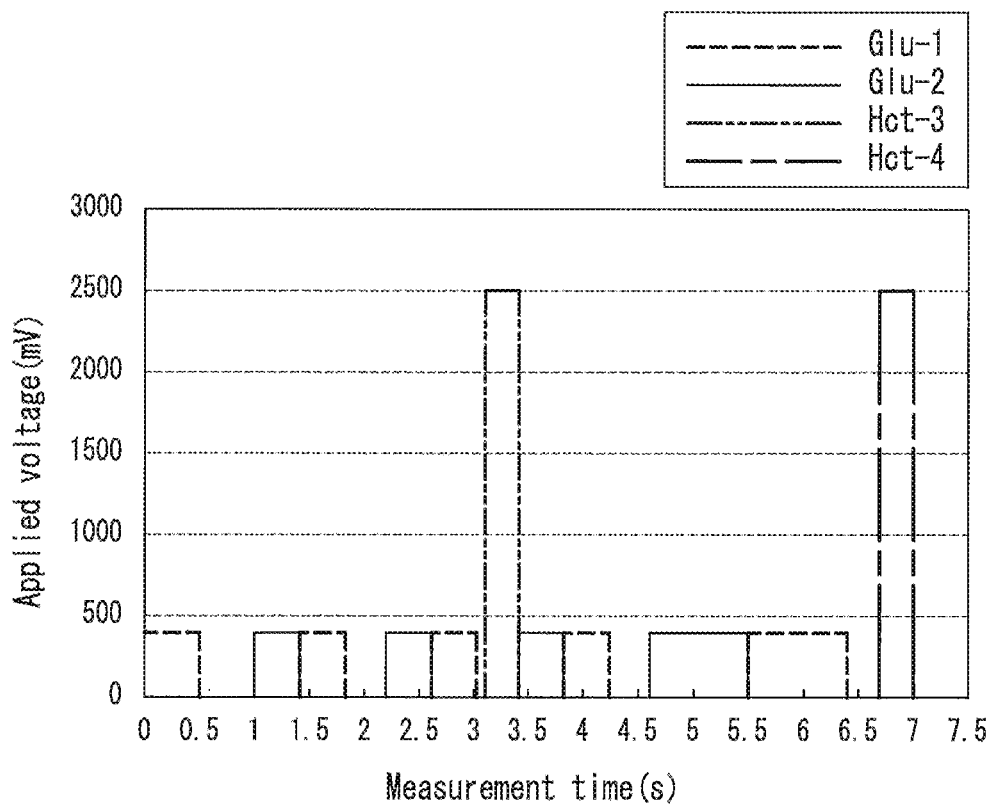
FIG. 26 is a diagram showing a change in voltage value over time in a voltage application pattern in Embodiment 3B.

In Embodiment 3B, the measuring device 2 changes the electrodes to be subjected to voltage application, the applied voltage, the application time, and the timing of voltage application as shown in FIG. 26. In FIG. 27, voltage application indicated with "Glu-1" corresponds to the voltage application in this first step. A first voltage is 400 mV. The first step of applying the first voltage to the first electrode system and detecting a first blood component amount-dependent current value is performed a plurality of times, e.g., five times. In this Step B, at the time different from the first step, a voltage is applied to the second electrode system while controlling the voltage value and the application time of a second voltage (second step). In FIG. 27, voltage application indicated with "Glu-2" corresponds to the voltage application in this second step. The second voltage is 400 mV. The second step of applying the second voltage to the second electrode system and detecting a blood component amount-dependent current value is performed a plurality of times, e.g., four times.

Embodiment 3B is the same as Embodiment 3A, except that the first voltage and the second voltage are constant.

Embodiment 3C

Embodiment 3C is an example of the blood component amount measurement method 3 of the present invention.

The biosensor used in this method is the same as the first biosensor used in Embodiment 1A. In Embodiment 3C, the electrode 12, the electrode 13, the electrode 14, the electrode 15, the electrode 16, and the electrode 17 of the first biosensor are used as an electrode A, an electrode C, an electrode D, an electrode E, an electrode G, and an electrode F, respectively. FIG. 31 shows which of the electrodes is used as the counter electrode and the working electrode of each of a first electrode system, a second electrode system, a third electrode system, and a fourth electrode system.

In Embodiment 3C, the measuring device 2 changes the electrodes to be subjected to voltage application, the applied voltage, the application time, and the timing of voltage application as shown in FIG. 29. In FIG. 30, voltage application indicated with "Glu-1" corresponds to the voltage application in this first step. A first voltage is 500 mV. The first step of applying tho first voltage to the first electrode system and detecting a first blood component amount-dependent current value is performed a plurality of times, e.g., five times. In this Step B, at the same time as the first step, a voltage is applied to the second electrode system while controlling the voltage value and the application time of a second voltage (second step). In FIG. 30, voltage application indicated with "Glu-2" corresponds to the voltage application in this second step. The second voltage is 500 mV. The second step of applying the second voltage to the second electrode system and detecting a blood component amount-dependent current value is performed a plurality of times, e.g., five times.

Embodiment 3C is the same as Embodiment 3B, except that the first step and the second step are performed simultaneously.

Embodiment 3D

Embodiment 3D is an example of the blood component amount measurement method 3 of the present invention.

The biosensor used in this method is the same as the first biosensor used in Embodiment 1A. In Embodiment 3D, the electrode 12, the electrode 13, the electrode 14, the electrode 15, the electrode 16, and the electrode 17 of the first biosensor are used as an electrode A, an electrode C, an electrode D, an electrode E, an electrode G, and an electrode F, respectively. FIG. 34 shows which of the electrodes is used as the counter electrode and the working electrode of each of a first electrode system, a second electrode system, a third electrode system, and a fourth electrode system.

Figure 32:
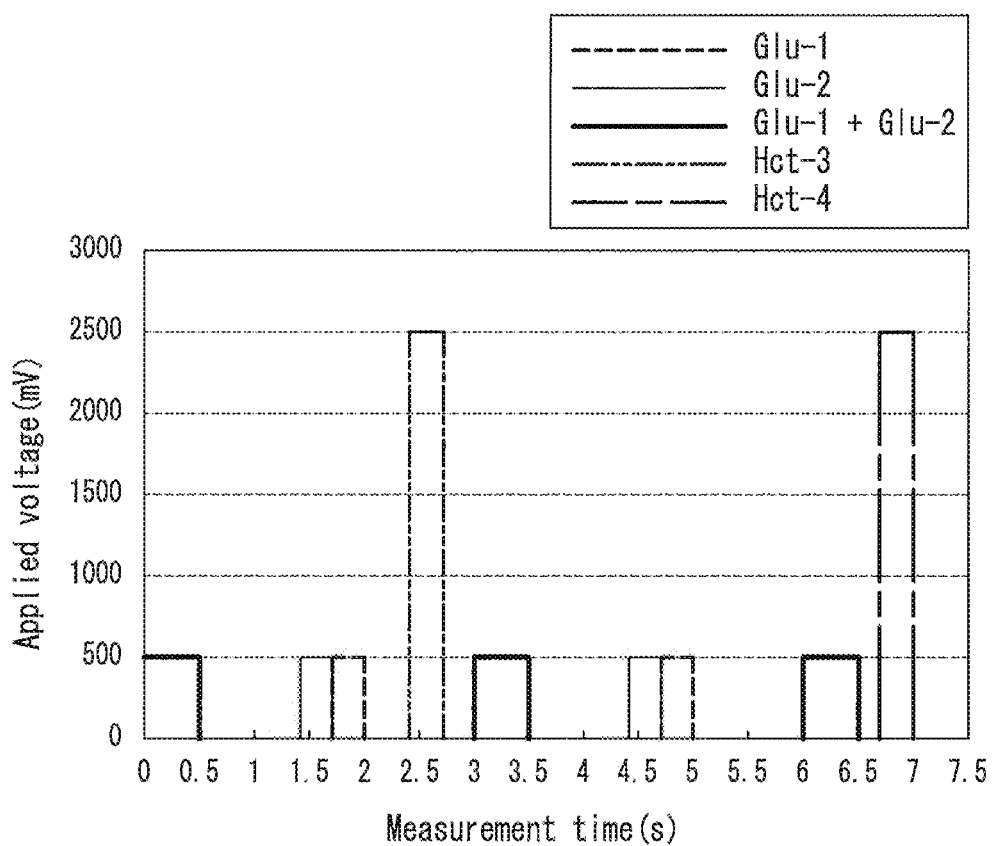
FIG. 32 is a diagram showing a change in voltage value over time in a voltage application pattern in Embodiment 3D.

In Embodiment 3D, the measuring device 2 changes the electrodes to be subjected to voltage application, the applied voltage, the application time, and the timing of voltage application as shown in FIG. 32. In FIG. 33, voltage application indicated with "Glu-1" corresponds to the voltage application in this first step. A first voltage is 500 mV. The first step of applying the first voltage to the first electrode system and detecting a first blood component amount-dependent current value is performed a plurality of times, e.g., five times. In this Step B, at the same time as the first step or at the time different from the first step, a voltage is applied to the second electrode system while controlling the voltage value and the application time of a second voltage (second step). In FIG. 33, voltage application indicated with "Glu-2" corresponds to the voltage application in this second step. The second voltage is 500 mV. The second step of applying the second voltage to the second electrode system and detecting a blood component amount-dependent current value is performed a plurality of times, e.g., five times.

Embodiment 3D is the same as Embodiment 3B, except that portions of the first steps and the second steps are performed simultaneously.

Embodiment 4

Embodiment 4 is an example of the blood component amount measurement method 4 of the present invention.

Figure 9:
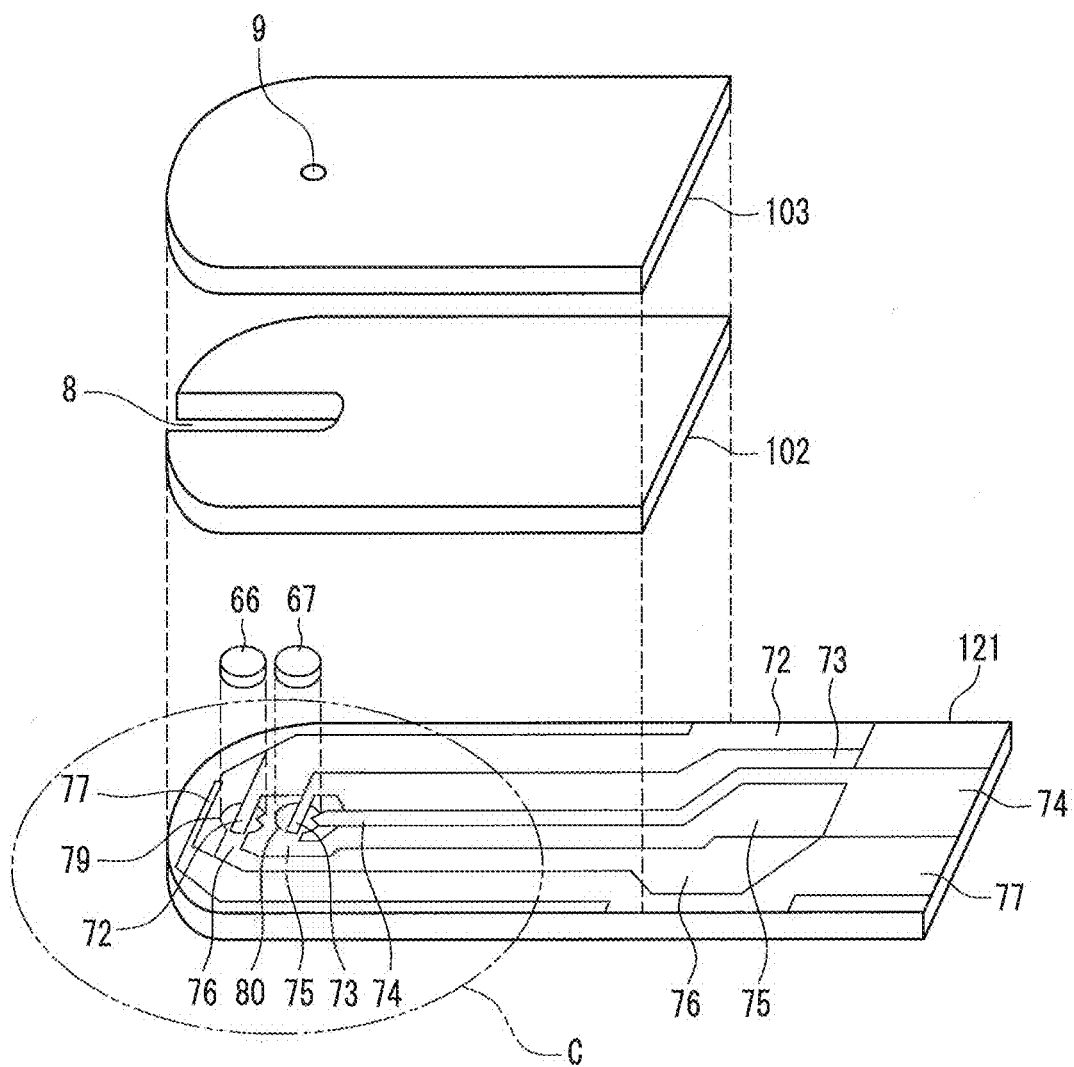
FIG. 9 is an exploded perspective view showing another example of the biosensor used in the measurement method of the present invention.
Figure 10:
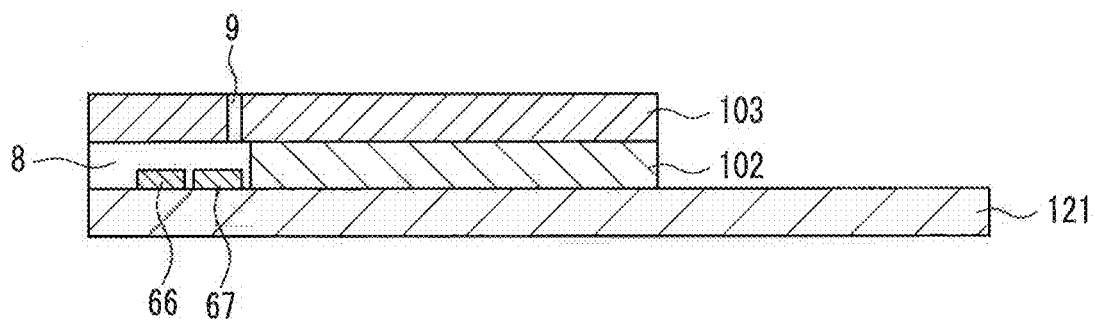
FIG. 10 is a cross-sectional view of the biosensor shown in FIG. 9.
Figure 11A:
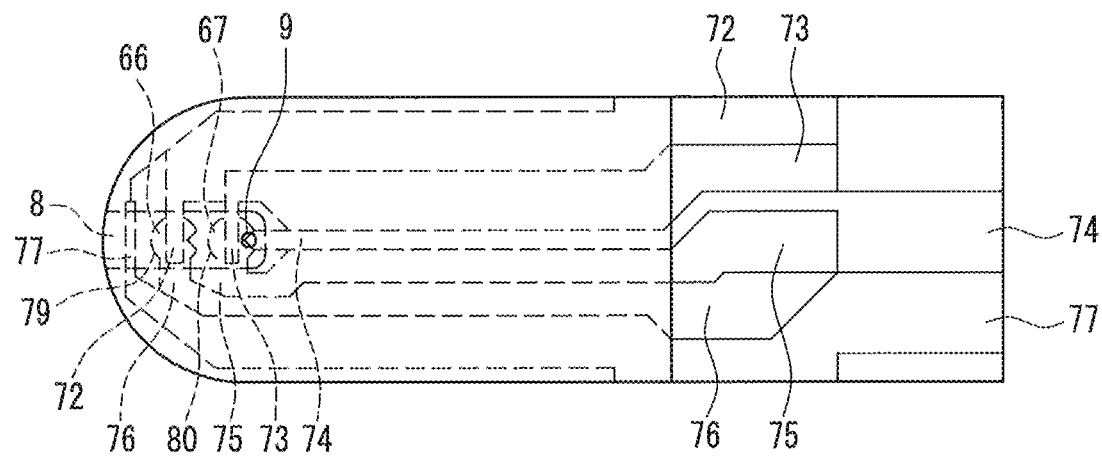
FIG. 11A is a plan view of the biosensor shown in FIG. 9.
Figure 11B:
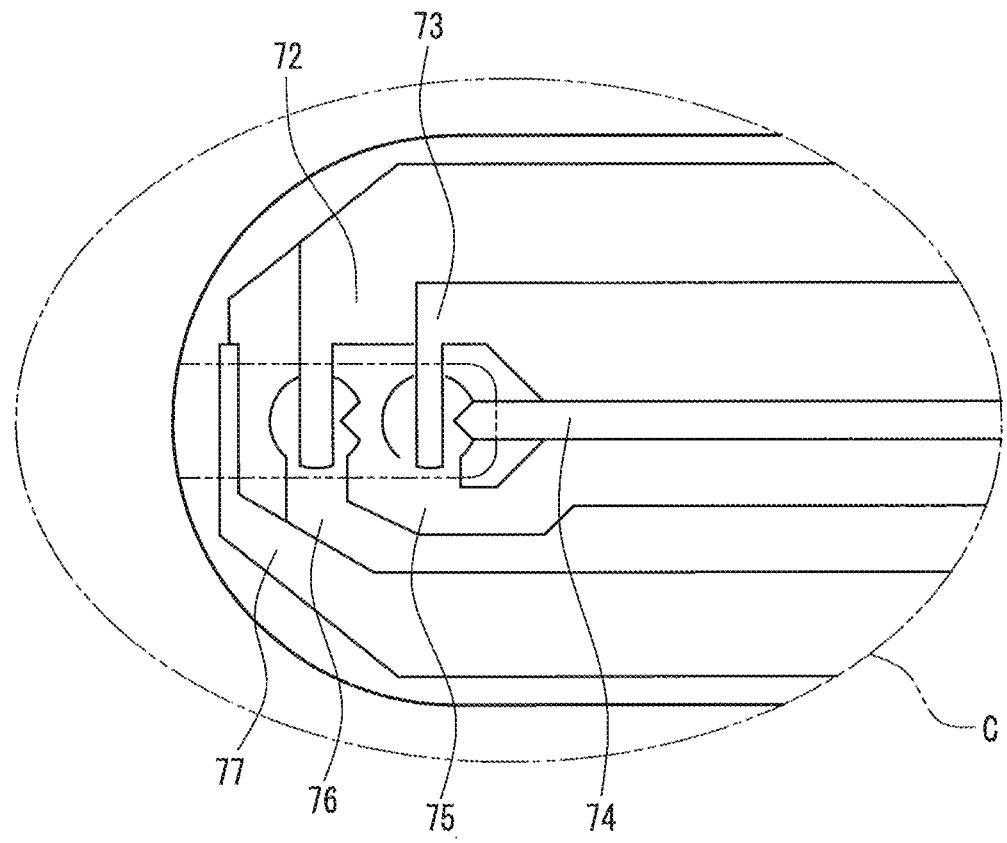
FIG. 11B is an enlarged view of a portion C shown in FIG. 9.

FIGS. 9, 10, 11A, and 11B show another example of the biosensor (also referred to as "third biosensor" hereinafter) used in the measurement method of the present invention. FIG. 9 is an exploded perspective view of the third biosensor, FIG. 10 is a cross-sectional view of the biosensor shown in FIG. 9, FIG. 11A is a plan view of the biosensor shown in FIG. 9, and FIG. 11B is an enlarged view of a portion C shown in FIG. 9. In the above-described four drawings, the same components and portions are given the same reference numerals. As an illustrative example, this biosensor is a sensor for measuring glucose as a blood component.

As shown in the drawings, in this sensor, six electrodes 72, 73, 74, 75, 76, and 77 are formed on an insulating substrate 121. These electrodes are each switchable between a working electrode and a counter electrode. The surfaces of the electrodes 72, 73, 74, 75, 76, and 77 are coated with a polymer material such as CMC. A first reagent layer 66 is disposed so as to cover portions of the electrodes 72 and 76 at the location of the first reagent 79, and a second reagent layer 67 is disposed so as to cover portions of the electrodes 73, 74, and 75 at the location of the second reagent 80. Neither the first reagent layer 66 nor the second reagent layer 67 are disposed on the electrode 77. The first reagent layer 66 and the second reagent layer 67 are disposed spaced apart from each other. The second reagent layer contains a reagent for measuring the amount of a blood component in blood, preferably an oxidoreductase (e.g., glucose dehydrogenase), and more preferably an oxidoreductase and a mediator (e.g., potassium ferricyanide), and optionally contains an enzyme stabilizer, a crystal homogenizing agent, and/or the like. The third reagent layer contains a reagent for measuring the amount of a blood component in blood, preferably an oxidoreductase (e.g., glucose dehydrogenase), and more preferably an oxidoreductase and a mediator (e.g., potassium ferricyanide), and optionally contains an enzyme stabilizer, a crystal homogenizing agent, and/or the like.

A cover 103 is disposed on the insulating substrate 121 via a spacer 102 with one end of the insulating substrate 121 (the right end in the drawings) being left uncovered. In this third biosensor, in order to introduce blood to the respective electrodes (72, 73, 74, 75, 76, and 77), a channel 8 is formed by the insulating substrate 121, the spacer 102, and the cover 103. The leading end of this channel 8 extends to the other end of the third biosensor (the left end in the drawings) and is open to the outside to serve as a blood supply port 10. The six electrodes (72, 73, 74, 75, 76, and 77) are connected to leads, respectively, and these leads extend toward the above-described one end (the right end in the drawings), and leading ends of the leads are exposed without being covered by the cover. The cover 103 has an air hole 9 formed in a portion (on the second reagent layer 67 or on the electrode 74) corresponding to the right end of the channel 8. Furthermore, the first reagent layer 66 and the second reagent layer 67 are disposed spaced apart from each other in the channel 8 at the location of the first reagent 79 and the location of the second reagent 80, respectively.

In the present invention, the material of the insulating substrate is not particularly limited. Examples of the material that can be used include polyethylene terephthalate (PET), polycarbonate (PC), polyimide (PI), polyethylene (PE), polypropylene (PP), polystyrene (PS), polyvinyl chloride (PVC), polyoxymethylene (POM), monomer-cast nylon (MC), polybutylene terephthalate (PBT), methacrylic resins (PMMA), ABS resin (ABS), and glass. Of these, polyethylene terephthalate (PET), polycarbonate (PC), and polyimide (PI) are preferable, and polyethylene terephthalate (PET) is more preferable. The size of the insulating substrate is not particularly limited, and the insulating substrate has, for example, an overall length of 5 to 100 mm, a width of 2 to 50 mm, and a thickness of 0.05 to 2 mm, preferably an overall length of 7 to 50 mm, a width of 3 to 20 mm, and a thickness of 0.1 to 1 mm, and more preferably an overall length of 10 to 30 mm, a width of 3 to 10 mm, and a thickness of 0.1 to 0.6 mm. The same applies to the material and the size of an insulating substrate in embodiments to be described below.

The electrodes and the leads on the insulating substrate can be formed by, for example, forming a conductive layer through sputtering or vapor deposition using a material such as gold, platinum, or palladium, and working the conductive layer into a specific electrode pattern using a laser. As the laser, a YAG laser, a $CO_2$ laser, an excimer laser, or the like can be used, for example. This also applies to the embodiments to be described below.

The second reagent layer 67 is formed in the following manner. For example, an aqueous solution containing 0.1 to 5 U/sensor of an oxidoreductase (e.g., glucose dehydrogenase), 10 to 200 mM of a mediator (e.g., potassium ferricyanide), 1 to 50 mM of an enzyme stabilizer (e.g., maltitol), and 20 to 200 mM of a crystal homogenizing agent (e.g., taurine) is applied dropwise to a circular slit portion and is then dried. The presence of this slit portion can suppress the spread of the aqueous solution applied dropwise, and this allows more accurate positioning of the reagent layer 67. Thus, the reagent layer 7 is formed so as to cover portions of the electrodes 73, 74, and 75. The drying may be, for example, natural drying or forced drying using warm air.

The first reagent layer 66 is formed in the following manner. For example, an aqueous solution containing 10 to 200 mM of a mediator (e.g., potassium ferricyanide) and 20 to 200 mM of a crystal homogenizing agent (e.g., taurine) is applied dropwise to a circular slit portion and is then dried. The presence of this slit portion can suppress the spread of the aqueous solution applied dropwise, and this allows more accurate positioning of the reagent layer 66. Thus, the reagent layer 6 is formed so as to cover portions of the electrodes 72 and 76. The drying may be, for example, natural drying or forced drying using warm air.

In the present invention, the material of the spacer 102 is not particularly limited, and examples thereof include those given above as examples of the material of the insulating substrate. Furthermore the size of the spacer is not particularly limited, and the spacer has, for example, an overall length of 5 to 100 mm, a width of 2 to 50 mm, and a thickness of 0.01 to 1 mm, preferably an overall length of 7 to 50 mm, a width of 3 to 20 mm, and a thickness of 0.05 to 0.5 mm, and more preferably an overall length of 10 to 30 mm, a width of 3 to 10 mm, and a thickness of 0.05 to 0.25 mm. The spacer of this example has an I-shaped cutout portion that forms the channel for blood introduction. The I-shaped cutout portion has, for example, an overall length of 0.5 to 8 mm and a width of 0.1 to 5 mm, preferably an overall length of 1 to 10 mm and a width of 0.2 to 3 mm, and more preferably an overall length of 1 to 5 mm and a width of 0.5 to 2 mm. This cutout portion may be formed through, for example, cutting with a laser, a drill, or the like, or forming the spacer using a mold with which the cutout portion can be formed. The same applies to the material and the size of a spacer and to a cutout portion in the embodiments to be described below.

In the present invention, the material of the cover 103 is not particularly limited. Examples of the material of the cover 103 include those given above as examples of the material of the insulating substrate. It is more preferable that a portion of the cover that forms the ceiling of the channel for blood introduction is subjected to hydrophilic treatment. The hydrophilic treatment may be performed using a method such as, for example, applying a surfactant or introducing a hydrophilic functional group such as a hydroxyl group, a carbonyl group, or a carboxyl group to the surface of the cover through plasma treatment or the like. Furthermore, a layer composed of a surfactant such as lecithin may be formed on the reagent layers. The size of the cover is not particularly limited. The cover has, for example, an overall length of 5 to 100 mm, a width of 3 to 50 mm, and a thickness of 0.01 to 0.5 mm, preferably an overall length of 10 to 50 mm, a width of 3 to 20 mm, and a thickness of 0.05 to 0.25 mm, and more preferably an overall length of 15 to 30 mm, a width of 5 to 10 mm, and a thickness of 0.05 to 0.1 mm. The cover preferably has the air hole 9 formed therein, and the shape of the air hole 9 is, for example, circular, oval, polygonal or the like. The air hole 9 has, for example, a maximum diameter of 0.01 to 10 mm, preferably a maximum diameter of 0.05 to 5 mm, and more preferably a maximum diameter of 0.1 to 2 mm. The air hole may be formed by, for example, perforating the cover using a laser, a drill or the like, or forming the cover using a mold with which an air vent portion can be formed. The same applies to the material and the size of a cover and to an air hole in the embodiments to be described below.

Moreover, this third biosensor can be produced by stacking the insulating substrate 121, the spacer 102, and the cover 103 in this order and integrating them. The above-described three members are integrated by attaching them together using an adhesive or through thermal fusion landing or the like. Examples of the adhesive that can be used include epoxy adhesives, acrylic adhesives, polyurethane adhesives, thermosetting adhesives (hot melt adhesives and the like), and UV curable adhesives. This also applies to the embodiments to be described below.

Measurement of the amount of a blood component, e.g., measurement of the blood glucose level using this third biosensor is carried out in the following manner. First, a fingertip or the like is pricked with a dedicated lancet to cause bleeding. Meanwhile, the sensor is set in a dedicated measuring device (meter). The blood supply port of the sensor set in the measuring device is brought into contact with the blood at the bleeding site, and the blood is introduced into the sensor through capillary action. The analysis using this sensor is carried out as per the following steps.

In Embodiment 4, the electrode 72, the electrode 73, the electrode 74, the electrode 75, the electrode 76, and the electrode 77 of the third biosensor are used as an electrode A, an electrode C, an electrode D, an electrode E, an electrode F, and an electrode G, respectively. FIG. 37 shows which of the electrodes is used as the counter electrode and the working electrode of each of a first electrode system, a third electrode system, a fifth electrode system, and a sixth electrode system.

Step A: Detection of Sample (Blood)

A voltage is applied between the electrode D and the electrode E, and the introduction of blood is detected based on a change in the current value accompanying the introduction of blood. After the introduction of the blood is detected, subsequent steps are started. The voltage applied in Step A is, for example, 0.05 to 1 V, and preferably 0.7 V.

Then, glucose in the blood is allowed to react with glucose oxidoreductase for a certain period of time. It should be noted that Step A is optional.

Step B: Step of Measuring Blood Component Amount-Dependent Current Values

Figure 35:
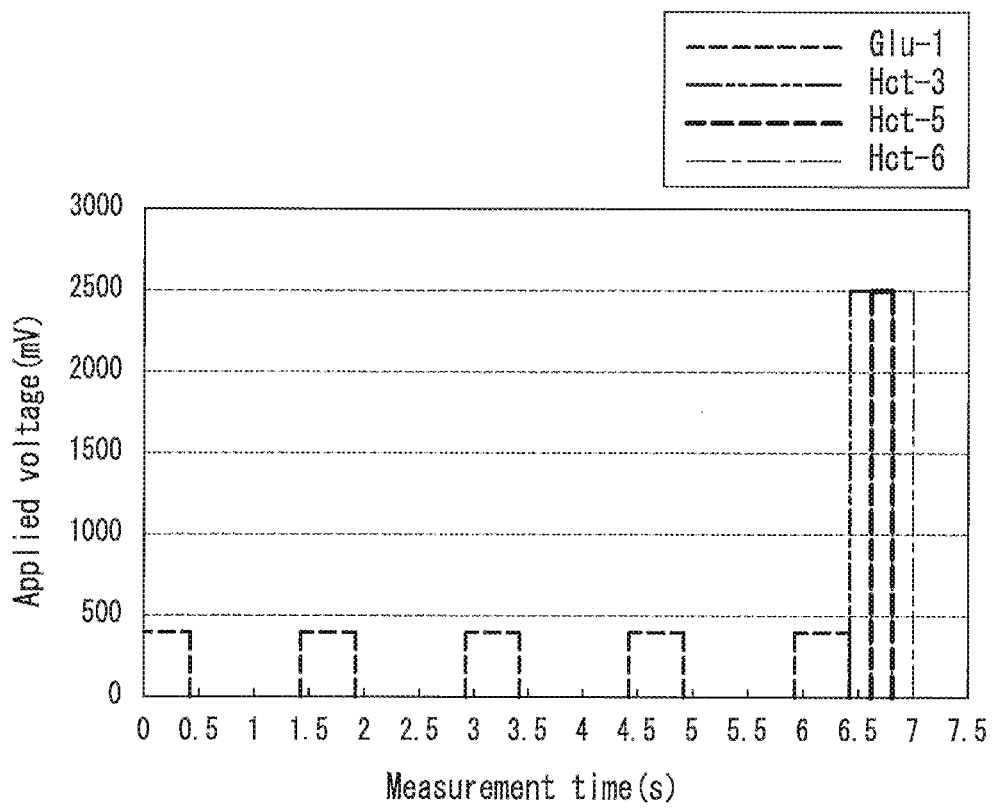
FIG. 35 is a diagram showing a change in voltage value over time in a voltage application pattern in Embodiment 4.

As shown in FIG. 35, after the glucose in the blood has been reacted with the glucose oxidoreductase for a certain period of time, the measuring device 2 applies a voltage to the first electrode system while controlling the voltage value and the application time of a first voltage (first step). The measuring device 2 starts to measure the current when a detection electrode system (the electrode D and the electrode E) detects the blood to be measured after the blood has been introduced into the biosensor 3.

At this time, the measuring device 2 changes the electrodes to be subjected to voltage application, the applied voltage, the application time, and the timing of voltage application as shown in FIG. 36. The first voltage is applied between the electrodes in the first electrode system (including the electrode C serving as the working electrode and the electrodes D and E serving as the counter electrodes). In FIG. 36, voltage application indicated with "Glu-1" corresponds to the voltage application in this first step. The first step of applying the first voltage to the first electrode system and detecting a first blood component amount-dependent current value is performed a plurality of times, e.g., five times.

The blood component amount-dependent current values obtained by applying the first voltage to the first electrode system are used in a step of calculating the amount of the blood component to be described below.

Step C: Step of Measuring Hct

As shown in FIG. 35, after performing the step of measuring the blood component amount-dependent current value (the first step), the measuring device 2 applies a voltage to the third electrode system while controlling the voltage value and the application time of a third voltage (third step). Although Step B is performed first and then Step C is performed in this example, Step C may be performed first and then Step B may be performed.

At this time, the measuring device 2 changes the electrodes to be subjected to voltage application, the applied voltage, the application time, and the timing of voltage application as shown in FIG. 36. The third voltage is applied between the electrodes in the third electrode system (including the electrode A serving as the working electrode and the electrode C serving as the counter electrode). In FIG. 36, voltage application indicated with "Hct-3" corresponds to the voltage application in this step. The third voltage is 2500 mV. A third hematocrit-dependent current value obtained by applying the third voltage to the third electrode system is used in the step of calculating the amount of the blood component to be described below.

In this Step C, in addition to performing the third step, a voltage is applied to the fifth electrode system (including the electrode F serving as the working electrode and the electrodes A and G serving as the counter electrodes) while controlling the voltage value and the application time of a fifth voltage (fifth step). In FIG. 36, voltage application indicated with "Hct-5" corresponds to the voltage application in this fifth step. The fifth voltage is 2500 mV. A fifth hematocrit-dependent current value obtained by applying the fifth voltage to the fifth electrode system is used in the step of calculating the amount of the blood component to be described below.

In this Step C, in addition to performing the third step and the fifth step, a voltage is applied to the sixth electrode system (including the electrode F serving as the working electrode and the electrodes C, E and D serving as the counter electrodes) while controlling the voltage value and the application time of a sixth voltage (sixth step). In FIG. 36, voltage application indicated with "Hct-6" corresponds to the voltage application in this sixth step. The sixth voltage is 2500 mV. A sixth hematocrit-dependent current value obtained by applying the sixth voltage to the sixth electrode system is used in the step of calculating the amount of the blood component to be described below.

It should be noted that, in this embodiment, the electrode F that is coated with a polymer such as CMC only and on which the second reagent layer and the third reagent layer are not disposed, that is, a bare electrode, is used.

Step D: Step of Calculating Amount of Blood Component

The plurality of, e.g., the plurality of blood component amount-dependent current values obtained are processed as follows before they are used as the blood component amount-dependent current values.

A plurality of parameters (x1, x2, x3, . . . , x10) are calculated based on, for example, the extracted current values measured at the plurality of predetermined time points and the extracted temperature information of the biological information measuring device ("calculate predetermined parameters"), a correction amount is calculated using a multiple regression equation (e.g., Formula 1 below), and then a blood component amount-dependent current value is calculated.

$$y=ax1+bx2+cx3 \ldots +kx10+l \quad \text{(Formula 1)}$$

(y denotes the correction amount, x1, x2, x3 . . . , and x10 denote parameters, and a, b, c, . . . and l denote coefficients.)

The amount of the blood component is obtained using the third Hct-dependent current value, the fifth Hct-dependent current value, and the sixth Hct-dependent current value obtained in Step C, and the first blood component-dependent current values obtained in Step B. Preferably, this is performed based on a calibration curve (including a calibration table) prepared beforehand. The thus-obtained amount of the blood component is displayed or stored in the measuring device.

After the amount of the blood component has been calculated, the biosensor is discarded and the display unit and the like are turned off. Thereafter, the measuring device is also turned off to complete the measurement of the component of the biological sample.

Embodiment 5

Embodiment 5 is an example of the blood component amount measurement method 5 of the present invention.

The biosensor used in this method is the same as the third biosensor used in Embodiment 4. In Embodiment 5, the electrode 72, the electrode 73, the electrode 74, the electrode 75, the electrode 76, and the electrode 77 of the third biosensor are used as an electrode A, an electrode C, an electrode D, an electrode E, an electrode F, and an electrode G, respectively. FIG. 40 shows which of the electrodes is used as the counter electrode and the working electrode of each of a first electrode system, a third electrode system, a fifth electrode system, a sixth electrode system, and a seventh electrode system.

Step A: Detection of Sample (Blood)

A voltage is applied between the electrode D and the electrode E, and the introduction of blood is detected based on a change in the current value accompanying the introduction of blood. After the introduction of the blood is detected, subsequent steps are started. The voltage applied in Step A is, for example, 0.05 to 1 V, and preferably 0.7 V. Then, glucose in the blood is allowed to react with glucose oxidoreductase for a certain period of time. It should be noted that Step A is optional.

Step B: Step of Measuring Blood Component Amount-Dependent Current Values

Figure 38:
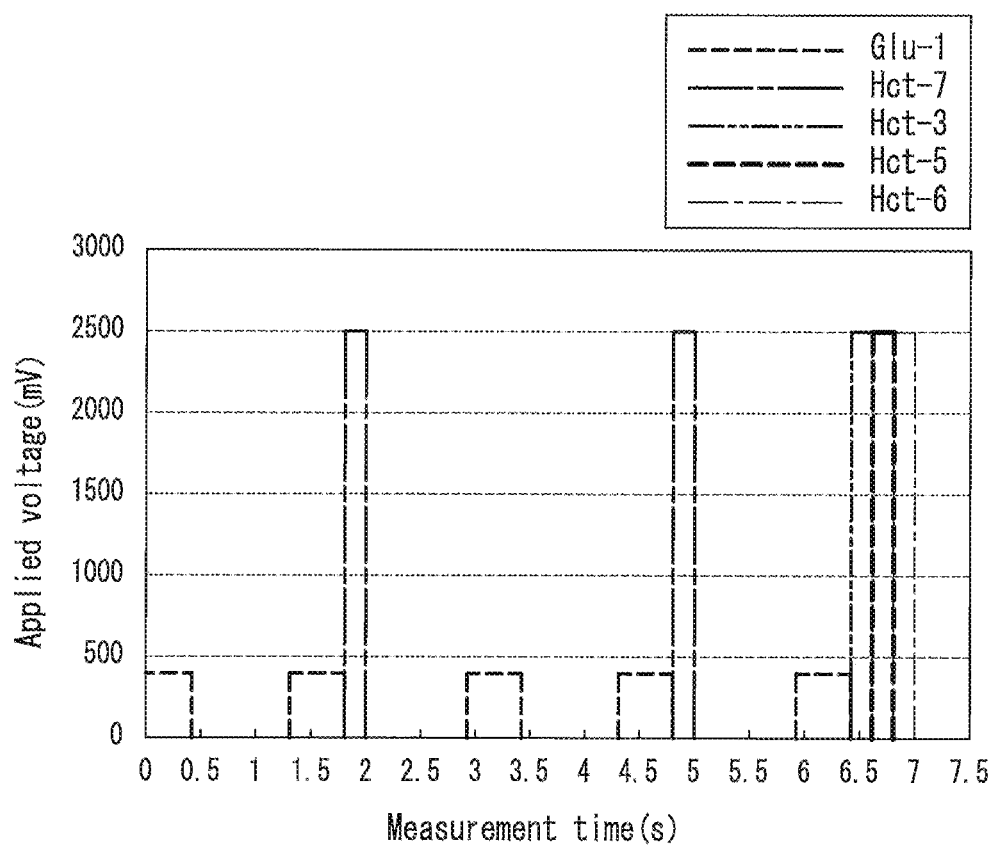
FIG. 38 is a diagram showing a change in voltage value over time in a voltage application pattern in Embodiment 5.

As shown in FIG. 38, after the glucose in the blood has been reacted with the glucose oxidoreductase for a certain period of time, the measuring device 2 applies a voltage to the first electrode system while controlling the voltage value and the application time of a first voltage (first step). The measuring device 2 starts to measure the current when a detection electrode system (the electrode D and the electrode E) detects the blood to be measured after the blood has been introduced into the biosensor 3.

At this time, the measuring device 2 changes the electrodes to be subjected to voltage application, the applied voltage, the application time, and the timing of voltage application as shown in FIG. 39. The first voltage is applied between the electrodes in the first electrode system (including the electrode C serving as the working electrode and the electrodes D and E serving as the counter electrodes). In FIG. 39, voltage application indicated with "Glu-1" corresponds to the voltage application in this first step. The first voltage is 400 mV. The first step of applying the first voltage to the first electrode system and detecting a first blood component amount-dependent current value is performed a plurality of times, e.g., five times.

In the case where the first step is performed at least twice, the first voltages may be different from each other. This is because the effects of interfering substances that react at different voltages can be observed.

The first blood component amount-dependent current values obtained by applying the first voltage to the first electrode system are used in a step of calculating the amount of the blood component to be described below.

Step C: Step of Measuring Hct

As shown in FIG. 38, after performing the step of measuring the first blood component amount-dependent current value (the first step), the measuring device 2 applies a voltage to the third electrode system while controlling the voltage value and the application time of a third voltage (third step). Although Step B is performed first and then Step C is performed in this example, Step C may be performed first and then Step B may be performed.

At this time, the measuring device 2 changes the electrodes to be subjected to voltage application, the applied voltage, the application time, and the timing of voltage application as shown in FIG. 39. The third voltage is applied between the electrodes in the third electrode system (including the electrode A serving as the working electrode and the electrode C serving as the counter electrode). In FIG. 39, voltage application indicated with "Hct-3" corresponds to the voltage application in this step. The third voltage is 2500 mV. A third hematocrit-dependent current value obtained by applying the third voltage to the third electrode system is used in the step of calculating the amount of the blood component to be described below.

In this Step C, in addition to performing the third step, a voltage is applied to the fifth electrode system while controlling the voltage value and the application time of a fifth voltage (fifth step). In FIG. 39, voltage application indicated with "Hct-5" corresponds to the voltage application in this fifth step. The fifth voltage is 2500 mV. A fifth hematocrit-dependent current value obtained by applying the fifth voltage to the fifth electrode system is used in the step of calculating the amount of the blood component to be described below.

In this Step C, in addition to performing the third step and the fifth step, a voltage is applied to the sixth electrode system while controlling the voltage value and the application time of a sixth voltage (sixth step). In FIG. 39, voltage application indicated with "Hct-6" corresponds to the voltage application in this sixth step. The sixth voltage is 2500 mV. A sixth hematocrit-dependent current value obtained by applying the sixth voltage to the sixth electrode system is used in the step of calculating the amount of the blood component to be described below.

In this Step C, in addition to performing the third step, the fifth step, and the sixth step, a voltage is applied to the seventh electrode system while controlling the voltage value and the application time of a seventh voltage (seventh step). In FIG. 39, voltage application indicated with "Hct-7" corresponds to the voltage application in this seventh step. The seventh voltage is 2500 mV. A seventh hematocrit-dependent current value obtained by applying the seventh voltage to the seventh electrode system is used in the step of calculating the amount of the blood component to be described below.

In this Step C, the third step, the fifth step, and the sixth step may be performed after the first step.

Also, in this Step C, the seventh step may be performed before the third step, the fifth step, and the sixth step.

Also, in this Step C, the seventh step may be performed after at least one of the first steps, and then the first step may be further performed.

It should be noted that, in this Embodiment 5, the electrode F that is coated with a polymer such as CMC only and on which the second reagent layer and the third reagent layer are not disposed, that is, a bare electrode, is used.

Step D: Step of Calculating Amount of Blood Component

The plurality of, e.g., the plurality of blood component amount-dependent current values obtained are processed as follows before they are used as the blood component amount-dependent current values.

A plurality of parameters (x1, x2, x3, . . . , x10) are calculated based on, for example, the extracted current values measured at the plurality of predetermined time points and the extracted temperature information of the biological information measuring device ("calculate predetermined parameters"), a correction amount is calculated using a multiple regression equation (e.g., Formula 1 below), and then a blood component amount-dependent current value is calculated.

$$y = ax1 + bx2 + cx3 \ldots + kx10 + l \quad \text{(Formula 1)}$$

(y denotes the correction amount, x1, x2, x3 . . . , and x10 denote parameters, and a, b, c, . . . and l denote coefficients.)

The amount of the blood component is obtained using the third Hct-dependent current value, the fifth Hct-dependent current value, the sixth Hct-dependent current value, and the seventh Hct-dependent current value obtained in Step C, and the first blood component-dependent current values obtained in Step B. Preferably, this is performed based on a calibration curve (including a calibration table) prepared beforehand. The thus-obtained amount of the blood component is displayed or stored in the measuring device.

After the amount of the blood component has been calculated, the biosensor is discarded and the display unit and the like are turned off. Thereafter, the measuring device is also turned off to complete the measurement of the component of the biological sample.

Embodiment 6A

Embodiment 6A is an example of the blood component amount measurement method 6 of the present invention.

The biosensor used in this method is the same as the third biosensor used in Embodiment 4. In Embodiment 6A, the electrode 72, the electrode 73, the electrode 74, the electrode 75, the electrode 76, and the electrode 77 of the third biosensor are used as an electrode A, an electrode C, an electrode D, an electrode E, an electrode F, and an electrode G, respectively. FIG. 43 shows which of tire electrodes is used as the counter electrode and the working electrode of each of a first electrode system, a second electrode system, a third electrode system, a fifth electrode system, and a sixth electrode system.

Step A: Detection of Sample (Blood)

A voltage is applied between the electrode D and the electrode E, and the introduction of blood is detected based on a change in the current value accompanying the introduction of blood. After the introduction of the blood is detected, subsequent steps are started. The voltage applied in Step A is, for example, 0.05 to 1 V, and preferably 0.7 V. Then, glucose in the blood is allowed to react with glucose oxidoreductase for a certain period of time. It should be noted that Step A is optional.

Step B: Step of Measuring Blood Component Amount-Dependent Current Values

Figure 41:
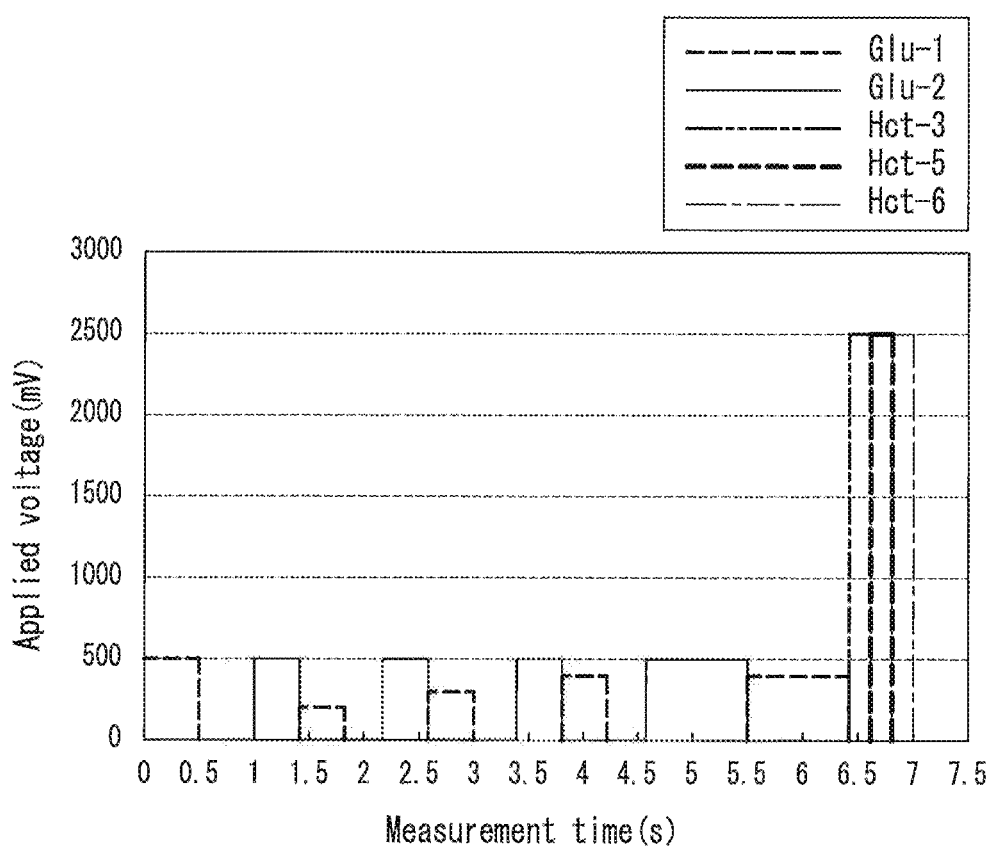
FIG. 41 is a diagram showing a change in voltage value over time in a voltage application pattern in Embodiment 6A.

As shown in FIG. 41, after the glucose in the blood has been reacted with the glucose oxidoreductase (or a certain period of time, the measuring device 2 applies a voltage to the first electrode system while controlling the voltage value and the application time of a first voltage (first step). The measuring device 2 starts to measure the current when a detection electrode system (the electrode D and the electrode E) detects the blood to be measured after the blood has been introduced into the biosensor 3.

At this time, the measuring device 2 changes the electrodes to be subjected to voltage application, the applied voltage, the application time, and the timing of voltage application as shown in FIG. 42. The first voltage is applied between the electrodes in the first electrode system (including the electrode C serving as the working electrode and the electrodes D and E serving as the counter electrodes). In FIG. 42, voltage application indicated with "Glu-1" corresponds to the voltage application in this first step. The first voltage is 200 mV to 500 mV. The first step of applying the first voltage to the first electrode system and detecting a first blood component amount-dependent current value is performed a plurality of times, e.g., five times.

In the case where the first step is performed at least twice, the first voltages may be different from each other. This is because the effects of interfering substances that react at different voltages can be observed.

In this Step B, in addition to performing the first step, a voltage is applied to the second electrode system while controlling the voltage value and the application time of a second voltage (second step). In FIG. 42, voltage application indicated with "Glu-2" corresponds to the voltage application in this second step. The second voltage is 500 mV. The first step of applying the second voltage to the second electrode system and detecting a second blood component amount-dependent current value is performed a plurality of times, e.g., four times. The first steps and the second steps are performed in turn as follows, for example: the first step, the second step, the first step, the second step, and so on. In the case where the second step is performed at least twice, the second voltages may be equal to each other. This is because, for example, transition of the response value (current value) on the time axis can be observed.

In this Step B, the first step may be performed at least twice, the second step may be performed at least twice, and the second steps and the first steps may be performed alternately.

In this Step B, the order of performing the first step and the second step may be changed. That is, although the first step is performed first in the example illustrated in FIG. 41, the second step may be performed first.

The first blood component amount-dependent current values obtained by applying the first voltage to the first electrode system and the second blood component amount-dependent current values obtained by applying the second voltage to the second electrode system are used in a step of calculating the amount of the blood component to be described below.

Step C: Step of Measuring Hct

As shown in FIG. 41, after performing the step of measuring the first blood component amount-dependent current value (the first step), the measuring device 2 applies a voltage to the third electrode system while controlling the voltage value and the application time of a third voltage (third step). Although Step B is performed first and then Step C is performed in this example, Step C may be performed first and then Step B may be performed.

At this time, the measuring device 2 changes the electrodes to be subjected to voltage application, the applied voltage, the application time, and the timing of voltage application as shown in FIG. 42. The third voltage is applied between the electrodes in the third electrode system (including the electrode A serving as the working electrode and the electrode C serving as the counter electrode). In FIG. 42, voltage application indicated with "Hct-3" corresponds to the voltage application in this step. The third voltage is 2500 mV. A third hematocrit-dependent current value obtained by applying the third voltage to the third electrode system is used in the step of calculating the amount of the blood component to be described below.

In this Step C, in addition to performing the third step, a voltage is applied to the fifth electrode system while controlling the voltage value and the application time of a fifth voltage (fifth step). In FIG. 42, voltage application indicated with "Hct-5" corresponds to the voltage application in this fifth step. The fifth voltage is 2500 mV. A fifth hematocrit-dependent current value obtained by applying the fifth voltage to the fifth electrode system is used in the step of calculating the amount of the blood component to be described below.

In this Step C, in addition to performing the third step and the fifth step, a voltage is applied to the sixth electrode system while controlling the voltage value and the application time of a sixth voltage (sixth step). In FIG. 42, voltage application indicated with "Hct-6" corresponds to the voltage application in this sixth step. The sixth voltage is 2500 mV. A sixth hematocrit-dependent current value obtained by applying the sixth voltage to the sixth electrode system is used in the step of calculating the amount of the blood component to be described below.

In this Step C, the third step, the fifth step, and the sixth step may be performed after all of the first steps.

Also, in this Step C, the third step, the fifth step, and the sixth step may be performed after all of the second steps.

It should be noted that, in this Embodiment 6A, the electrode F that is coated with a polymer such as CMC only and on which the second reagent layer and the third reagent layer are not disposed, that is, a bare electrode, is used.

Step D: Step of Calculating Amount of Blood Component

The plurality of, e.g., the plurality of blood component amount-dependent current values obtained are processed as follows before they are used as the blood component amount-dependent current values.

A plurality of parameters (x1, x2, x3, . . . , x10) are calculated based on, for example, the extracted current values measured at the plurality of predetermined time points and the extracted temperature information of the biological information measuring device ("calculate predetermined parameters"), a correction amount is calculated using a multiple regression equation (e.g., Formula 1 below), and then a blood component amount-dependent current value is calculated.

$$y = ax1 + bx2 + cx3 \ldots + kx10 + l \quad \text{(Formula 1)}$$

(y denotes the correction amount, x1, x2, x3 . . . , and x10 denote parameters, and a, b, c, . . . and l denote coefficients.)

The amount of the blood component is obtained using the third Hct-dependent current value, the fifth Hct-dependent current value, and the sixth Hct-dependent current value obtained in Step C, and the first blood component-dependent current values and the second blood component-dependent current values obtained in Step B. Preferably, this is performed based on a calibration curve (including a calibration table) prepared beforehand. The thus-obtained amount of the blood component is displayed or stored in the measuring device.

After the amount of the blood component has been calculated, the biosensor is discarded and the display unit and the like are turned off. Thereafter, the measuring device is also turned off to complete the measurement of the component of the biological sample.

Embodiment 6B

Embodiment 6B is an example of the blood component amount measurement method 6 of the present invention.

The biosensor used in this method is the same as the third biosensor used in Embodiment 4. In Embodiment 6B, the electrode 72, the electrode 73, the electrode 74, the electrode 75, the electrode 76, and the electrode 77 of the third biosensor are used as an electrode A, an electrode C, an electrode D, an electrode E, an electrode F, and an electrode G, respectively. FIG. 46 shows which of the electrodes is used as the counter electrode and the working electrode of each of a first electrode system, a second electrode system, a third electrode system, a fifth electrode system, and a sixth electrode system.

Figure 44:
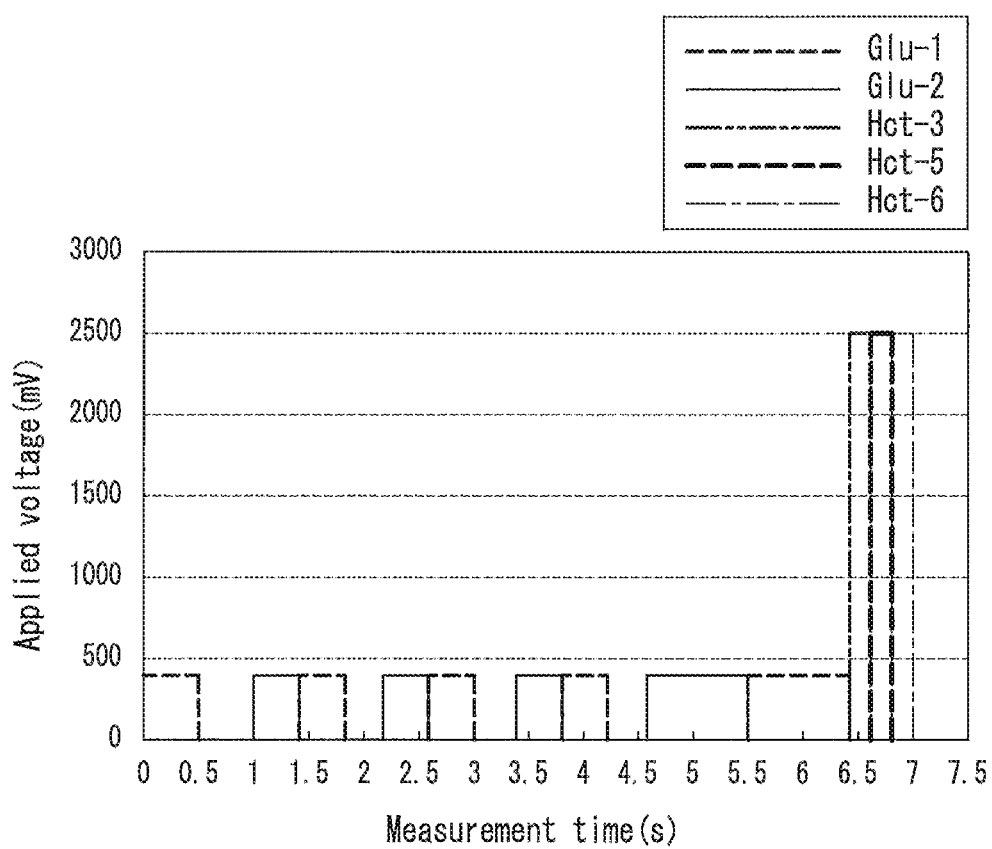
FIG. 44 is a diagram showing a change in voltage value over time in a voltage application pattern in Embodiment 6B.

In Embodiment 6B, the measuring device 2 changes the electrodes to be subjected to voltage application, the applied voltage, the application time, and the timing of voltage application as shown in FIG. 44. A first voltage is applied between the electrodes in the first electrode system (including the electrode C serving as the working electrode and the electrodes E and D serving as the counter electrodes). In FIG. 45, voltage application indicated with "Glu-1" corresponds to the voltage application in this first step. The first voltage is 400 mV. The first step of applying the first voltage to the first electrode system and detecting a first blood component amount-dependent current value is performed a plurality of times, e.g., five times. In this Step B, at the time different from the first step, a voltage is applied to the second electrode system while controlling the voltage value and the application time of a second voltage (second step). In FIG. 45, voltage application indicated with "Glu-2" corresponds to the voltage application in this second step. The second voltage is 400 mV. The second ship of applying the second voltage to the second electrode system and detecting a blood component amount-dependent current value is performed a plurality of times, e.g., four times.

Embodiment 6B is the same as Embodiment 6A, except that the first voltage in the first step and the second voltage in the second step are constant.

Embodiment 6C

Embodiment 6C is on example of the blood component amount measurement method 6 of the present invention.

The biosensor used in this method is the same us the third biosensor used in Embodiment 4. In Embodiment 6C, the electrode 72, the electrode 73, the electrode 74, the electrode 75, the electrode 76, and the electrode 77 of the third biosensor are used as an electrode A, an electrode C, an electrode D, an electrode E, an electrode F, and an electrode G, respectively. FIG. 49 shows which of the electrodes is used as the counter electrode and the working electrode of each of a first electrode system, a second electrode system, a third electrode system, a fifth electrode system, and a sixth electrode system.

Figure 47:
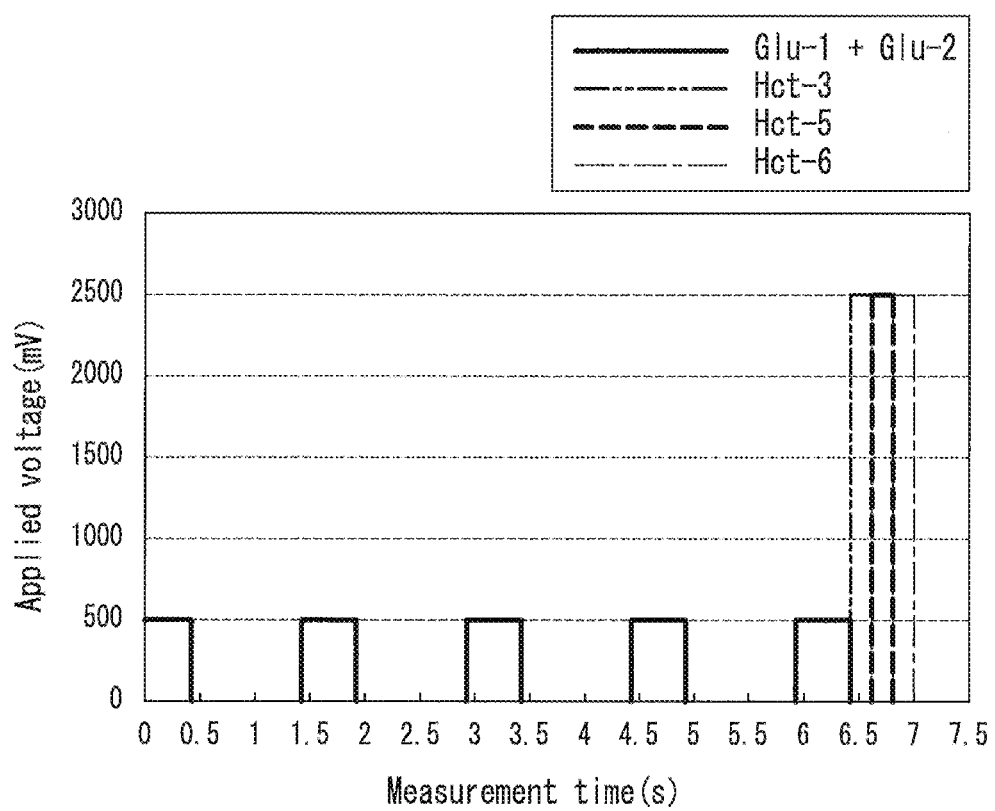
FIG. 47 is a diagram showing a change in voltage value over time in a voltage application pattern in Embodiment 6C.

In Embodiment 6C, the measuring device 2 changes the electrodes to be subjected to voltage application, the applied voltage, the application time, and the timing of voltage application as shown in FIG. 47. In FIG. 48, voltage application indicated with "Glu-1" corresponds to the voltage application in this first step. A first voltage is 500 mV. The first step of applying the first voltage to the first electrode system and detecting a first blood component amount-dependent current value is performed a plurality of times, e.g., five times. In this Step B, at the same time as the first step, a voltage is applied to the second electrode system while controlling the voltage value and the application time of a second voltage (second step). In FIG. 48, voltage application indicated with "Glu-2" corresponds to the voltage application in this second step. The second voltage is 500 mV. The second step of applying the second voltage to the second electrode system and detecting a blood component amount-dependent current value is performed a plurality of times, e.g., five times.

Embodiment 6C is the same as Embodiment 6B, except that the first step and the second step are performed simultaneously.

In this Step C, the third step, the fifth step, and the sixth step may be performed after all of the first steps and the second steps.

Embodiment 6D

Embodiment 6D is an example of the blood component amount measurement method 6 of the present invention.

The biosensor used in this method is the same as the third biosensor used in Embodiment 4. In Embodiment 6D, the electrode 72, the electrode 73, the electrode 74, the electrode 75, the electrode 76, and the electrode 77 of the third biosensor are used as an electrode A, an electrode C, an electrode D, an electrode E, an electrode F, and an electrode G, respectively. FIG. 52 shows which of the electrodes is used as the counter electrode and the working electrode of each of a first electrode system, a second electrode system, a third electrode system, a fifth electrode system, and a sixth electrode system.

Figure 50:
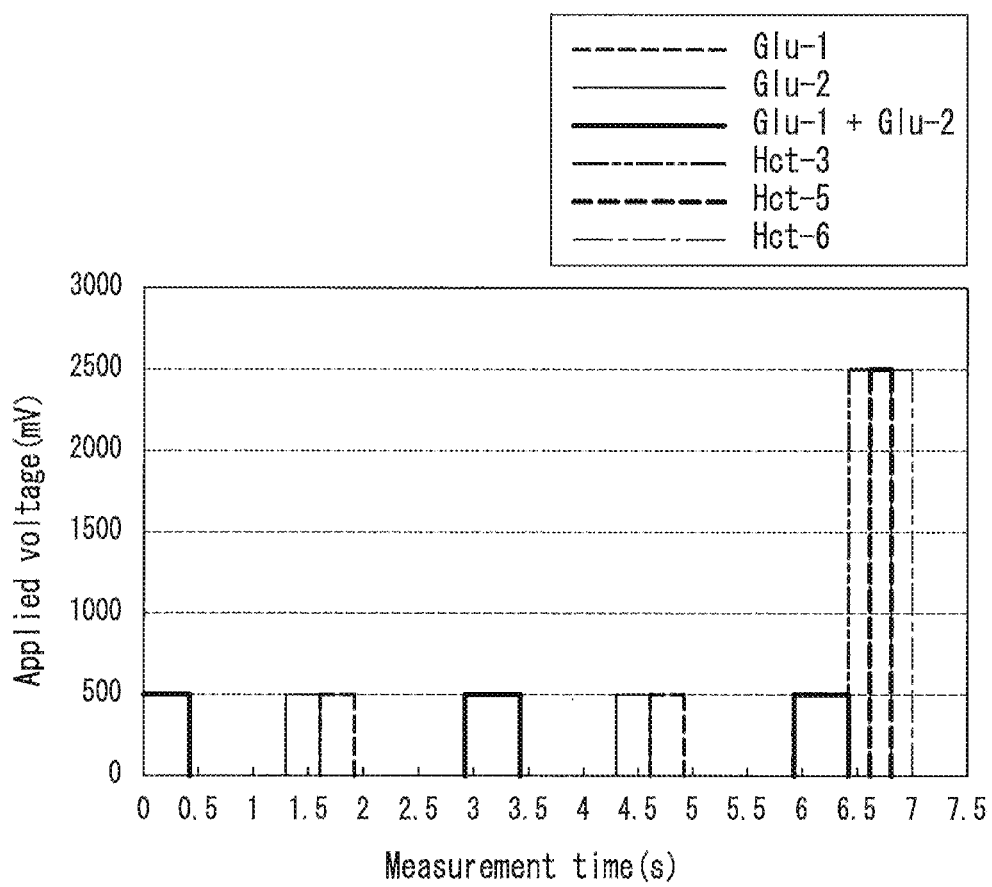
FIG. 50 is a diagram showing a change in voltage value over time in a voltage application pattern in Embodiment 6D.

In Embodiment 6D, the measuring device 2 changes the electrodes to be subjected to voltage application, the applied voltage, the application time, and the timing of voltage application as shown in FIG. 50. In FIG. 51, voltage application indicated with "Glu-1" corresponds hr the voltage application in this first step. A first voltage is 500 mV. The first step of applying the first voltage to the first electrode system and detecting a first blood component amount-dependent current value is performed a plurality of times, e.g., five times. In this step B, at the same time as the first step or at the time different from the first step, a voltage is applied to the second electrode system while controlling the voltage value and the application time of a second voltage (second step). In FIG. 51, voltage application indicated with "Glu-2" corresponds to the voltage application in this second step. The second voltage is 500 mV. The second step of applying the second voltage to the second electrode system and detecting a blood component amount-dependent current value is performed a plurality of times, e.g., five times.

Embodiment 6D is the same as Embodiment 6B, except that portions of the first steps and the second steps are performed simultaneously.

In this Step C, the third step, the fifth step, and the sixth step may be performed after all of the first steps.

In this Step C, the third step, the fifth step, and the sixth step may be performed after all of the second steps.

Embodiment 7A

Embodiment 7A is on example of the blood component amount measurement method 7 of the present invention.

The biosensor used in this method is the same as the third biosensor used in Embodiment 4. In Embodiment 7A, the electrode 72, the electrode 73, the electrode 74, the electrode 75, the electrode 76, and the electrode 77 of the third biosensor are used as an electrode A, an electrode C, an electrode D, an electrode E, an electrode F, and an electrode G, respectively. FIG. 55 shows which of the electrodes is used as the counter electrode and the working electrode of each of a first electrode system, a second electrode system, a third electrode system, a fifth electrode system, a sixth electrode system and a seventh electrode system.

Step A: Detection of Sample (Blood)

A voltage is applied between the electrode D and the electrode E, and the introduction of blood is detected based on a change in the current value accompanying the introduction of blood. After the introduction of the blood is detected, subsequent steps are started. The voltage applied in Step A is, for example, 0.05 to 1 V, and preferably 0.7 V. Then, glucose in the blood is allowed to react with glucose oxidoreductase fer a certain period of time. It should be noted that Step A is optional.

Step B: Step of Measuring Blood Component Amount-Dependent Current Values

Figure 53:
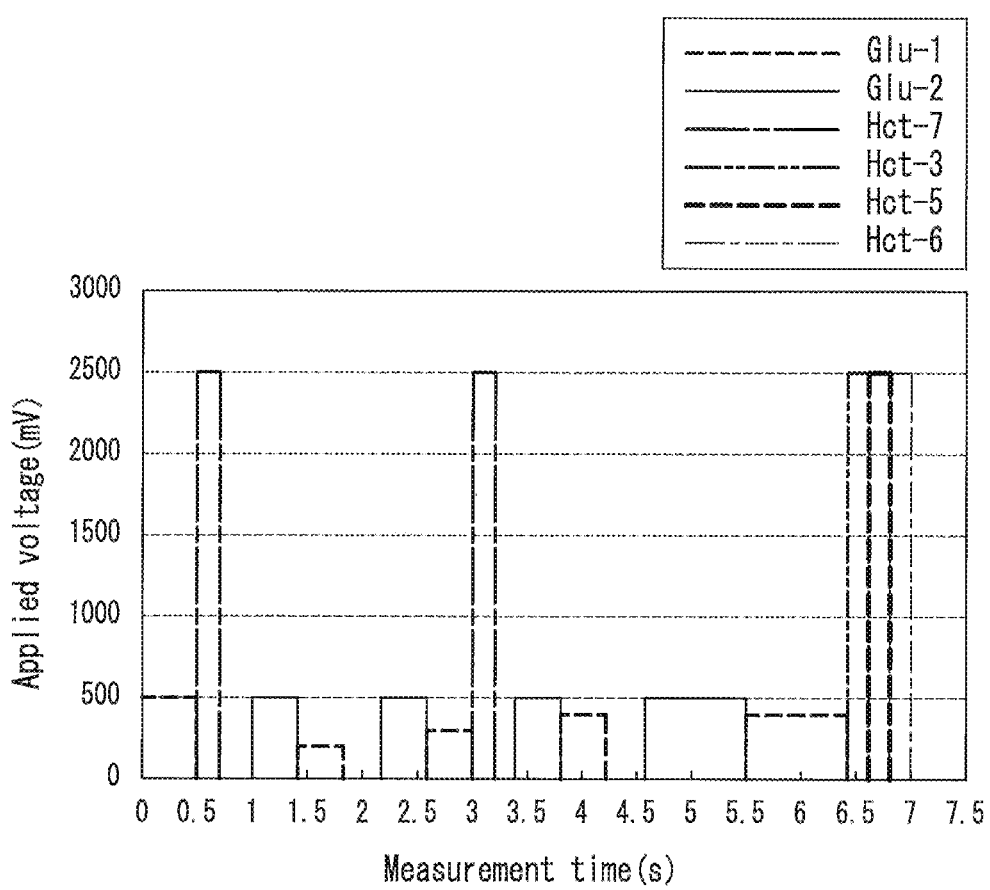
FIG. 53 is a diagram showing a change in voltage value over time in a voltage application pattern in Embodiment 7A.

As shown in FIG. 53, after the glucose in the blood has been reacted with the glucose oxidoreductase fer a certain period of time, the measuring device 2 applies a voltage to the first electrode system while controlling the voltage value and the application time of a first voltage (first step). The measuring device 2 starts to measure the current when a detection electrode system (the electrode D and the electrode E) detects the blood to be measured after the blood has been introduced into the biosensor 3.

At this time, the measuring device 2 changes the electrodes to be subjected to voltage application, the applied voltage, the application time, and the timing of voltage application as shown in FIG. 54. The first voltage is applied between the electrodes in the first electrode system (including the elect rode C serving as the working electrode and the electrodes D and E serving as the counter electrodes). In FIG. 54, voltage application indicated with "Glu-1" corresponds to the voltage application in this first step. The first voltage is 200 mV to 500 mV. The first step of applying the first voltage to the first electrode system and detecting a first blood component amount-dependent current value is performed a plurality of times, e.g., five times.

In the case where the first step is performed at least twice, the first voltages may be different from each other. This is because the effects of interfering substances that react at different voltages can be observed.

In this Step B, in addition to performing the first step, a voltage is applied to the second electrode system while controlling the voltage value and the application time of a second voltage (second step). In FIG. 54, voltage application indicated with "Glu-2" corresponds to the voltage application in this second step. The second voltage is 500 mV. The first step of applying the second voltage to the second electrode system and detecting a second blood component amount-dependent current value is performed a plurality of times, e.g., four times. The first steps and the second steps are performed in turn as follows, for example: the first step, the second step, the first step, the second step, and so on. In the case where the second step is performed at least twice, the second voltages may be equal to each other. This is because, for example, transition of the response value (current value) on the time axis can be observed.

In this Step B, the first step may be performed at least twice, the second step may be performed at least twice, and the second steps and the first steps may be performed alternately.

In this Step B, the order of performing the first step and the second step may be changed. That is, although the first step is performed first in the example illustrated in FIG. 54, the second step may be performed first.

The first blood component amount-dependent current values obtained by applying the first voltage to the first electrode system and the second blood component amount-dependent current values obtained by applying the second voltage to the second electrode system are used in a step of calculating the amount of the blood component to be described below.

Step C: Step of Measuring Hct

As shown in FIG. 53, after performing the steps of measuring the blood component amount-dependent current values (the first step and the second step), the measuring device 2 applies a voltage to the third electrode system while controlling the voltage value and the application time of a third voltage (third step). Although Step B is performed first and then Step C is performed in this example, Step C may be performed first and then Step B may be performed.

At this time, the measuring device 2 changes the electrodes to be subjected to voltage application, the applied voltage, the application time, and the timing of voltage application as shown in FIG. 54. The third voltage is applied between the electrodes in the third electrode system (including the electrode A serving as the working electrode and the electrode C serving as the counter electrode). In FIG. 54, voltage application indicated with "Hct-3" corresponds to the voltage application in this step. The third voltage is 2500 mV. A third hematocrit-dependent current value obtained by applying the third voltage to the third electrode system is used in the step of calculating the amount of the blood component to be described below.

In this Step C, in addition to performing the third step, a voltage is applied to the fifth electrode system while controlling the voltage value and the application time of a fifth voltage (fifth step). In FIG. 54, voltage application indicated with "Hct-5" corresponds to the voltage application in this fifth step. The fifth voltage is 2500 mV. A fifth hematocrit-dependent current value obtained by applying the fifth voltage to the fifth electrode system is used in the step of calculating the amount of the blood component to be described below.

In this Step C, in addition to performing the third step and the fifth step, a voltage is applied to the sixth electrode system while controlling the voltage value and the application time of a sixth voltage (sixth step). In FIG. 54, voltage application indicated with "Hct-6" corresponds to the voltage application in this sixth step. The sixth voltage is 2500 mV. A sixth hematocrit-dependent current value obtained by applying the sixth voltage to the sixth electrode system is used in the step of calculating the amount of the blood component to be described below.

In this Step C, in addition to performing the third step, the fifth step, and the sixth step, a voltage is applied to the seventh electrode system while controlling the voltage value and the application time of a seventh voltage (seventh step). In FIG. 39, voltage application indicated with "Hct-7" corresponds to the voltage application in this seventh step. The seventh voltage is 2500 mV. A seventh hematocrit-dependent current value obtained by applying the seventh voltage to the seventh electrode system is used in the step of calculating the amount of the blood component to be described below.

Also, in this Step C, the third step, the fifth step, and the sixth step may be performed after all of the first steps.

Also, in this Step C, the third step, the fifth step, and the sixth step may be performed after all of the second steps.

Also, in this Step C, the seventh step may be performed before the third step, the fifth step, and the sixth step.

Also, in this Step C, the seventh step may be performed after at least one of the first steps, and then the first step may be further performed.

It should be noted that, in this Embodiment 7A, the electrode F that is coated with a polymer such as CMC only and on which the second reagent layer and the third reagent layer are not disposed, that is, a bare electrode, is used.

Step D: Step of Calculating Amount of Blood Component

The plurality of, e.g., the plurality of blood component amount-dependent current values obtained are processed as follows before they are used as the blood component amount-dependent current values.

A plurality of parameters (x1, x2, x3, . . . , x10) are calculated based on, for example, the extracted current values measured at the plurality of predetermined time points and the extracted temperature information of the biological information measuring device ("calculate predetermined parameters"), a correction amount is calculated using a multiple regression equation (e.g., Formula 1 below), and then a blood component amount-dependent current value is calculated.

$$y = ax1 + bx2 + cx3 \ldots + kx10 + l \quad \text{(Formula 1)}$$

(y denotes the correction amount, x1, x2, x3 and x10 denote parameters, and a, b, c, . . . and l denote coefficients.)

The amount of the blood component is obtained using the third Hct-dependent current value, the fifth Hct-dependent current value, the sixth Hct-dependent current value, and the seventh Hct-dependent current value obtained in Step C, and the first blood component-dependent current values and the second blood component-dependent current values obtained in Step B. Preferably, this is performed based on a calibration curve (including a calibration table) prepared beforehand. The thus-obtained amount of the blood component is displayed or stored in the measuring device.

After the amount of the blood component has been calculated, the biosensor is discarded and the display unit and the like are turned off. Thereafter, the measuring device is also turned off to complete the measurement of the component of the biological sample.

Embodiment 7B

Embodiment 7B is an example of the blood component amount measurement method 7 of the present invention.

The biosensor used in this method is the same as the third biosensor used in Embodiment 4. In Embodiment 7B, the electrode 72, the electrode 73, the electrode 74, the electrode 75, the electrode 76, and the electrode 77 of the third biosensor are used as an electrode A, an electrode C, an electrode D, an electrode E, an electrode F, and on electrode G, respectively. FIG. 58 shows which of the electrodes is used as the counter electrode and the working electrode of each of a first electrode system, a second electrode system, a third electrode system, a fifth electrode system, a sixth electrode system, and a seventh electrode system.

Figure 56:
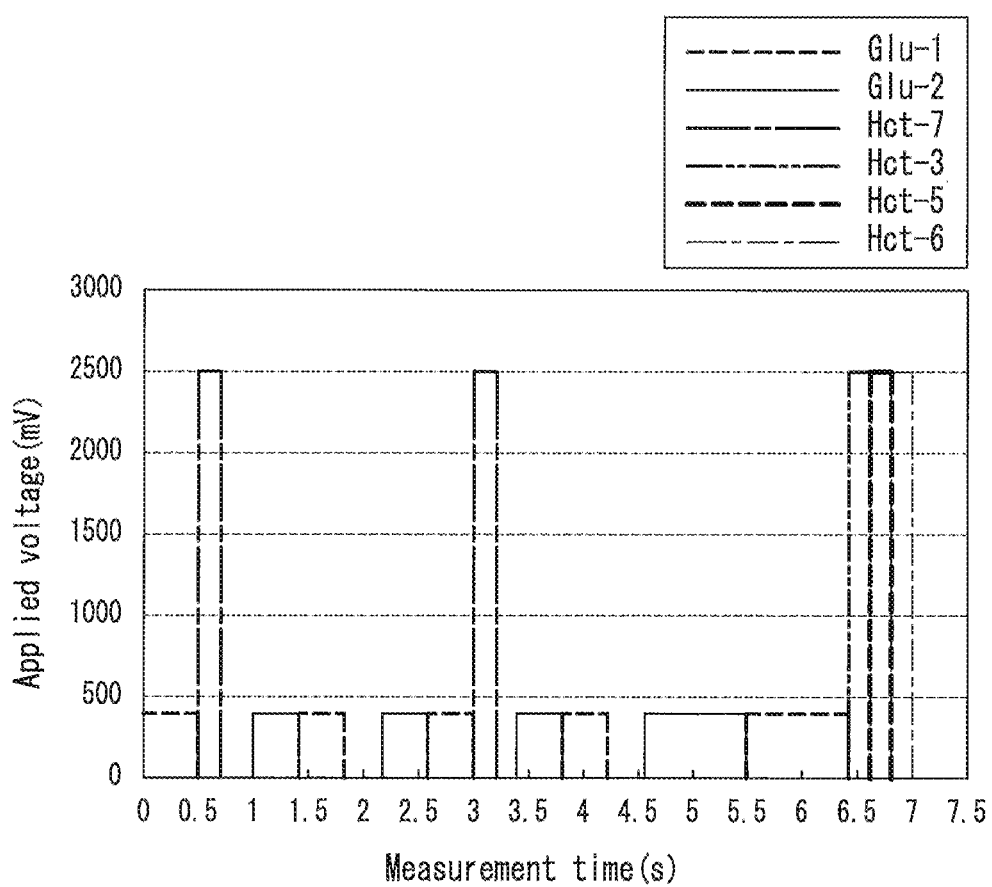
FIG. 56 is a diagram showing a change in voltage value over time in a voltage application pattern in Embodiment 7B.

In Embodiment 7B, the measuring device 2 changes the electrodes to be subjected to voltage application, the applied voltage, the application time, and the timing of voltage application as shown in FIG. 56. A first voltage is applied between the electrodes in the first electrode system (including the electrode C serving as the working electrode and the electrodes E and D serving as the counter electrodes). In FIG. 57, voltage application indicated with "Glu-1" corresponds to the voltage application in this first step. The first voltage is 400 mV. The first step of applying the first voltage to the first electrode system and detecting a first blood component amount-dependent current value is performed a plurality of times, e.g., five times. In this Step B, at the time different from the first step, a voltage is applied to the second electrode system while controlling the voltage value and the application time of a second voltage (second step). In FIG. 57, voltage application indicated with "Glu-2" corresponds to the voltage application in this second step. The second voltage is 400 mV. The second step of applying the second voltage to the second electrode system and detecting a blood component amount-dependent current value is performed a plurality of times, e.g., four times.

Embodiment 7B is the same as Embodiment 7A, except that the first voltage in the first step and the second voltage in the second step are constant.

Embodiment 7C

Embodiment 7C is an example of the blood component amount measurement method 7 of the present invention.

The biosensor used in this method is the same as the third biosensor used in Embodiment 4. In Embodiment 7C, FIG. 61 shows which of the electrodes is used as the counter electrode and the working electrode of each of a first electrode system, a second electrode system, a third electrode system, a fifth electrode system, a sixth electrode system, and a seventh electrode system.

Figure 59:
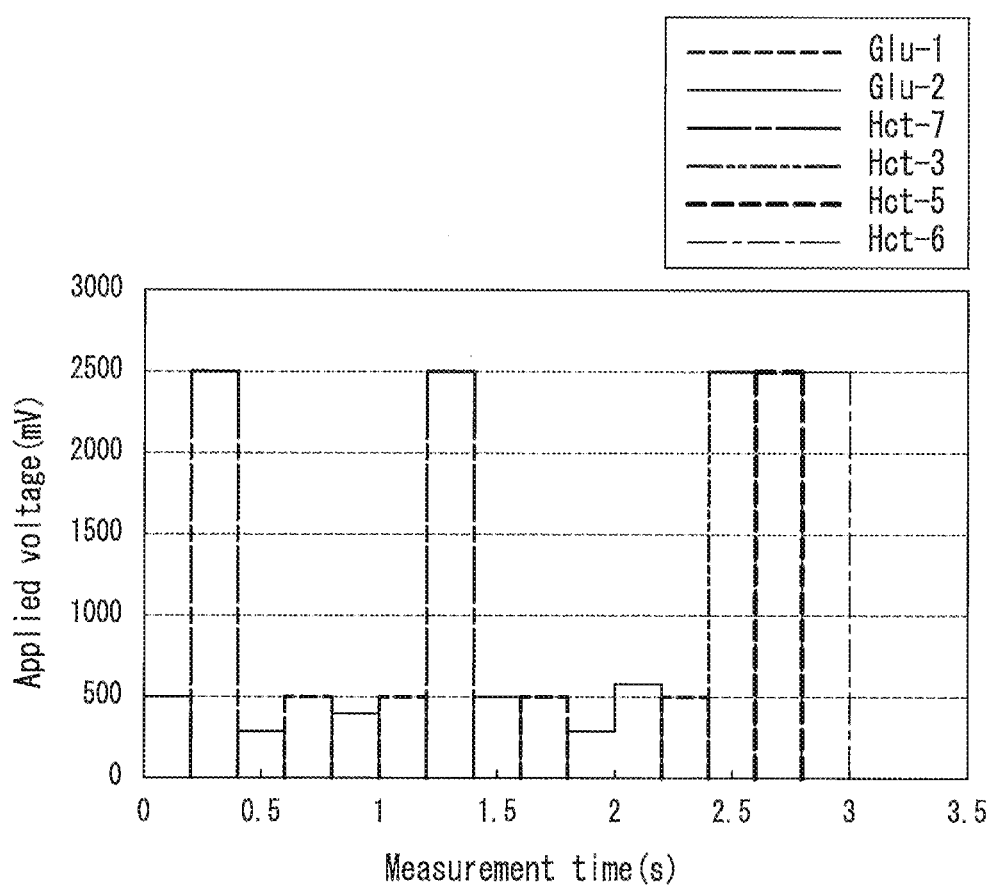
FIG. 59 is a diagram showing a change in voltage value over time in a voltage application pattern in Embodiment 7C.

In Embodiment 7C, the measuring device 2 changes the electrodes to be subjected to voltage application, the applied voltage, the application time, and the timing of voltage application as shown in FIG. 59. In FIG. 60, voltage application indicated with "Glu-1" corresponds to the voltage application in this first step. A first voltage is 500 mV. The first step of applying the first voltage to the first electrode system and detecting a first blood component amount-dependent current value is performed a plurality of times, e.g., four times. In this Step B, at the time different from the first step, a voltage is applied to the second electrode system while controlling the voltage value and the application time of a second voltage (second step). In FIG. 69, voltage application indicated with "Glu-2" corresponds to the voltage application in this second step. The second voltage is 300 mV to 500 mV. The second step of applying the second voltage to the second electrode system and detecting a blood component amount-dependent current value is performed a plurality of times, e.g., six times.

Embodiment 7C is the same as Embodiment 7B, except that the first voltage and the second voltage are different in the magnitude.

In this Step C, the third step, the fifth step, and the sixth step may be performed after all of the first steps.

Also in this Step C, the third step, the fifth step, and the sixth step may be performed after all of the second steps.

Also, in this Step C, the seventh step may be performed before the third step, the fifth step, and the sixth step.

Also, in this Step C, the seventh step may be performed after at least one of the first steps, and then the first step may be further performed.

INDUSTRIAL APPLICABILITY

As described above, the biosensor production method according to the present invention can produce a biosensor capable of measuring a component of a biological sample with higher accuracy. Accordingly, the production method of the present invention can be used preferably in all fields involving blood component measurement, such as biology, biochemistry, and medicine, and is particularly suited to the field of clinical examinations.

LIST OF REFERENCE NUMERALS

2 Measuring device
3 Sensor
4 Display portion
5 Insertion port
10 Blood supply port
101, 111, 121 Insulating substrate
102 Spacer
103 Cover
6, 36, 66 First reagent layer
7, 37, 67 Second reagent layer
19, 49, 79 Location of the first reagent layer
20, 50, 80 Location of the second reagent layer
8 Channel
9 Air hole
12, 42, 72 Electrode A
13, 43, 73 Electrode C
14, 44, 74 Electrode D
15, 45, 75 Electrode E
16, 46, 76 Electrode G
17, 77 Electrode F
206 Input terminal portion
230 A/D conversion unit
231 Determination means
232 Display unit
233 Power supply unit
234 Memory
235 Clock
236 Correction means
237 Voltage application unit 238 Current-voltage conversion unit
239 Control unit
302 measuring device

The invention claimed is:

1. A method for measuring the amount of a blood component in blood using a biosensor,
the biosensor comprising:
a first electrode system for measuring a blood component amount-dependent current value, the first electrode system including a first working electrode and a first counter electrode;
a second electrode system for measuring a blood component amount-dependent current value, the second electrode system including a second working electrode and a second counter electrode; and
a third electrode system for measuring a hematocrit-dependent current value, the third electrode system including a third working electrode and a third counter electrode,
wherein a first reagent layer is disposed on the first electrode system,
a second reagent layer is disposed on the second electrode system,
the first reagent layer and the second reagent layer are disposed spaced apart from each other,
the first reagent layer and the second reagent layer each contain a reagent for measuring the amount of the blood component in the blood,
at least one of the first counter electrode, the second working electrode, and the second counter electrode is used as the third working electrode, and
at least one of the first working electrode, the first counter electrode, and the second counter electrode is used as the third counter electrode,
the method comprising:
a first step of applying a first voltage to the first electrode system and detecting a first blood component amount-dependent current value;
a second step of applying a second voltage to the second electrode system and detecting a second blood component amount-dependent current value;
a third step of applying a third voltage to the third electrode system and detecting a third hematocrit-dependent current value; and
a step of calculating the amount of the blood component using the first blood component amount-dependent current value, the second blood component amount-dependent current value, and the third hematocrit-dependent current value,
wherein all portions of the first step and the second step are simultaneously performed,
the first step is performed at least twice,
the second step is performed at least twice, and
two or more first blood component amount-dependent current values obtained are used as the first blood component amount-dependent current values in the step of calculating the amount of the blood component.

2. The method according to claim 1,
wherein
two or more second blood component amount-dependent current values obtained are used as the second blood component amount-dependent current values in the step of calculating the amount of the blood component.

3. The method according to claim 1,
wherein the first reagent layer and the second reagent layer each contain a mediator.

4. The method according to claim 1,
wherein the first reagent layer and the second reagent layer further contain an oxidoreductase.

5. A method for measuring the amount of a blood component in blood using a biosensor,
the biosensor comprising:
a first electrode system for measuring a blood component amount-dependent current value, the first electrode system including a first working electrode and a first counter electrode;
a second electrode system for measuring a blood component amount-dependent current value, the second electrode system including a second working electrode and a second counter electrode; and
a third electrode system for measuring a hematocrit-dependent current value, the third electrode system including a third working electrode and a third counter electrode,
wherein a first reagent layer is disposed on the first electrode system,
a second reagent layer is disposed on the second electrode system,
the first reagent layer and the second reagent layer are disposed spaced apart from each other,
the first reagent layer and the second reagent layer each contain a reagent for measuring the amount of the blood component in the blood,
at least one of the first counter electrode, the second working electrode, and the second counter electrode is used as the third working electrode, and
at least one of the first working electrode, the first counter electrode, and the second counter electrode is used as the third counter electrode,
the method comprising:
a first step of applying a first voltage to the first electrode system and detecting a first blood component amount-dependent current value;
a second step of applying a second voltage to the second electrode system and detecting a second blood component amount-dependent current value;
a third step of applying a third voltage to the third electrode system and detecting a third hematocrit-dependent current value; and
a step of calculating the amount of the blood component using the first blood component amount-dependent current value, the second blood component amount-dependent current value, and the third hematocrit-dependent current value,
wherein the first step is performed at least twice,
the second step is performed at least twice,
portions of the first steps and the second steps are simultaneously performed, and
two or more first blood component amount-dependent current values obtained are used as the first blood component amount-dependent current values in the step of calculating the amount of the blood component.

6. The method according to claim 5,
wherein two or more second blood component amount-dependent current values obtained are used as the second blood component amount-dependent current values in the step of calculating the amount of the blood component.

7. The method according to claim 5,
wherein the first reagent layer and the second reagent layer each contain a mediator.

8. The method according to claim 5,
wherein the first reagent layer and the second reagent layer further contain an oxidoreductase.

9. A method for measuring the amount of a blood component in blood using a biosensor,
the biosensor comprising:
a first electrode system for measuring a blood component amount-dependent current value, the first electrode system including a first working electrode and a first counter electrode;
a second electrode system for measuring a blood component amount-dependent current value, the second electrode system including a second working electrode and a second counter electrode; and
a third electrode system for measuring a hematocrit-dependent current value, the third electrode system including a third working electrode and a third counter electrode,
a fourth electrode system for measuring a hematocrit-dependent current value, the fourth electrode system including a fourth working electrode and a fourth counter electrode,
wherein at least one of the first counter electrode, the second working electrode, and the second counter electrode is used as the third working electrode,
at least one of the first working electrode, the first counter electrode, and the second counter electrode is used as the third counter electrode,
the first counter electrode is used as the fourth working electrode,
the second counter electrode is used as the fourth counter electrode,
a first reagent layer is disposed on the first electrode system,
a second reagent layer is disposed on the second electrode system,
the first reagent layer and the second reagent layer are disposed spaced apart from each other,
the first reagent layer and the second reagent layer each contain a reagent for measuring the amount of the blood component in the blood,
the method comprising:
a first step of applying a first voltage to the first electrode system and detecting a first blood component amount-dependent current value;
a second step of applying a second voltage to the second electrode system and detecting a second blood component amount-dependent current value;
a third step of applying a third voltage to the third electrode system and detecting a third hematocrit-dependent current value;
the method further includes a fourth step of applying a fourth voltage to the fourth electrode system and detecting a fourth hematocrit-dependent current value; and
a step of calculating the amount of the blood component,
wherein the first step is performed at least twice,
two or more first blood component amount-dependent current values obtained are used as the first blood component amount-dependent current values in the step of calculating the amount of the blood component, and
the step of calculating the amount of the blood component includes a step of calculating the amount of the blood component using the first blood component amount-dependent current value, the second blood component amount-dependent current value, the third hematocrit-dependent current value, and the fourth hematocrit-dependent current value.

10. The method according to claim 9,
wherein the second step is performed at least twice, and
two or more second blood component amount-dependent current values obtained are used as the second blood component amount-dependent current values in the step of calculating the amount of the blood component.

11. The method according to claim 9,
wherein
all portions of the first step and the second step are simultaneously performed, and
the second step is performed at least twice.

12. The method according to claim 9,
wherein
the second step is performed at least twice, and
portions of the first steps and the second steps are simultaneously performed.

13. The method according to claim 9,
wherein the first reagent layer and the second reagent layer each contain a mediator.

14. The method according to claim 9,
wherein the first reagent layer and the second reagent layer further contain an oxidoreductase.

* * * * *